US009180113B2

(12) United States Patent
Nazzal et al.

(10) Patent No.: US 9,180,113 B2
(45) Date of Patent: Nov. 10, 2015

(54) TOCOTRIENOL COMPOSITIONS

(75) Inventors: Sami Mahmoud Nazzal, Monroe, LA (US); Paul W. Sylvester, West Monroe, LA (US)

(73) Assignee: First Tech International Limited, Tianzhu Town, Beijing (CN)

( * ) Notice: Subject to any disclaimer, the term of this patent is extended or adjusted under 35 U.S.C. 154(b) by 943 days.

(21) Appl. No.: 12/873,424

(22) Filed: Sep. 1, 2010

(65) Prior Publication Data

US 2011/0052704 A1    Mar. 3, 2011

Related U.S. Application Data

(60) Provisional application No. 61/238,905, filed on Sep. 1, 2009, provisional application No. 61/256,416, filed on Oct. 30, 2009, provisional application No. 61/246,600, filed on Sep. 29, 2009.

(51) Int. Cl.

| | |
|---|---|
| *A61K 9/18* | (2006.01) |
| *A61K 31/355* | (2006.01) |
| *A61K 9/107* | (2006.01) |
| *A61K 9/51* | (2006.01) |
| *A61K 31/40* | (2006.01) |
| *A61K 31/404* | (2006.01) |
| *A61K 31/435* | (2006.01) |
| *A61K 31/47* | (2006.01) |
| *A61K 31/505* | (2006.01) |
| *A61K 45/06* | (2006.01) |
| *A61K 47/10* | (2006.01) |
| *A61K 47/14* | (2006.01) |
| *A61K 47/22* | (2006.01) |

(52) U.S. Cl.
CPC ............. *A61K 31/355* (2013.01); *A61K 9/1075* (2013.01); *A61K 9/5123* (2013.01); *A61K 31/40* (2013.01); *A61K 31/404* (2013.01); *A61K 31/435* (2013.01); *A61K 31/47* (2013.01); *A61K 31/505* (2013.01); *A61K 45/06* (2013.01); *A61K 47/10* (2013.01); *A61K 47/14* (2013.01); *A61K 47/22* (2013.01)

(58) Field of Classification Search
None
See application file for complete search history.

(56) References Cited

U.S. PATENT DOCUMENTS

| | | | |
|---|---|---|---|
| 4,880,634 A | 11/1989 | Speiser | |
| 6,043,269 A | 3/2000 | Jacobsen et al. | |
| 6,387,882 B1 | 5/2002 | Ogata | |
| 6,441,029 B1 | 8/2002 | Elson | |
| 2002/0032171 A1* | 3/2002 | Chen et al. | 514/54 |
| 2002/0161032 A1 | 10/2002 | Guivarch et al. | |
| 2003/0077297 A1* | 4/2003 | Chen et al. | 424/400 |
| 2004/0176311 A1 | 9/2004 | Elson et al. | |
| 2007/0207196 A1 | 9/2007 | Zhang | |
| 2010/0273869 A1 | 10/2010 | Sylvester et al. | |

FOREIGN PATENT DOCUMENTS

| | | |
|---|---|---|
| WO | WO03/039461 A2 | 5/2003 |
| WO | WO2006/102768 A1 | 5/2006 |
| WO | WO2006/094791 A1 | 9/2006 |

OTHER PUBLICATIONS (The Merck Index—An Encyclopedia of Chemicals, Drugs, and Biologicals (14th Edition ED 2006—Version 14.9 through Knovel, pp. 1-2.*
Sigma-Aldrich (Material Safety Data Sheet Version 5.0, pp. 1-6).*
Muchow, Mark; Lipid Nanoparticles with a Solid Matrix (SLN®, NLC®, LDC®) for Oral Drug Delivery; Drug Development and Industrial Pharmacy, 2008, 1394-1405, vol. 34, UK
Joshi, Medha; Lipid nanoparticles for parenteral delivery of actives; European Journal of Pharmaceutics and Biopharmaceutics; 161-172; 2009; vol. 71; Germany.
Manjunath, K.; Solid Lipid Nanoparticles as Drug Delivery Systems; Methods Find Exp. Clin. Parmocol.; 127-144; 2005; vol. 27(2).
Ali et al., "Preparation and in vitro antiproliferative effect of tocotrienol loaded lipid nanoparticles," Jan. 5, 2010, Colloids and Surfaces A: Physicochemical and Engineering Aspects, vol. 353, Is. 1, p. 43-51, entire document.
PCT Search Report and Written Opinion from PCT Application No. PCT/US 10/47454.
Shirode et. al., Synergistic anticancer effects of combined g-tocotrienol and celecoxib treatment are associated with suppression in Akt and NFkB signaling Biomedicine & Pharmacotherapy, Nov. 14, 2009, pp. 327-332, vol. 64, Elsevier.
Shirode et. al., Mechanisms Mediating the Synergistic Anticancer Effects of Combined γ-Tocotrienol and Celecoxib Treatment J. Bioanalysis & Biomedicine 2011, pp. 7-Jan., vol. 3(1).
Pearce et al., Inhibitors of Cholesterol Biosynthesis Hypocholesterolemic and Antioxidant Activities of Benzopyran and Tetrahydronaphthalene Analogues of the Tocotrienols Journal of Medicinal Chemistry, 1994, pp. 526-541, vol. 37, No. 4, American Chemical Society.
McIntyre et al. Antiproliferative and Apoptotic Effects of Tocopherols and Tocotrienols on Preneoplastic and Neoplastic Mouse Mammary Epithelial Cells Society for Experimental Biology and Medicine, 2000, pp. 292-301, vol. 224.
Sylvester et al., Role of Tocotrienols In the Prevention of Cardiovascular Disease and Breast Cancer Current Topics in Nutraceutical Research, 2003, pp. 1-16 vol. 1(2).
Shah et al., Tocotrienol-Induced Caspase-8 Activation Is Not Associated with Death Receptor Apoptotic Signaling in Neoplastic Mammary Epithelial Cells Society for Experimental Biology and Medicine, 2004 p. 229.

(Continued)

*Primary Examiner* — Snigdha Maewall
(74) *Attorney, Agent, or Firm* — John B. Edel; Edel Patents LLC

(57) ABSTRACT

Compositions containing tocotrienol, non-tocotrienol lipids and surface active agents; compositions containing particles having a statin and a tocotrienol wherein the particle size is less than 1000 nm; and microemulsions containing a statin and a tocotrienol are disclosed. Methods relating to the creation of such compositions and the use of such compositions are further disclosed.

7 Claims, 48 Drawing Sheets

(56) References Cited

OTHER PUBLICATIONS

Shah et al., γ-Tocotrienol Inhibits Neoplastic Mammary Epithelial Cell Proliferation by Decreasing Akt and Nuclear Factor κB, Activity Society for Experimental Biology and Medicine, 2005, pp. 235-241.
Shah et al., Tocotrienol-induced cytotoxicity is unrelated to mitochondrial stress apoptotic signaling in neoplastic mammary epithelial cells, Biochem. Cell Biol., 2005, pp. 86-95, vol. 83.
Matter et al., Structural Requirements for Factor Xa Inhibition by 3-Oxybenzamides with Neutral P1 Substituents: Combining X-ray Crystallography, 3D-QSAR and Tailored Scoring Functions, Journal of Medical Chemistry, Apr. 13, 2005, pp. 3290-3312, vol. 25 American Chemical Society.
Samant et al., γ-Tocotrienol inhibits ErbB3-dependent PI3K/Akt mitogenic signalling in neoplastic mammary epithelial cells Cell Proliferation, 2006, pp. 563-574, vol. 39, Blackwell Publishing Ltd.
Sylvester, Vitamin E and Apoptosis Vitamins and Hormones, 2007, pp. 329-356, vol. 76, Elsevier, Inc.
Kashiwagi et al., A redox-silent analogue of tocotrienol inhibits hypoxic adaption of lung cancer cells, Biochemical and Biophysical Research Communication, Nov. 8, 2007, pp. 875-881, vol. 365, Elsevier, Inc.
Constantinou et al., Vitamin E and cancer: An insight into the anticancer activities of vitamin E isomers and analogs, International Journal of Cancer, May 29, 2008, pp. 739-752, vol. 123, Wiley-Liss, Inc.
Chang et al., Evidence of γ-Tocotrienol as an Apoptosis-Inducing, Invastion-Suppressing, and Chemotherapy Drug-Sensitizing Agent in Human Melanoma Cells Nutrition and Cancer, Nutrition and Cancer, 2009, pp. 357-366, vol. 61 (3).
Wali et al., Combined Treatment of c-Tocotrienol with Statins Induce Mammary Tumor Cell Cycle Arrest in G1, Society for Experimental Biology and Medicine, 2009, pp. 639-650.
Ali et al., Development and validation of a reversed-phase HPLC method for the simultaneous analysis of simvastatin and tocotrienols in combined dosage forms, Journal of Pharmaceutical and Biomedical Analysis, Feb. 20, 2009, pp. 950-956, vol. 49 2009, Elsevier, Inc.
Wali et al., Endoplasmic reticulum stress mediates c-tocotrienol-induced apoptosis in mammary tumor cells, Apoptosis, Sep. 23, 2009, pp. 1366-1377, vol. 14.
Elnagar et al., Design and preliminary structure—activity relationship of redox-silent semisynthetic tocotrienol analogues as inhibitors for breast cancer proliferation and invasion, Bioorganic & Medicinal Chemistry, Nov. 27, 2009, pp. 755-768, vol. 18, Elsevier, Inc.
Gupte et al., CoMFA and CoMSIA 3D-QSAR Studies on S6-(4-nitrobenzyl)mercaptopurine riboside (NBMPR) analogs as inhibitors of human equilibrative nucleoside transporter 1 (Hent1), Bioorganic & Medicinal Chemistry Letters, 2009, pp. 314-318, vol. 19, Elsevier, Inc.
Abuasal et al., Intestinal Absorption of γ-Tocotrienol Is Mediated by Niemann-Pick C1-Like 1: In Situ Rat Intestinal Perfusion Studies, Drug Metabolism and Disposition, 2010, pp. 939-945, vol. 38(6).
Aggarwal et al., Tocotrienols, the vitamin E of the 21st century: Its potential against cancer and other chronic diseases, Biochemical Pharmacology, 2010, pp. 1-19, vol. 10676, Elsevier, Inc.
Bachawal et al., Enhanced antiproliferative and apoptotic response to combined treatment of g-tocotrienol with erlotinib or gefitinib in mammary tumor cells, BMC Cancer, 2010, pp. 1-13, vol. 10:14.
Bachawal et al., Combined γ-Tocotrienol and Erlotinib/Gefitinib Treatment Suppresses Stat and Akt Signaling in Murine Mammary Tumor Cells, Anticancer Research, 2010, pp. 429-438, vol. 30.
MUDIT Synthesis of Fluorescent Analogues of the Anticancer Natural Products 4-Hydroxyphenylmethylene Hydantoin and δ-Tocotrienol, Natural Product Communications, 2010, pp. 1623-1626, vol. 5(10), Natural Product Communications, Westerville, Ohio.
Samant et al., Anti-proliferative effects of c-tocotrienol on mammary tumour cells are associated with suppression of cell cycle progression, Cell Proliferation, 2010, pp. 77-83, vol. 43, Blackwell Publishing Ltd.
Sylvester et al., The Value of Tocotrienols in the Prevention and Treatment of Cancer, Journal of the American College of Nutrition, 2010, pp. 324S-333S, vol. 29(3), American College of Nutrition.
El Sayed et al., Biocatalytic and semisynthetic optimization of the anti-invasive tobacco (1S,2E,4R,6R,7E,11E)-2,7,11-cembratriene-4,6-diol, Bioorganic & Medicinal Chemistry, Jan. 3, 2008, pp. 8066-8075, vol. 18, Elsevier, Inc.
Ali et al., Preparation, characterization, and anticancer effects of simvastatin-tocotrienol lipid nanoparticles, International Journal of Pharmaceuticals, Feb. 10, 2010, pp. 233-231, vol. 389, Elsevier, Inc.
Ali et al., Molecular interaction and localization of tocotrienol-rich fraction (TRF) within the matrices of lipid nanoparticles: Evidence studies by Differential Scanning Calorimetry (DSC) and Proton Nuclear Magnetic Resonance spectroscopy (1H NMR) Colloids and Surfaces B:, Biointerfaces, 2010, pp. 286-297, vol. 77, Elsevier, Inc.
Behery et al., Redox-silent tocotrienol esters as breast cancer proliferation and migration inhibitors, Bioorganic & Medicinal Chemistry, 2010, pp. 8069-8075, vol. 18, Elsevier, Inc.
Ali et al., Preparation, characterization, and anticancer effects of simvastatin-tocotrienol lipid nanoparticles Colloids and Surfaces A: Physiochem. Eng., Aspects, Oct. 30, 2009, pp. 43-51, vol. 353, Elsevier, Inc.
ACS SciFinder search engine results, http://www.cas.org/products/sfacad/index.html Query: Tocotrienol.
ACS SciFinder search engine results, http://www.cas.org/products/sfacad/index.html Query: Bioavailability Tocotrienol.
ACS SciFinder search engine results, http://www.cas.org/products/sfacad/index.html Query: Tocotrienol Potential Anticancer.
ACS SciFinder search engine results, http://www.cas.org/products/sfacad/index.html Query: Solubility Tocotrienol.
Sen, et al., Journal of Biol Chem, 2000, pp. 13049, vol. 275.
Crowell, et al., Journal Biol Chem, 1991, pp. 17679, vol. 266.
Elson, et al., Journal Nutr., 1994, pp. 607, vol. 124.
Sporn, et al., Nat. Rev. Cancer, 2002, pp. 537, vol. 2.
Shukla, et al., Nutr. Cancer, 2005, pp. 18, vol. 53.
Nesaretnam, et al., Lipids, 1995, pp. 1139, vol. 30.
Qureshi, et al., Atherosclerosis, 2002, pp. 199, vol. 161.
Khanna, et al., Journal of Biol Chem, 2003, pp. 43508, vol. 278.
Akaho, et al., Drug Metab. Dispos., 2007, pp. 1502, vol. 35.
Takata, et al., Journal Lipid Res, 2002, pp. 2196, vol. 43.
Mazzini, et al., Journal Org. Chem, 2009, pp. 2063, vol. 13.
Tomic-Vatic, et. al., Int. J. Cancer, 2005, pp. 188, vol. 117.
Kashiwagi, et al., Biochem, Biophys. Res. Commun., 2008, pp. 875, vol. 365.
Ali, et al., Pharm Biomed. Anal., 2009, pp. 950, vol. 49.
Chang, et al., Nutr. Cancer, 2009, pp. 357, vol. 61.
Yap, et al., Br. J. Cancer, 2008, pp. 1832, vol. 99.
Tamilarasan, et al., Cell Biol., 2006, pp. 17, vol. 7.
Borghesani,, et al., Development, 2002, pp. 1435, vol. 6.
Kubinyi, et al., Burger's Medicinal Chemistry, 1995, pp. 497-571, vol. 1.
Denizot, et al., Immunol, Methods, 1986, pp. 271, vol. 89.
Kleinman, et al., Cancer Biol., 2005, pp. 378, vol. 15.
Koblinski, et al., Cancer Res., 2005, pp. 7370, vol. 65.
El Sayed et al., Latrunculin A and Its C-17-0 Carbamates Inhibit Prostate Tumor Cell Invasion and HIF-1 Activation in Breast Tumor Cells, Journal of Natural Products, 2008, pp. 396-402, vol. 71.
Arya et al., Design and synthesis of analogs of Vitamin E: Antiproliferative activity against human breast adenocarcinoma cells, Bioorganic Medicinal Chemistry Letters, Sep. 22, 1998, pp. 2433-2438, vol. 8(18).
McIntyre et al., Antiproliferative and Apoptotic Effects of Tocopherols and Tocotrienols on Normal Mouse and Mammary Epithelial Cells Lipids, 2000, pp. 171-180, vol. 35(2), AOCS Press.
Shah et al., Role of Caspase-8 Activation in Mediating Vitamin E-Induced Apoptosis in Murine Mammary Cancer Cells, Nutrition and Cancer, 2003, pp. 236-246, vol. 45(2), Lawrence Erlbaum Associates, Inc.
Liua et al., Inhibitory Effects of γ-tocotrienol on invastion and metastasis of human gastric denocarcinoma SGC-7901 Cells, Journal of Nutritional Biology, Feb. 5, 2009, vol. 11, Elsevier, Inc.
EPO Search Report from Application No. 10814397.5, Feb. 4, 2013.

* cited by examiner

| Formulation | glyceryl behenate (% w/v) | α-tocopherol (mM) | Tocotrienol rich fraction (mM) | Simvastatin (mM) | Polox. 188 (% w/v) | Z-ave (nm) | PI | zeta potent (mV) |
|---|---|---|---|---|---|---|---|---|
| Unloaded solid lipid nanoparticle[a] | 0.50 | 0 | 0 | 0 | 0.25 | 151.7 ±1.2 | 0.28±0.00 | -21.7±0. |
| simvastatin -tocotrienol rich fraction nanostructured lipid carrier[b] | 0.25 | 0 | 5 | 1 | 0.25 | 107.5 ±0.73 | 0.29±0.01 | -13.4± 0. |
| simvastatin – α-tocopherol nanostructured lipid carrier[c] | 0.25 | 5 | 0 | 1 | 0.25 | 106.8 ±2.54 | 0.253±0.01 | -9.0±0.8 |
| tocotrienol rich fraction-nanostructured lipid carrier[d] | 0.25 | 0 | 5 | 0 | 0.25 | 100.3 ±0.91 | 0.233±0.01 | -13.5±0. |
| α-tocopherol-nanostructured lipid carriers[e] | 0.25 | 5 | 0 | 0 | 0.25 | 101.2 ±1.27 | 0.203±0.02 | -10.5±1. |

[a] Unloaded solid lipid nanoparticles, blank solid lipid nanoparticles made from Compritol 888 ATO (glyceryl behenate) only as a lipid phase.
[b] simvastatin -tocotrienol rich fraction-glyceryl behenate nanostructured lipid carriers, nanostructure lipid carriers with simvastatin and tocotrienol rich fraction (tocotrienol rich fraction).
[c] simvastatin - α-tocopherol-glyceryl behenate nanostructured lipid carriers, nanostructure lipid carriers with simvastatin and α-tocopherol (α T).
[d] tocotrienol rich fraction-nanostructured lipid carriers, nanostructure lipid carriers with tocotrienol rich fraction.
[e] α-tocopherol-nanostructured lipid carriers, nanostructure lipid carriers with α-tocopherol.

Fig. 11

TOCOTRIENOL COMPOSITIONS

This application claims the benefit of U.S. Provisional Application No. 61/238,905 entitled "Drug Delivery System" filed Sep. 1, 2009; U.S. Provisional Application No. 61/256,416 entitled "Simvastatin-Tocotrienol Lipid Compositions" filed Oct. 30, 2009; and U.S. Provisional Application No. 61/246,600 entitled "Tocotrienol Nanoparticles" filed Sep. 29, 2009.

Vitamin E is a generic term for a group of compounds including tocopherols and tocotrienols. Treatments for cancer and neoplastic disease in mammals in general and humans in particular are in need of drug delivery methods and compositions that can successfully bring an efficacious amount of the required drug to a targeted area. Currently known methods of drug delivery have not adequately met this need. For that reason, further methods and compositions having potential for use in the delivery of Vitamin E compounds to a targeted area are needed.

Disclosed herein are embodiments of the present invention that address the needs described above by providing compositions and methods that can be used for the delivery of Vitamin E compounds or derivatives of those compounds to an area of a mammal in need of these compounds. These compositions and methods are useful both for the types of treatments described herein and for the development of further treatments.

A pharmacological composition having features of the present invention comprises a group of particles having a mean diameter of less than or about 1000 nm wherein the particles contain a therapeutic amount of tocotrienol, the particles contain a non-tocotrienol lipid, and the particles contain a surface active agent. In an embodiment of the invention, the mean particle diameter is less than or about 400 nm. In a related embodiment of the invention, the mean particle diameter is less than or about 250 nm. In an embodiment of the invention, the sum of the weight of the tocotrienol and the non-tocotrienol lipid is equivalent to or greater than or about one sixth of the weight of any surface active agent present. In a related embodiment of the invention, the sum of the weight of the tocotrienol and the non-tocotrienol lipid is equivalent to or greater than or about the weight of any surface active agent present. In a further related embodiment of the invention, the sum of the weight of the tocotrienol and the non-tocotrienol lipid is equivalent to or greater than or about four times the weight of any surface active agent present. In another embodiment of the invention, the group of particles has a polydispersity index below 0.3. In an embodiment of the invention, the melting point of the non-Tocotrienol lipid is greater than or about 37° C. and in a further embodiment the non-Tocotrienol lipid is greater than or about 50° C. In yet another embodiment of the invention, the melting point of the surface active agent is greater than or about 37° C. and in a still further embodiment of the invention the melting point of the surface active agent is greater than or about 50° C. In an embodiment of the invention, the surface active agent has surface active agent properties associated with surface active agents that rate 10 or greater on the hydrophilic-lipophilic balance scale.

A pharmacological composition having features of the present invention comprises a group of particles wherein the particles contain a statin and a tocotrienol; wherein the statin and the tocotrienol are present in a quantity sufficient to deliver a beneficial therapeutic effect; and wherein the particles of the group of particles have a particle size average of less than 1000 nm. In separate but related embodiments, the group of particles has a particle size average of less than about 150 nm; the weight ratio of the statin to the tocotrienol is about 0.2 to 1; the particles contain a non-tocotrienol lipid; the non-tocotrienol lipid is glyceryl behenate; the weight ratio of the statin to the non-tocotrienol lipid is about 0.2 to 1; the weight ratio of the tocotrienol to the non-tocotrienol lipid is about 1 to 1; the non-tocotrienol lipid is a solid at 25° C.; the melting point of the non-tocotrienol lipid is greater than or about 37° C.; the melting point of the non-tocotrienol lipid is greater than or about 50° C.; the particles contain a surfactant; the surfactant is a solid or a semisolid at room temperature; the melting point of the surfactant is greater than or about 37° C.; the melting point of the surfactant is greater than or about 50° C.; the surfactant has surface active agent properties associated with surface active agents that rate 10 or greater on the hydrophilic-lipophilic balance scale; the surfactant is polaxamer; the particles of the group of particles have a particle size average of less than or about 400 nm; the particles of the group of particles have a particle size average of less than or about 250 nm; the particles of the group of particles has a polydispersity index below 0.3; the particles are in the form of a homogeneous suspension; no substantial amount of statin is present in a crystalline form; when the particles are analyzed under wide angle powder X-ray diffraction no substantial peaks exist that are characteristic of the statin in crystalline form; the particles are in the form of nanostructured lipid carriers; about 40% or more of the simvastatin within the composition is within the particles; about 80% or more of the simvastatin within the composition is within the particles; the particles are sufficiently stable to neither substantially decompose nor substantially agglomerate after 6 months of storage at room temperature while protected from light; and the statin is a statin selected from the group consisting of atorvastatin, cerivastatin, fluvastatin, lovastatin, mevastatin, pitavastatin, pravastatin, rosuvastatin, and simvastatin.

An in vivo product having features of the present invention is produced by the process of administering one of the pharmacological compositions described herein to a mammalian patient by a form of delivery selected from the methods of delivery consisting of intravenous, intraperitoneal, subcutaneous, intramuscular, ocular, oral, transdermal, topical and inhalation.

A pharmacological composition having features of the present invention comprises a microemulsion containing a statin and a tocotrienol wherein the statin and the tocotrienol are present in a quantity sufficient to deliver a beneficial therapeutic effect. In a related embodiment, the statin is simvastatin and the tocotrienol is a tocotrienol selected from the group of tocotrienols consisting of tocotrienol rich fraction of palm oil and γ-tocotrienol.

A pharmacological composition having features of the present invention comprises nanostructured lipid carriers wherein said nanostructured lipid carriers comprise a statin at a first amount and a tocotrienol at a second amount; wherein the first amount and the second amount are sufficient to deliver a desired clinical result; wherein the first amount and the second amount would not be sufficient to deliver the desired clinical result if delivered in the absence of the nanostructured lipid carriers.

A method of preparing a pharmaceutical composition having features of the present invention comprises the steps of: combining a statin and a tocotrienol; melting the statin and the tocotrienol; mixing the statin and the tocotrienol with an aqueous surfactant solution; homogenizing the mixture of the statin, the tocotrienol, and the surfactant solution; and cooling the homogenized mixture to a temperature at which nanoparticles form. In separate but related embodiments, the statin is simvastatin; the tocotrienol is γ-tocotrienol; the tocotrienol is a tocotrienol rich fraction of palm oil; the surfactant, the statin and the tocotrienol have a combined concentration from about 0.25% to about 10% w/v in the homogenized mixture. Pharmaceutical composition having features of the present invention can be produced by these processes.

A method of treating or preventing a form of cancer having features of the present invention comprises administering to a mammalian patient in need of said treatment or prevention either a first therapeutic amount of a composition or a second therapeutic amount of a pharmaceutically acceptable salt of said composition, wherein the composition is one of the pharmacological compositions described herein.

A method of treating or preventing a form of cancer having features of the present invention comprises exposing a mammalian cell to either a first therapeutic amount of a composition or a second therapeutic amount of a pharmaceutically acceptable salt of said composition, wherein the composition is one of the pharmacological compositions described herein.

A pharmacological composition having features of the present invention comprises a group of particles wherein the particles of the group have a mean diameter of less than or about 1000 nm wherein the particles contain a therapeutic amount of tocotrienol, wherein the particles contain a non-tocotrienol lipid, wherein the particles contain a surface active agent, and wherein the weight ratio of all surface active agents to all lipids is between about 0.25 to 1.0 and about 3.0 to 1.0. In separate but related embodiments of the invention: the weight ratio of all surface active agents within the particles to all lipids within the particles is about 0.5 to 1.0; the non-tocotrienol lipid is a lipid capable of forming nanostructured lipid carriers containing tocotrienol with a mean particle diameter of less than 100 nanometers; the non-tocotrienol lipid is a lipid that is capable of enhancing the antiproliferative effect of the tocotrienol as compared to a comparable quantity of tocotrienol delivered without the non-tocotrienol lipid; the particles are capable of absorption by cancerous cells at a tocotrienol delivery rate that is greater than the rate of tocotrienol delivery from a comparable quantity of tocotrienol delivered without the non-tocotrienol lipid; the non-tocotrienol lipid is a lipid selected from the group comprising cetyl palmitate, glyceryl tristearate, glyceryl behenate, and glyceryl palmitostearate; the non-tocotrienol lipid is a glyceride of behenic acid; the surface active agent is a poloxamer; the mean particle diameter is less than or about 400 nm; the mean particle diameter is less than or about 250 nm; the group of particles has a polydispersity index below 0.3; the melting point of the non-tocotrienol lipid is greater than or about 37° C.; the melting point of the non-tocotrienol lipid is greater than or about 50° C.; the melting point of the surface active agent is greater than or about 37° C.; the melting point of the surface active agent is greater than or about 50° C.; and the surface active agent has surface active agent properties associated with surface active agents that rate 10 or greater on the hydrophilic-lipophilic balance scale.

A method of treating or preventing a form of cancer having features of the present invention comprises administering to a mammalian patient in need of said treatment or prevention either a first therapeutic amount of a compound or a second therapeutic amount of a pharmaceutically acceptable salt of said compound, wherein said compound is a pharmacological composition described above.

A method of treating or preventing a form of cancer having features of the present invention comprises exposing a mammalian cell to either a first therapeutic amount of a compound or a second therapeutic amount of a pharmaceutically acceptable salt of said compound, wherein said compound is a pharmacological composition described above. In an embodiment of the invention, the mammalian cell is in a live mammal; the compound is in the mammals blood; and the therapeutic amount of tocotrienol has a concentration of greater than 4 µM in the blood. In a further embodiment of the invention, the mammalian cell is in a live mammal; the compound is in the mammals blood; and the concentration of tocotrienol in the blood is such that it causes the mammalian cell to be exposed to a tocotrienol concentration less than 6 µM.

A pharmacological composition having features of the present invention comprises: a group of particles wherein the particles of the group have a mean diameter of less than or about 1000 nm; wherein the particles contain a tocotrienol; wherein the particles contain a non-tocotrienol lipid; wherein the particles contain a surface active agent; and wherein the tocotrienol is less than about 50 weight percent of the total weight of lipids in the particles. In another embodiment of the invention, the tocotrienol is about 10 weight percent of the total weight of lipids in the particles.

A method of forming a pharmacological composition having features of the present invention comprises: mixing a tocotrienol, a non-tocotrienol lipid, and a surfactant in an aqueous solution at a temperature above the melting point of the non-tocotrienol lipid creating a mixture wherein the concentration of all lipids present in the mixture is less than or equal to 10 weight percent of the total mixture; homogenizing the mixture to an extent sufficient to create a suspension of particles having a mean particle diameter of less than 500 nm upon cooling of the mixture; and lowering the temperature of the mixture to a temperature below the melting point of the non-tocotrienol lipid, creating particles containing the tocotrienol, the non-tocotrienol lipid and the surface active agent. Another pharmacological composition having features of the present invention comprises the product produced by that method.

BRIEF DESCRIPTION OF THE DRAWINGS

FIG. 11 shows compositions and properties for various nanoparticles and nanostructured lipid carriers.

DETAILED DESCRIPTION

Examples 1(A)-1(E)

Figure 1A:
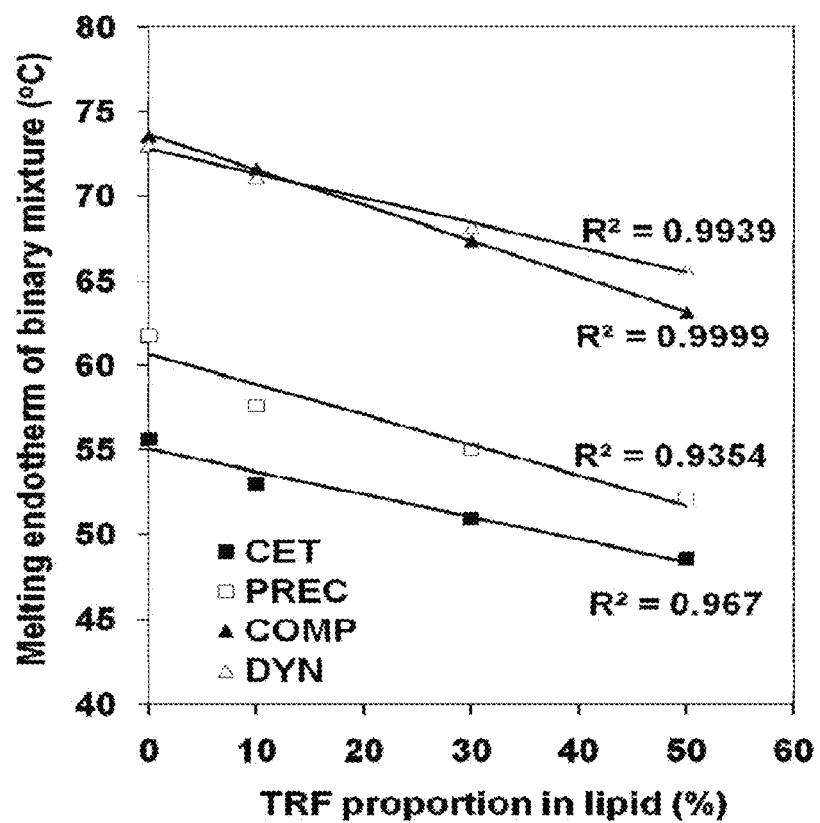
FIG. 1A shows a linear regression graph of the melting endotherm of tocotrienol rich fraction/solid lipids binary mixtures versus proportions of tocotrienol rich fraction.
Figure 1B:
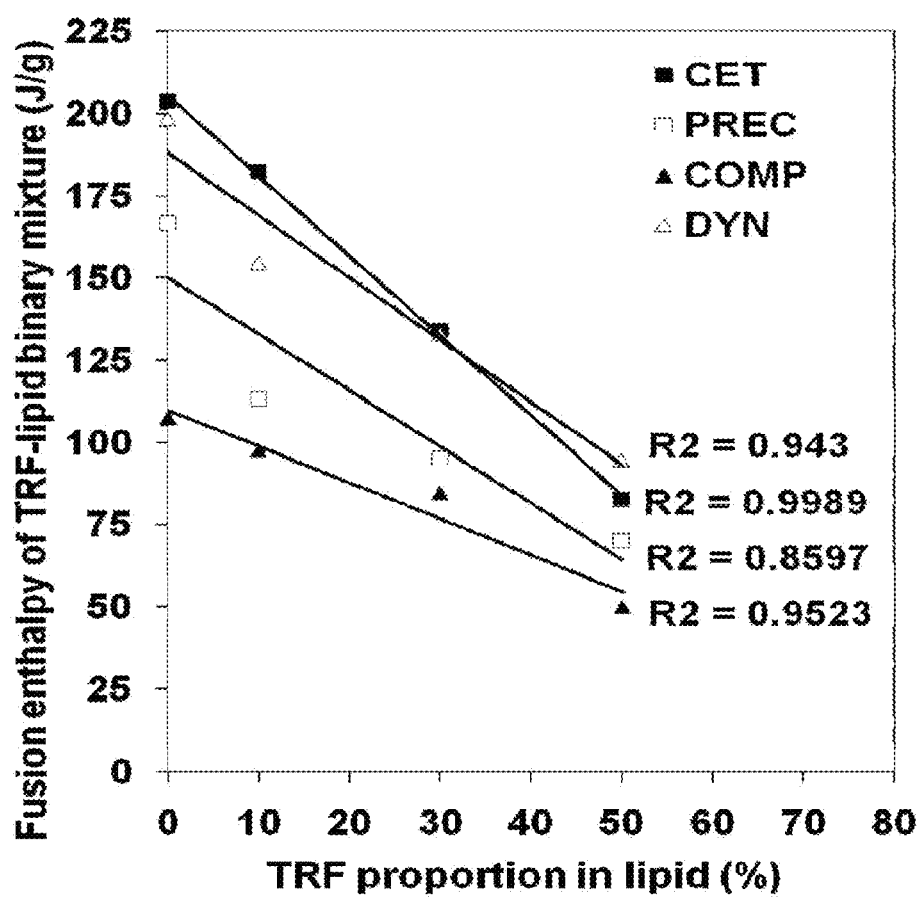
FIG. 1B shows a linear regression graph of the fusion enthalpy of tocotrienol rich fraction/solid lipids binary mixtures versus proportions of tocotrienol rich fraction.
Figure 1C:
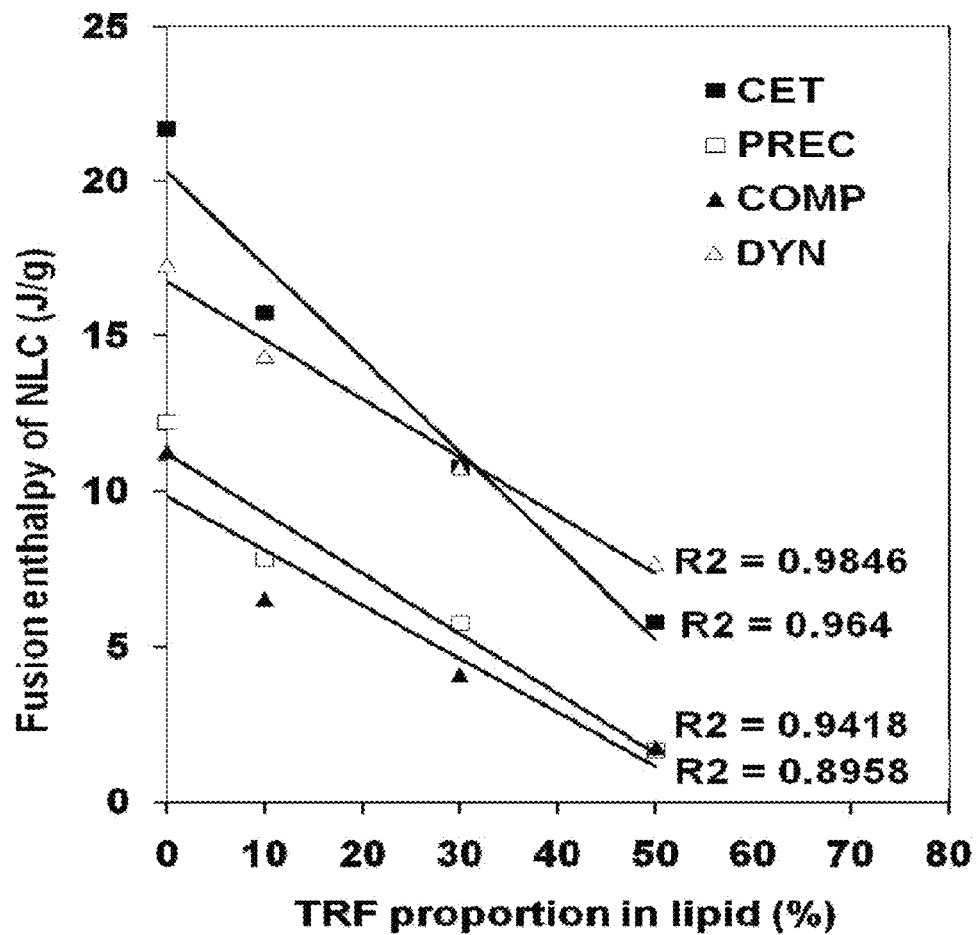
FIG. 1C shows a linear regression graph of the fusion enthalpy of nanostructured lipid carriers versus proportions of tocotrienol rich fraction.
Figure 1D:
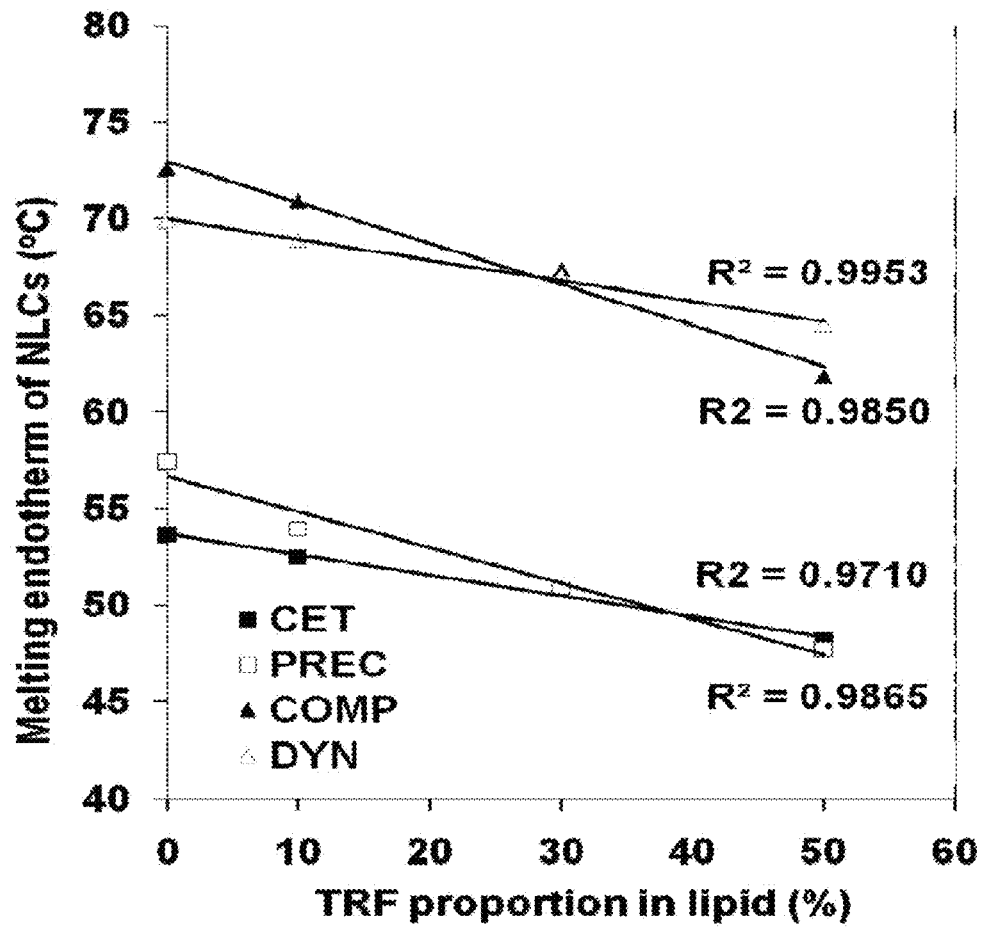
FIG. 1D shows a linear regression graph of the melting endotherm of nanostructured lipid carriers versus proportions of tocotrienol rich fraction.

For the ease of presentation of data, the following abbreviations have been utilized at points throughout the application: solid lipid nanoparticles (SLN); nanostructured lipid carrier (NLC); nanoemulsion (NEmu) tocotrienol rich fraction (TRF); glycerol tristearate sold as Dynasan® 118, (DYN), glyceryl behenate sold as Compritol® 888 ATO (COMP), glycerol palmitostearate sold as Precirol® ATO 5 (PREC), and cetyl palmitate (CET).

A tocotrienol rich extract of palm oil is commonly referred to as tocotrienol-rich-fraction. Tocotrienol-rich-fraction is an oily mixture of tocopherols and tocotrienols, in which tocotrienols constitutes 70-80% of the blend. The fundamental structural difference between the two groups is the phytyl chain, which is unsaturated in tocotrienols and saturated in tocopherols. The isoforms of tocopherols and tocotrienols differ from each other by the degree of methylation of the chromane ring. The following general formula (the "Vitamin E general formula") represents a structure common to the various tocotrienol and tocopherols with Table I showing the individual variations on the common structure for certain tocopherols and tocotrienols.

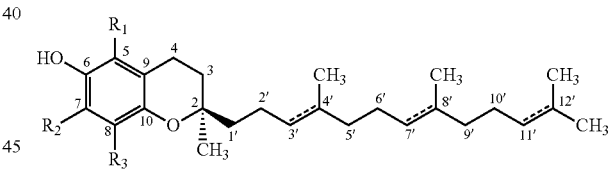

TABLE I

| Compound | $R_1$ | $R_2$ | $R_3$ | Phytyl chain |
|---|---|---|---|---|
| α-tocopherol (20.2%) | $CH_3$ | $CH_3$ | $CH_3$ | Saturated |
| γ-tocopherol | H | $CH_3$ | $CH_3$ | Saturated |
| δ-tocopherol | H | H | $CH_3$ | Saturated |
| α-tocotrienol (16.8%) | $CH_3$ | $CH_3$ | $CH_3$ | Unsaturated |
| γ-tocotrienol (44.9%) | H | $CH_3$ | $CH_3$ | Unsaturated |
| δ-tocotrienol (14.8%) | H | H | $CH_3$ | Unsaturated |

The structure of solid lipid nanoparticles and nanostructured lipid carriers based on tocotrienol-rich-fraction and solid lipids was characterized by thermal analysis using differential scanning calorimetry whereas the mode of tocotrienol-rich-fraction localization was postulated from $^1$H-NMR signal amplitudes. Suitability for use in drug delivery of the solid lipid nanoparticles and nanostructured lipid carriers was evaluated based on the characteristics of the different structures.

Photon correlation spectroscopy and differential scanning calorimetry data revealed that the size, polydispersity, melting endotherm, and fusion enthalpy of the nanoparticles decreased with an increase in tocotrienol-rich-fraction loading. $^1$H-NMR spectra of tocotrienol-rich-fraction-nanostructured lipid carriers broadened as tocotrienol-rich-fraction load decreased from 100% to 30%. Tocotrienol-rich-fraction spectra in nanostructured lipid carriers however, were distinctly different from those observed in tocotrienol-rich-fraction-microemulsion and solid lipid nanoparticles.

Tocotrienol-rich-fraction molecules are preferentially entrapped within the cores of nanostructured lipid carriers yielding stable spherical-nanoparticles. While the crystalline structure of the solid lipids was distorted, tocotrienol-rich-fraction was not expelled from the nanoparticles. Rather, tocotrienol-rich-fraction mobility was suppressed within the inner core of the nanostructured lipid carriers, which was confirmed by $^1$H-NMR analysis. Solid lipid nanoparticles are aqueous colloidal dispersions with a size in the range of 50-1000 nm, the matrix of which is comprised of biodegradable and biocompatible solid lipids. The mode of tocotrienol-rich-fraction entrapment and/or affinity to the solid lipids as well as its tendency to form supercooled melts were tested with thermal analysis and Proton Nuclear Magnetic Resonance ($^1$H-NMR) studies. Thermal analysis via differential scanning calorimetry was used to study the degree of crystallinity and the polymorphic state of lipids whereas the mobility, arrangement, and the mode of liquid entrapment within solid matrices were evaluated by $^1$H-NMR. The effect of tocotrienol-rich-fraction on the crystallinity and supercooling of the tocotrienol-rich-fraction/solid-lipid physical blends and nanostructured lipid carriers was evaluated by differential scanning calorimetry. The mode of tocotrienol-rich-fraction entrapment within the nanostructured lipid carriers was evaluated by $^1$H-NMR. To further illustrate the effect of nanostructured lipid carrier composition on tocotrienol-rich-fraction entrapment, four high melting point lipids that vary in their chemistry, namely glycerol tristearate (sold under the trade name Dynasan® 118), glyceryl behenate (sold under the trade name Compritol® 888 ATO), glycerol palmitostearate (sold under the trade name Precirol® ATO 5), and cetyl palmitate, were selected as the matrix forming lipids. The long term stability of the tocotrienol-rich-fraction-nanostructured lipid carriers with respect to their size was also evaluated.

For Examples 1(A)-1(E) Cetyl palmitate was purchased from TCI America (Portland, Oreg.). Deuterium oxide (Deuterated water) and deuterated chloroform (chloroform-D) were purchased from Cambridge Isotope Laboratories, Inc. (Andover, Mass.). Glycerol tristearate was provided by Sasol Chemicals North America LLC (Houston, Tex.). Glyceryl behenate (a mixture of ~15% mono-, 50% di- and 35% triglycerides of behenic acid) and glycerol palmitostearate were provided by Gattefossé (Saint-Priest, Cedex, France). Poloxamer 188 is a compound with the general formula, $$H-[O-CH_2-CH_2]_x-[O-\underset{\underset{\delta}{CH_3}}{\overset{\overset{\beta}{H}}{C}}-\overset{\gamma}{CH_2}]_Y-[O-CH_2-CH_2]_x-OH$$

wherein x is approximately 79 and y is approximately 28, which is sold under the trade name Lutrol® F 68 NF, and obtained from BASF (Florham Park, N.J.). Tocotrienol-rich-fraction of palm oil (tocotrienol-rich-fraction, which contains 20.2% α-tocopherol, 16.8% α-tocotrienol, 44.9% γ-tocotrienol, 14.8% δ-tocotrienol, and 3.2% of a non-vitamin E lipid soluble contaminants) was provided by the Malaysian Palm Oil Board (Selangor, Malaysia).

Example 1(A)

Nanoparticle Preparation

Batches were manufactured by hot oil dispersed in water "o/w" microemulsion using a high-shear homogenization technique in a manner similar to that described in "Optimization of Procedure Parameters and Physical Stability of Solid Lipid Nanoparticles in Dispersions" P. Ahlin, J. Kristl, and J. Šmid-Kober. *Acta Pharm.* 48:257-267 (1998). A 10% lipid phase was melted at 85° C. Depending on the melting point of the lipid used, the lipid solution was heated to a temperature from 65 to 95° C. In a separate container five percent of poloxamer 188, a surface active agent, was dissolved in water (85%). In the case of NMR studies, deuterium oxide was used in place of the water. The aqueous surfactant solution was preheated to 85° C. Then, the solution was added to the molten lipid. The premix was homogenized at 20,000 rpm for 5 minutes using a homogenizer (IKA® Ultra-Turrax T8 mixer from IKA® Works Inc., NC, USA). The formed hot pre-emulsion was then ultrasonicated for 10 minutes using an ultrasonic homogenizer (Biologics, Inc., VA). The power on this ultrasonic homogenizer was set at 40-50% and the pulsar was set at 60%. Nanoparticles were subsequently formed by annealing the sonicated microemulsion overnight at 4° C. For preparing nanostructured lipid carriers, tocotrienol-rich-fraction was incorporated at 10%, 30%, and 50% (w/w) of the total lipid phase. Tocotrienol nanostructured lipid carriers were prepared using a similar procedure as that used to prepare solid lipid nanoparticles described above with one exception. The desired quantity of tocotrienol was first added to the solid lipid in a vial and then the vial was heated to a temperature above the melting point of the solid lipid. Then, the pre-heated surfactant solution of poloxamer was added to the blend of the molten lipid with tocotrienol in a stepwise procedure identical to that described above for the preparation of solid lipid nanoparticles. A nanoemulsion of tocotrienol-rich-fraction (100% of total lipid phase, tocotrienol-rich-fraction-nanoemulsion) was prepared by a similar method as used in the preparation of solid lipid nanoparticles and nanostructured lipid carriers. The only difference is that no solid lipids were used to prepare the microemulsions. For differential scanning calorimetry studies, binary mixtures of tocotrienol-rich-fraction and the individual solid lipids were vortexed at 85° C. and then allowed to cool down to room temperature. In other embodiments of the invention, lipid concentrations ranging from 0.25% to 10% may be made. In an embodiment of the invention, the amount of surfactant is fixed so that the ratio of the lipid blend to the surfactant would fall within the range from about 1:6 to about 1:0.1. In another embodiment of the invention, the amount of surfactant is fixed so that the ratio of the lipid blend to the surfactant would fall within the range from about 1:1 to about 1:0.25.

Mean particle size and population distribution (polydispersity index or "PI") of solid lipid nanoparticles, nanostructured lipid carrier, and tocotrienol-rich-fraction-nanoemulsion were measured by photon correlation spectroscopy at 90° angle and 25° C. using a zeta potential/particle size analyzer (Nicomp™ 380 ZLS from PSS Inc., Santa Barbara, Calif.). All samples were diluted with 0.2 µL pre-filtered water to an adequate scattering intensity prior to analysis. Particle size and population distribution of solid lipid nanoparticles, nanostructured lipid carriers, and tocotrienol-rich-fraction-nanoemulsion stored at 25° C. was periodically measured over a time span of six months to determine the long term stability of the nanoparticles.

Thermal analysis was performed to verify the solidification and entrapment of tocotrienol-rich-fraction within the solid core. Differential scanning calorimetry analyses were performed using modulated differential scanning calorimetry (model 2920 MDSC from TA Instruments-Waters LLC, New Castle, Del.). Samples (2-3 mg) hermetically sealed in aluminum pans were first heated at a scan rate of 10° C./min from 20° C. to 85° C. then allowed to cool to 10° C. to observe exothermic and recrystallization phenomena. Differential scanning calorimetry analysis was performed on the following samples: (a) blank solid lipid nanoparticle; (b) 10% tocotrienol-rich-fraction-nanoemulsion; (c) nanostructured lipid carrier containing 10%, 30%, and 50% tocotrienol-rich-fraction; (d) physical mixture of blank solid lipid nanoparticles and tocotrienol-rich-fraction-nanoemulsion; (e) tocotrienol-rich-fraction/solid lipid binary mixture; (f) bulk solid lipid; and (g) bulk tocotrienol-rich-fraction. Melting endotherm, fusion enthalpy, and onset temperature were estimated from the generated data. (Universal analysis 2000 version 4.2E software from TA Instruments-Waters LLC, New Castle, Del.). Recrystallization index (RI) was calculated using the following equation:

$$RI(\%) = \frac{\text{Enthalpy}_{SLN\ dispersion}[J/g]}{\text{Enthalpy}_{bulk\ material}[J/g] \cdot \text{Concentration}_{lipidphase}[\%]} \cdot 100$$

High resolution proton nuclear magnetic resonance ($H^1$-NMR) spectra of samples prepared in deuterated water were obtained using a JEOL Eclipse NMR spectrometer operating at 400 MHz and 20° C. Samples were prepared by simply filling an aliquot (approximately 0.7 mL) of each nanodispersion in NMR tubes prior to analysis. In order to verify tocotrienol-rich-fraction entrapment and confirm its chemical stability in nanostructured lipid carriers, approximately 1.0 mL of fresh sample was mixed with 1.5 mL of deuterated chloroform and then sonicated in a bath sonicator (model 5510R-DTH from Bransonic Ultrasonics Co., Dunbury, Conn.) for 10 minutes. The produced nanoemulsion was set aside until two distinct layers (an aqueous layer and a chloform layer) were produced. Both layers were then analyzed independently by $^1$H-NMR, and the spectra were cross matched with chloroformic solution of tocotrienol-rich-fraction and solid lipid.

Data collected in this study were analyzed by one-way analysis of variance (ANOVA), and the results of the statistical analysis were considered significant if their corresponding p-values were less than 0.05. (JMP statistical software package version 7.0)

Example 1(B)

Particle Size

The size of solid lipid nanoparticles and nanostructured lipid carriers depends on many parameters, such as production temperature, sonication time and power, and the nature of the lipid matrix and the surfactant blend. The effect that tocotrienol-rich-fraction incorporation into the lipid phase had on size and homogeneity of the solid lipid nanoparticles was evaluated. The concentration of the lipid phase in the dispersion medium was kept constant at 10% w/v and only the proportion of tocotrienol-rich-fraction in the lipid phase was changed from 0% (blank solid lipid nanoparticle) to 100% (tocotrienol-rich-fraction-nanoemulsion). The particle size and size distribution (PI) of the nanoparticles were measured as described and are shown in Table II below. As shown in the table, the mean particle size ranged from 123.8 nm to 412.4 nm for tocotrienol-rich-fraction-nanoemulsion and solid lipid nanoparticle-cetyl palmitate, respectively. The following relationships of particle size for blank solid lipid nanoparticle were found: solid lipid nanoparticle-cetyl palmitate>solid lipid nanoparticle-glycerol tristearate>solid lipid nanoparticle-glyceryl behenate>solid lipid nanoparticle-glycerol palmitostearate. The lower particle sizes observed with solid lipid nanoparticle-glycerol tristearate, solid lipid nanoparticle-glycerol palmitostearate, and solid lipid nanoparticle-glyceryl behenate, when compared to solid lipid nanoparticle-cetyl palmitate, may be attributed to the presence of partial glycerides in the solid lipids that promote emulsification of the molten globules. Not wishing to be bound by theory, these glycerides may reduce the surface tension and facilitate particle partition during homogenization with a consequent decrease in particle size. The particle size of the nanostructured lipid carriers decreased significantly ($p<0.05$) with an increase in the concentration of tocotrienol-rich-fraction in the formulations. Mean particle size data and values for Polydispersity Index are presented in Table II.

TABLE II

| Batch | Mean particle size (nm.) | Polydispersity index (PI) |
|---|---|---|
| SLN-CET | 412.4 ± 0.5 | 0.317 ± 0.003 |
| NLC-CET-10 | 407.2 ± 0.71 | 0.331 ± 0.014 |
| NLC-CET-30 | 394.3 ± 0.71 | 0.255 ± 0.047 |
| NLC-CET-50 | 283.2 ± 1.55 | 0.189 ± 0.003 |
| SLN-COMP | 212.2 ± 3.25 | 0.303 ± 0.019 |
| NLC-COMP-10 | 187.5 ± 1.31 | 0.244 ± 0.0177 |
| NLC-COMP-30 | 175.45 ± 1.63 | 0.226 ± 0.006 |
| NLC-COMP-50 | 164.1 ± 1.69 | 0.209 ± 0.007 |
| SLN-PREC | 169 ± 6.36 | 0.193 ± 0.002 |
| NLC-PREC-10 | 160.0 ± 1.76 | 0.176 ± 0.002 |
| NLC-PREC-30 | 155.4 ± 1.41 | 0.173 ± 0.044 |
| NLC-PREC-50 | 139.8 ± 2.19 | 0.161 ± 0.009 |
| SLN-DYN | 259.75 ± 3.18 | 0.167 ± 0.018 |
| NLC-DYN-10 | 235.1 ± 0.141 | 0.306 ± 0.021 |
| NLC-DYN-30 | 226.6 ± 4.242 | 0.285 ± 0.009 |
| NLC-DYN-50 | 187.75 ± 3.464 | 0.267 ± 0.028 |
| TRF-NEmu | 123.8 ± 0.424 | 0.161 ± 0.005 |

Mean particle size and size distribution of solid lipid nanoparticles, nanostructured lipid carriers, and tocotrienol-rich-fraction-nanoemulsion (mean ± SD, n = 3)

Example 1(C)

Polydispersity Index

The Polydispersity Index (PI) describes the deviation of the measured autocorrelation function from that of monodisperse sphere dispersions with the same diameter. Low PI values are desirable. High PI usually demonstrates broader particle size distribution. The PI of the solid lipid nanoparticles and nanostructured lipid carriers ranged from 0.161 to 0.331 for tocotrienol-rich-fraction-nanoemulsion and nanostructured lipid carrier-cetyl palmitate-10, respectively (Table II). The observed low PI values for the nanoparticles indicate monomodal and narrow size distribution suggesting nanoparticle monodispersity. Furthermore, PI decreased significantly ($p<0.05$) with an increase in tocotrienol-rich-fraction concentration, suggesting that tocotrienol-rich-fraction incorporation into nanostructured lipid carriers produces more homogeneous particles and particles that are more spherical than tocotrienol-rich-fraction-unloaded solid lipid nanoparticles.

Example 1(D)

Differential Scanning Calorimetry

Differential scanning calorimetry was used to characterize the lipid nanoparticles. In differential scanning calorimetry measurements, heating and cooling cycles are applied, and the resulting breakdown or fusion of the crystal lattice by heat exchange yields valuable information on lipid polymorphism and crystallinity as well as drug-lipid interactions. Differential scanning calorimetry analysis was complemented with $^1$H-NMR measurements to study the effect of tocotrienol-rich-fraction entrapment had on the solid-state of the nanostructured lipid carriers.

Initially bulk lipids and binary tocotrienol-rich-fraction/lipid mixtures were evaluated. Tocotrienol-rich-fraction-lipid binary mixtures were prepared by mixing the molten lipids with tocotrienol-rich-fraction at 85° C., which were then allowed to cool to room temperature (22-25° C.) prior to analysis. The three parameters evaluated in this study were fusion enthalpy, melting point, and onset of melting endotherm. Results from the evaluation are summarized in Table III below.

TABLE III

| Batch | Fusion enthalpy (J/g) | Melting endotherm (° C.) | Onset of melting endotherm (° C.) |
|---|---|---|---|
| Bulk CET | 203.4 ± 2.41 | 55.64 ± 2.02 | 53.36 ± 2.34 |
| 10% TRF-CET Binary mix | 182.3 ± 3.52 | 53.02 ± 1.89 | 51.49 ± 1.11 |
| 30% TRF-CET Binary mix | 134 ± 6.45 | 50.95 ± 1.32 | 49.59 ± 1.65 |
| 50% TRF-CET Binary mix | 82.54 ± 4.05 | 48.6 ± 1.02 | 45.59 ± 3.06 |
| Bulk-COMP | 107.6 ± 3.09 | 73.59 ± 2.07 | 71.0 ± 1.12 |
| 10% TRF-COMP Binary mix | 97.62 ± 2.37 | 71.63 ± 1.35 | 70.24 ± 1.27 |
| 30% TRF-COMP Binary mix | 84.65 ± 4.76 | 67.35 ± 1.26 | 65.94 ± 2.09 |
| 50% TRF-COMP Binary mix | 50.07 ± 2.98 | 63.17 ± 1.98 | 61.32 ± 1.43 |
| Bulk-PREC | 166.8 ± 1.87 | 61.82 ± 1.24 | 51.82 ± 1.45 |
| 10% TRF-PREC Binary mix | 113.4 ± 2.01 | 57.59 ± 1.56 | 49.12 ± 3.42 |
| 30% TRF-PREC Binary mix | 95.24 ± 3.92 | 55.02 ± 2.42 | 48.53 ± 2.13 |
| 50% TRF-PREC Binary mix | 70.16 ± 1.65 | 52.16 ± 1.45 | 46.6 ± 1.32 |
| Bulk-DYN | 198.5 ± 2.01 | 73.04 ± 1.23 | 70.73 ± 2.37 |
| 10% TRF-DYN Binary mix | 154.7 ± 1.63 | 71.17 ± 2.98 | 68.25 ± 2.14 |
| 30% TRF-DYN Binary mix | 133 ± 2.01 | 68.18 ± 1.78 | 66.98 ± 2.21 |
| 50% TRF-DYN Binary mix | 94.64 ± 1.49 | 65.72 ± 1.28 | 63.91 ± 2.22 |
| Bulk TRF | N/A* | N/A | N/A |

DSC measurements of bulk solid lipids, bulk TRF, and TRF-lipid binary (mean ± SD, n =3)
*N/A: Non applicable; bulk TRF does not show exothermic or endothermic event.

Not wishing to be bound by theory, the melting endotherm data coupled with the fusion enthalpy data suggest a change in the crystal order structure of solid lipid, which may be attributed to tocotrienol-rich-fraction entrapment in the case of nanostructured lipid carriers.

Figure 2A:
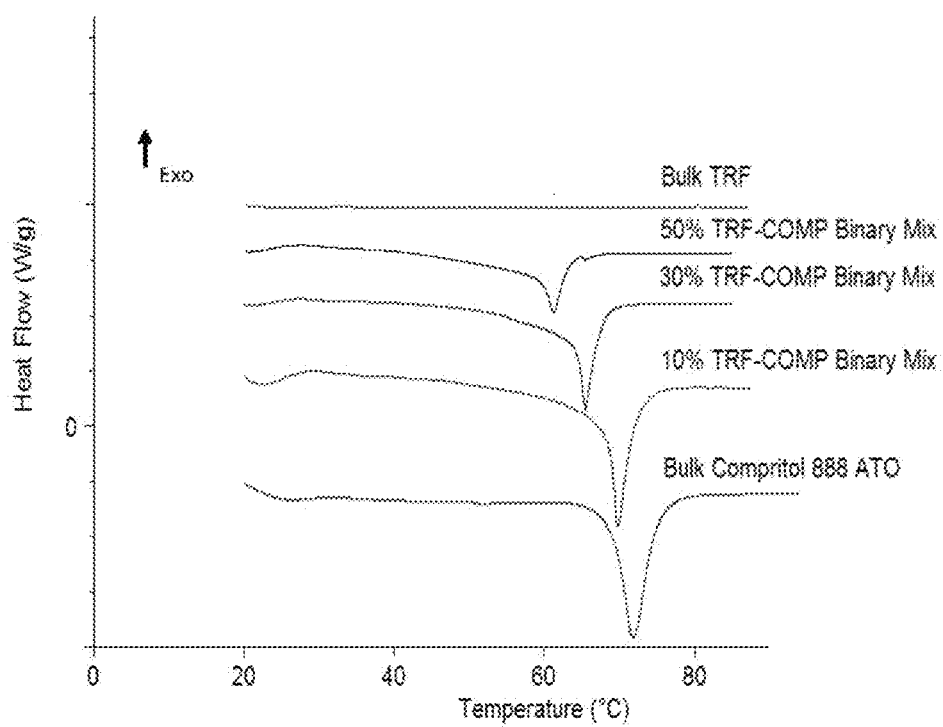
FIGS. 2A, 2B, 2C, and 2D show differential scanning calorimetry heating thermocalorimetric graphs of bulk lipids and binary mixtures of solid lipids containing 10%, 30%, and 50% tocotrienol rich fraction in glyceryl behenate (FIG. 2A); cetyl palmitate (FIG. 2B); glycerol tristearate (FIG. 2C); and glycerol palmitostearate (FIG. 2D)
Figure 2B:
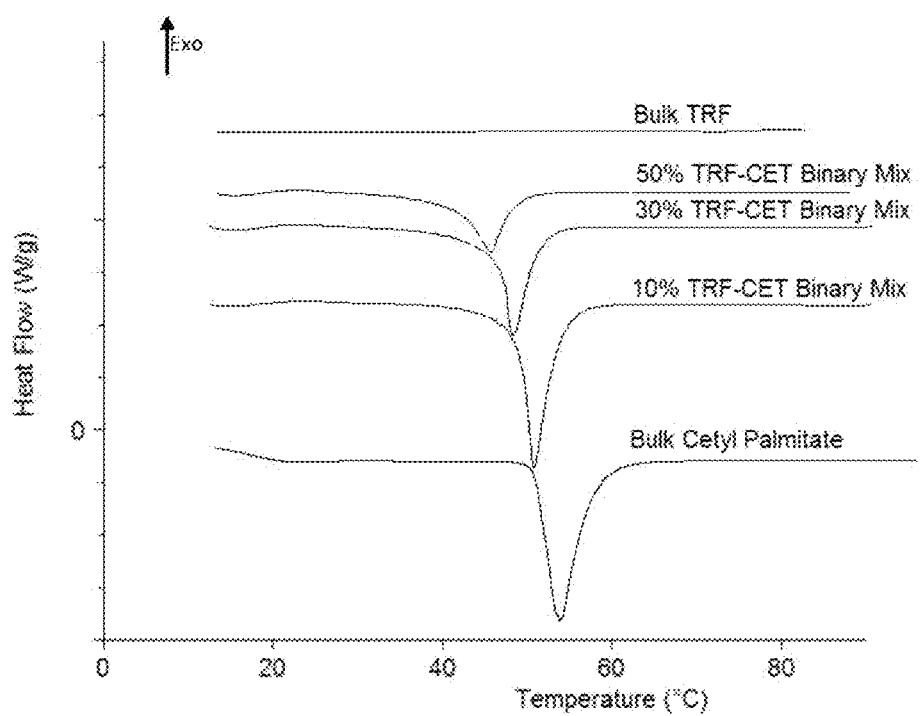
Figure 2C:
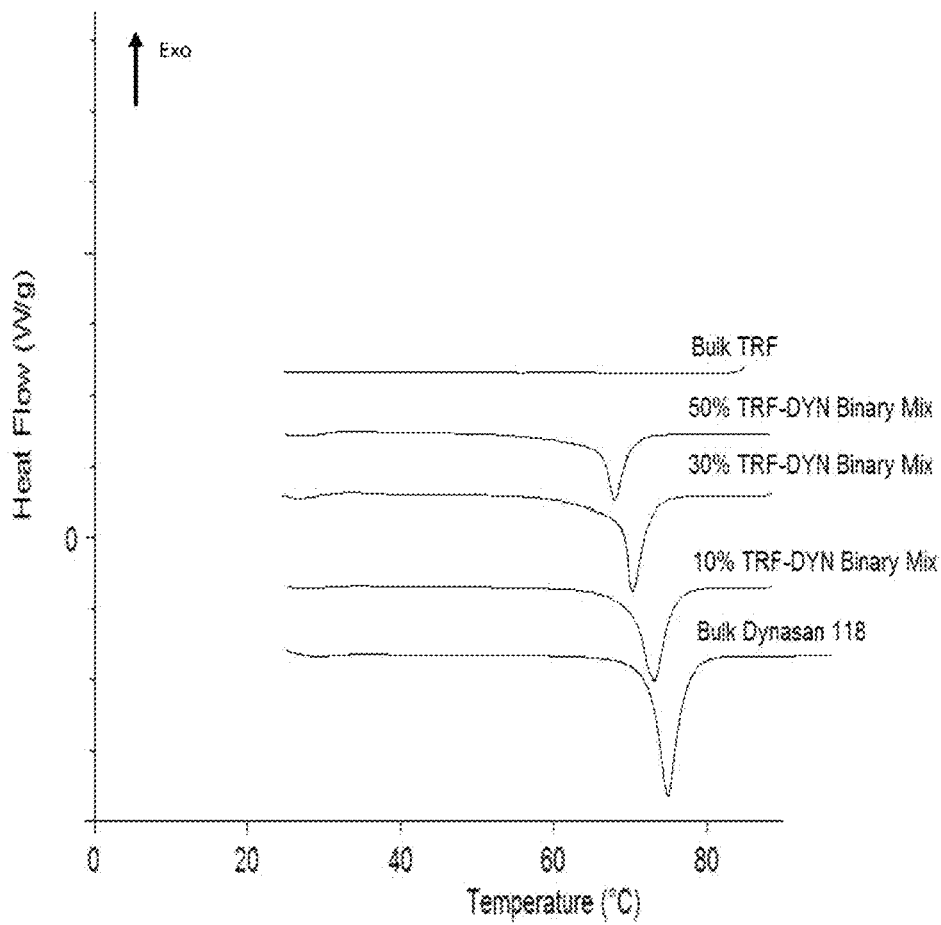
Figure 2D:
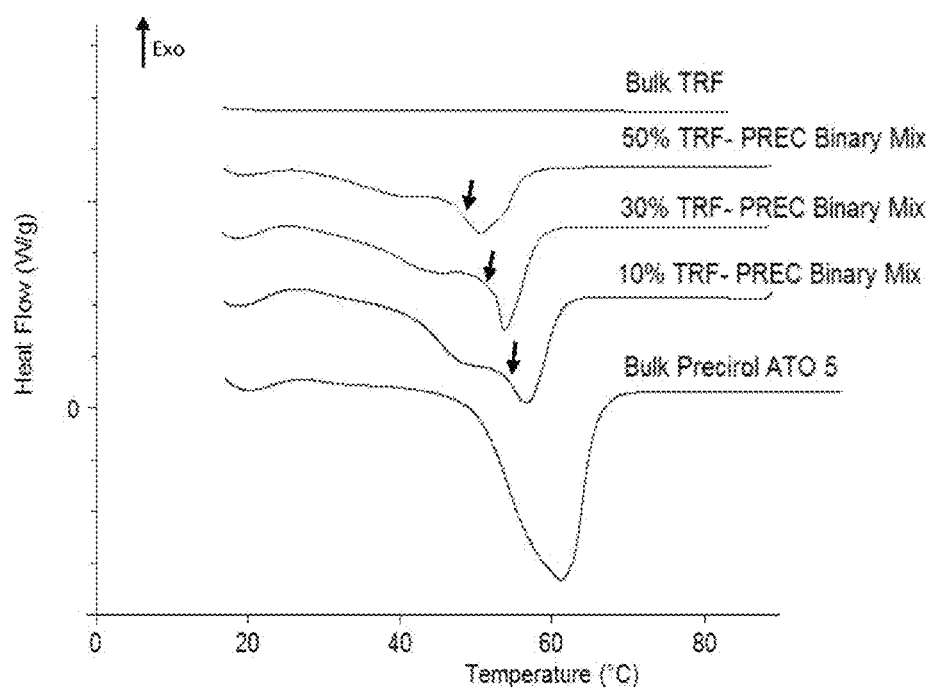

Differential scanning calorimetry thermoanalysis data of the bulk solid lipids are shown in Table III and in FIGS. 2A, 2B, 2C, and 2D. The melting point and fusion enthalpy of the bulk lipids were in the range from 55.64° C. (bulk cetyl palmitate) to 73.59° C. (bulk glyceryl behenate), and from 107.6 J/g (bulk glyceryl behenate) to 203.4 J/g (bulk cetyl palmitate) respectively. High melting points indicate that the lipids are good candidates for solid lipid nanoparticle and nanostructured lipid carrier formulation. High fusion enthalpy indicates strong bonding between the molecules of the crystal lattice. The melting point and fusion enthalpy of the lipids, however, decreased significantly ($p<0.0001$) with the addition of tocotrienol-rich-fraction as shown in the differential scanning calorimetry thermographs (FIGS. 1A, 1B and FIGS. 2A, 2B, 2C, and 2D) of the binary tocotrienol-rich-fraction/lipid blends. As shown in those figures, there was an inverse relationship between tocotrienol-rich-fraction concentration and both melting point and fusion enthalpy (FIGS. 2A and 2B). The linearity of the correlation was verified by linear regression analysis using the least squares method with the correlation coefficients shown in FIGS. 2A and 2B.

Subsequently, differential scanning calorimetry analysis was performed on solid lipid nanoparticles, nanostructured lipid carrier, and tocotrienol-rich-fraction-nanoemulsion, which were prepared by hot o/w microemulsion as described above. An analysis using differential scanning calorimetry analysis was carried out to study the interaction between tocotrienol-rich-fraction and the matrix forming lipids within the nanostructured lipid carriers by contrasting the data with date observed from the tocotrienol-rich-fraction/lipid binary blends. To ensure homogeneity of the formulations, visual observation revealed no particle growth, absence of agglomerates, and no evidence of phase separation.

The melting point and fusion enthalpy of solid lipid nanoparticles (FIGS. 1C, 1D, 3A, 3B, 3C, and 3D) were in the range from 53.6° C. (solid lipid nanoparticle-cetyl palmitate) to 72.6° C. (solid lipid nanoparticle-glyceryl behenate), and from 11.28 J/g (solid lipid nanoparticle-glyceryl behenate) to 21.72 J/g (solid lipid nanoparticle-cetyl palmitate), respectively. By contrasting these data with those observed for the bulk lipids, it could be seen that both parameters decreased when the lipid characteristics changed from bulk to aqueous colloidal nanodispersion. Furthermore, the endothermic melting peaks of solid lipid nanoparticles were broader when compared to the native solid lipids. The decrease in melting point may be attributed to the Kelvin effect. Not wishing to be bound by theory, the presence of surfactants, such as poloxamer 188, may decrease the interfacial tension and surface free energy between the solid lipid molecules and the surfactant solution resulting in an increase in the specific surface area and decrease in particle size, which in turn lowers the amount of energy required for the disruption and breakdown of the crystalline lipid matrix.

Similarly, the addition of tocotrienol-rich-fraction lowered the melting point and fusion enthalpy of the solid lipids in the nanostructured lipid carriers (FIGS. 2C, 2D and Table IV) when compared to the data generated for the tocotrienol-rich-fraction/lipid binary blends. The decrease in both melting point and fusion enthalpy linearly correlates to the increase in tocotrienol-rich-fraction concentration in the lipid phase from 10% to 50%. The effect of tocotrienol-rich-fraction on fusion enthalpy shown was in contrast to literature reports, including "Solid Lipid Nanoparticles (SLN) Based on Binary Mixtures of Liquid and Solid Lipids a (1)H-NMR Study" by V. Jenning, K. Mader and S. H. Gohla. Int J Pharm. 205:15-21 (2000) and "Characterization of a Novel Solid Lipid Nano-particle Carrier System Based on Binary Mixtures of Liquid and Solid Lipids" by V. Jenning, A. F. Thunemann, and S. H. Gohla, Int J Pharm, 199:167-177 (2000), in which liquid oil (migloyl 812; a medium chain triglyceride of capric/captylic acid) was shown to increase fusion enthalpy.

nanoparticles and nanostructured lipid carriers. These figures show that the re-crystallization temperature (peak) of the solid lipid nanoparticles was different from those observed after tocotrienol was added to the nanoparticles. This difference suggests that tocotrienol was successfully entrapped within the nanoparticles.

In addition to melting point and fusion enthalpies, pronounced supercooling may be observed when solid crystalline lipids are used for the preparation of solid lipid nanoparticles. Supercooling is the arithmetic difference between the endothermic melting peak and the onset of exothermic re-crystallization temperature. Supercooling has previously been attributed to the colloidal size of the lipid nanocrystals, which leads to crystallization of solid lipids at temperatures 2-3° C. below their melting point. This typically occurs when the preparation process is carried out by heating, such as during the preparation of solid lipid nanoparticle by hot o/w microemulsion methods. For solid lipid nanoparticles, the degree of supercooling ranged from about 6° C. for solid lipid nanoparticle-cetyl palmitate to about 42° C. for solid lipid nanoparticle-glycerol tristearate (FIGS. 4A, 4B, 4C, and 4D

TABLE IV

| Batch | Fusion enthalpy (J/g) | Melting temp. (° C.) | Onset of melting endotherm (° C.) | Recrystallization index (RI %) | Recrystallization temp. (° C.) | Supercooling* (° C.) |
|---|---|---|---|---|---|---|
| SLN-CET | 21.72 ± 2.5 | 53.64 ± 2.3 | 51.76 ± 2.2 | 106.78 | 47.88 | 5.76 ± 1.3 |
| NLC-CET-10 | 15.73 ± 1.9 | 52.48 ± 1.2 | 50.39 ± 1.7 | 77.66 | 46.59 | 5.89 ± 0.7 |
| NLC-CET-30 | 10.77 ± 2.3 | 50.89 ± 3.4 | 47.69 ± 3.6 | 56.26 | 44.85 | 6.04 ± 0.9 |
| NLC-CET-50 | 5.81 ± 4.5 | 48.14 ± 2.4 | 43.44 ± 1.2 | 35.20 | 36.86 | 11.28 ± 1.8 |
| SLN-COMP | 11.28 ± 1.4 | 72.58 ± 1.1 | 68.55 ± 1.1 | 104.83 | 65.23 | 7.35 ± 1.1 |
| NLC-COMP-10 | 6.54 ± 2.4 | 70.95 ± 2.1 | 64.83 ± 2.0 | 60.31 | 62.33 | 8.62 ± 1.5 |
| NLC-COMP-30 | 4.08 ± 3.4 | 67.38 ± 3.1 | 60.65 ± 3.9 | 33.71 | 55.45 | 11.93 ± 2.9 |
| NLC-COMP-50 | 1.77 ± 2.5 | 61.86 ± 1.5 | 54.44 ± 2.5 | 17.63 | 48.92 | 12.94 ± 3.0 |
| SLN-PREC | 12.24 ± 1.3 | 57.45 ± 1.4 | 50.3 ± 1.8 | 73.38 | 44.16 | 13.29 ± 1.3 |
| NLC-PREC-10 | 7.8 ± 2.1 | 53.94 ± 1.2 | 47.87 ± 1.1 | 61.87 | 41.49 | 12.45 ± 1.7 |
| NLC-PREC-30 | 5.76 ± 2.4 | 50.95 ± 1.4 | 43.6 ± 1.5 | 42.34 | 36.35 | 14.6 ± 3.6 |
| NLC-PREC-50 | 1.64 ± 1.3 | 47.72 ± 1.3 | 41.89 ± 2.4 | 11.69 | 33.05 | 14.67 ± 1.5 |
| SLN-DYN | 17.3 ± 2.1 | 69.91 ± 2.5 | 64.19 ± 1.5 | 87.15 | 28.1 | 41.91 ± 2.5 |
| NLC-DYN-10 | 14.33 ± 1.1 | 68.9 ± 2.1 | 65.09 ± 1.4 | 83.37 | 26.99 | 41.91 ± 1.9 |
| NLC-DYN-30 | 10.74 ± 1.2 | 67.01 ± 2.0 | 60.31 ± 1.4 | 56.53 | 23.22 | 43.79 ± 2.1 |
| NLC-DYN-50 | 7.64 ± 2.1 | 64.5 ± 2.1 | 57.08 ± 2.4 | 40.38 | 18.6 | 45.9 ± 2.1 |
| TRF-NEmu | N/A** | N/A | N/A | N/A | N/A | N/A |

DSC measurements of SLN, NLC, and TRF-NEmu (mean ± SD, n = 3)
*Supercooling: Arithmetic difference between melting endothermic temperature and the onset of exothermic recrystallization temperature.
**N/A: Non applicable; TRF-NEmu does not show exothermic or endothermic event.

Linear correlations between melting point and the loading of liquid lipid within nanostructured lipid carriers have been suggested to indicate a complete incorporation and/or entrapment of the liquid lipid within the solid matrix. The linearity of the correlations between melting point and fusion enthalpy with tocotrienol-rich-fraction concentrations were verified by linear regression analysis using least square method with the correlation coefficients showing on the graphs (FIGS. 1A, 1B, 1C, and 1D). The Recrystallization Index (RI, Table IV) of the solid lipid nanoparticles and nanostructured lipid carriers was measured to confirm tocotrienol-rich-fraction entrapment within the solid cores of the nanostructured lipid carriers. As implied by the data, RI decreased linearly with an increase in tocotrienol-rich-fraction concentration, which indicates a distortion in the crystal lattice of the solid lipids caused by the entrapped tocotrienol-rich-fraction. This effect was apparent in the sudden and sharp decrease in RI when 50% of the solid lipids were displaced by tocotrienol-rich-fraction as compared to the RI of the tocotrienol-rich-fraction-free solid lipid nanoparticles.

FIGS. 4A, 4B, 4C, and 4D show the differential scanning calorimetry cooling thermocalorimetric graphs of solid lipid and Table IV). Therefore, cooling of the solid lipid nanoparticles should be carefully monitored and adjusted to ensure complete solidification of the lipids, particularly when lipids such as glycerol palmitostearate and glycerol tristearate that impart a high degree of supercoolong are used. Incorporating tocotrienol-rich-fraction within solid lipid nanoparticles further increased the degree of supercooling. However, the increase in supercooling with tocotrienol-rich-fraction addition was only significant (p<0.01) in the case of nanostructured lipid carriers made from cetyl palmitate and glyceryl behenate, which initially exhibited a relatively low degree of supercooling when formulated as tocotrienol-rich-fraction-free solid lipid nanoparticles. The increase in the degree of supercooling was insignificant for nanostructured lipid carriers made from glycerol palmitostearate and glycerol tristearate, which may be due to the pronounced effect of the raw lipids on supercooling.

Figure 3A:
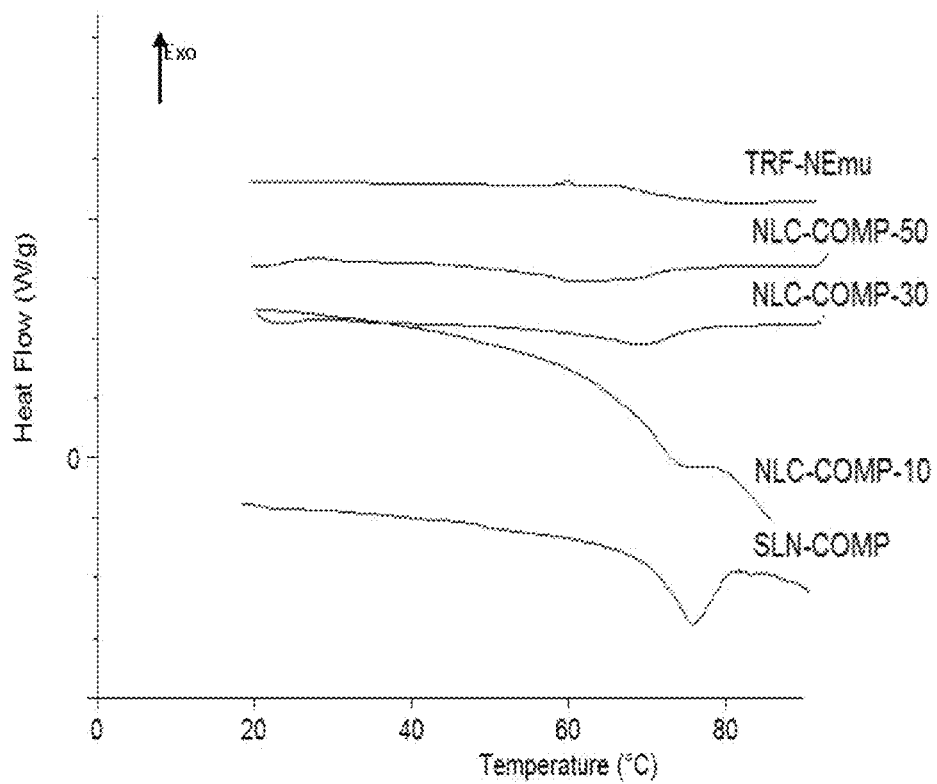
FIGS. 3A, 3B, 3C, and 3D show differential scanning calorimetry heating thermocalorimetric graphs of solid lipid nanoparticles and nanostructured lipid carriers containing 10%, 30%, and 50% tocotrienol rich fraction loads in glyceryl behenate (FIG. 3A), cetyl palmitate (FIG. 3B), glycerol tristearate (FIG. 3C), and glycerol palmitostearate (FIG. 3D)
Figure 3B:
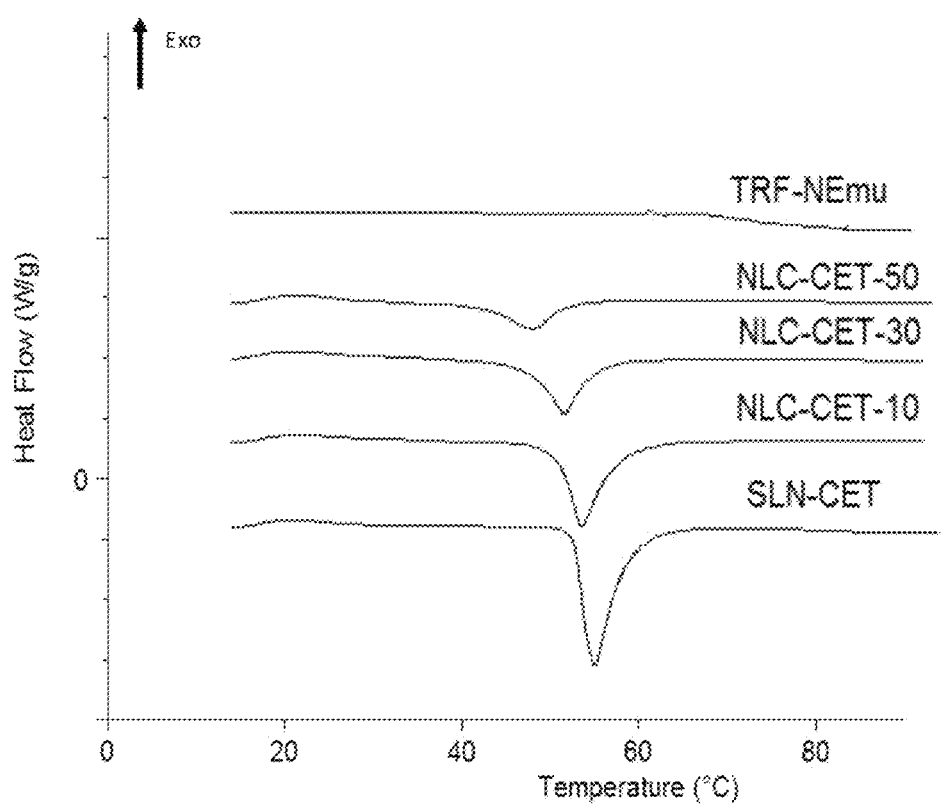
Figure 3C:
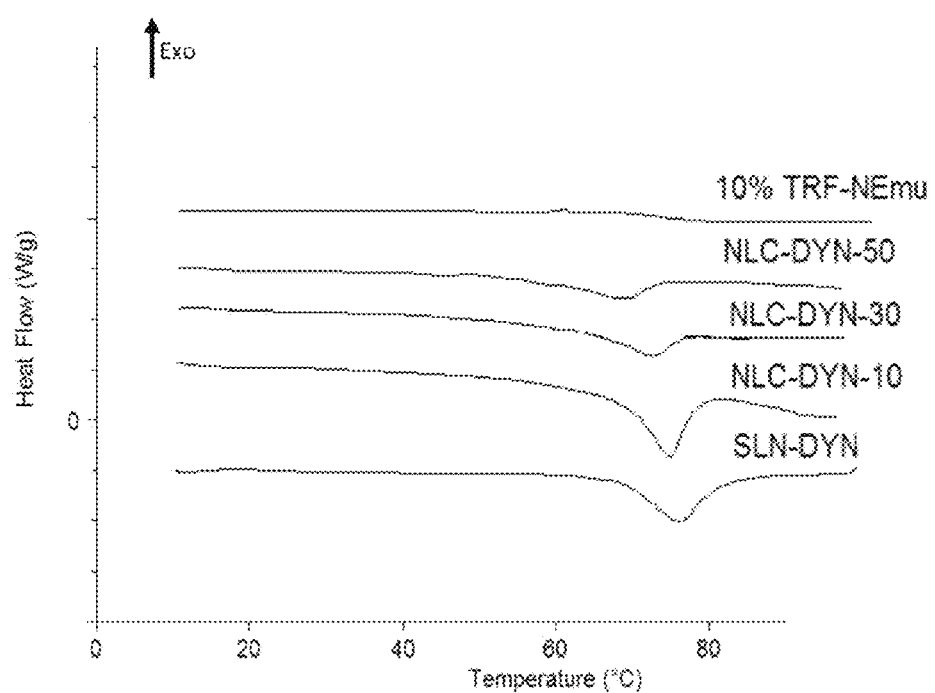
Figure 3D:
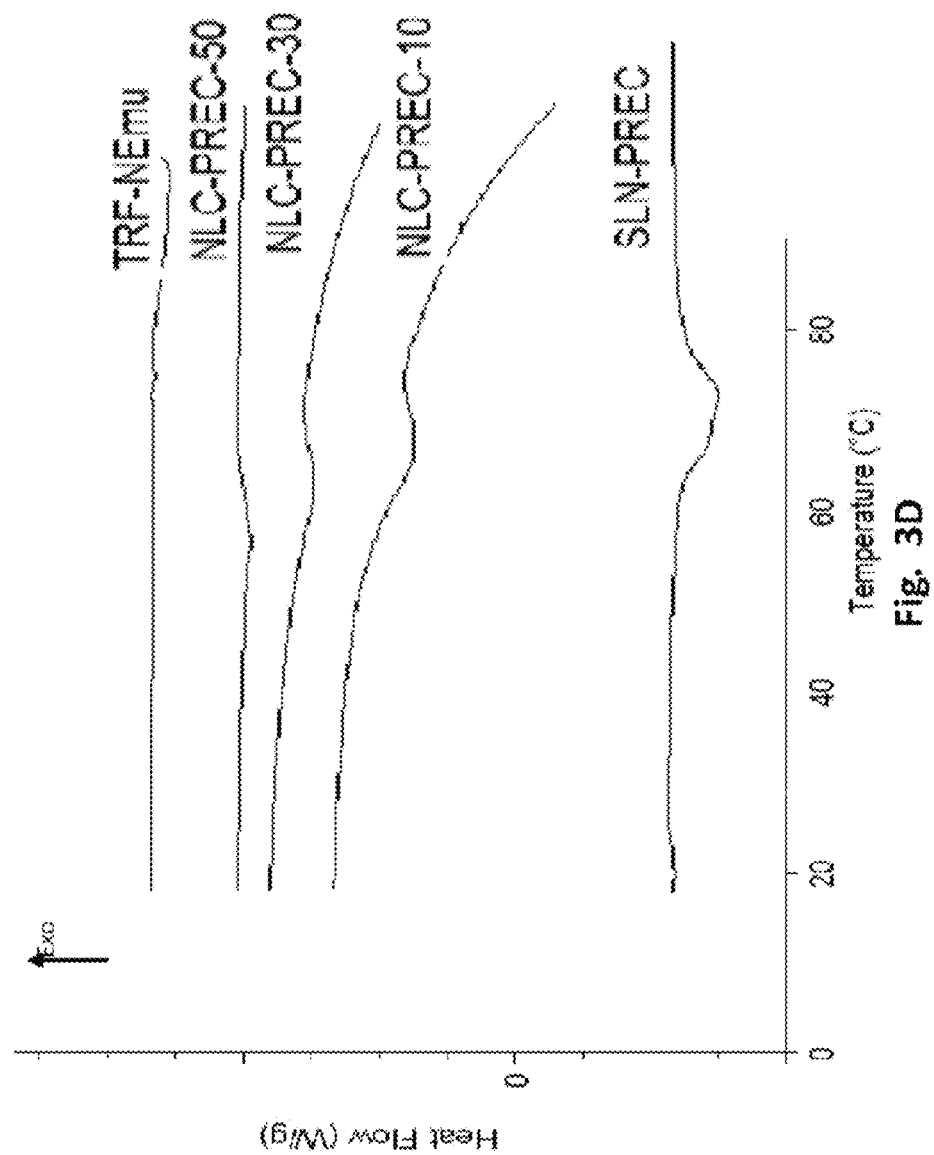
Figure 4A:
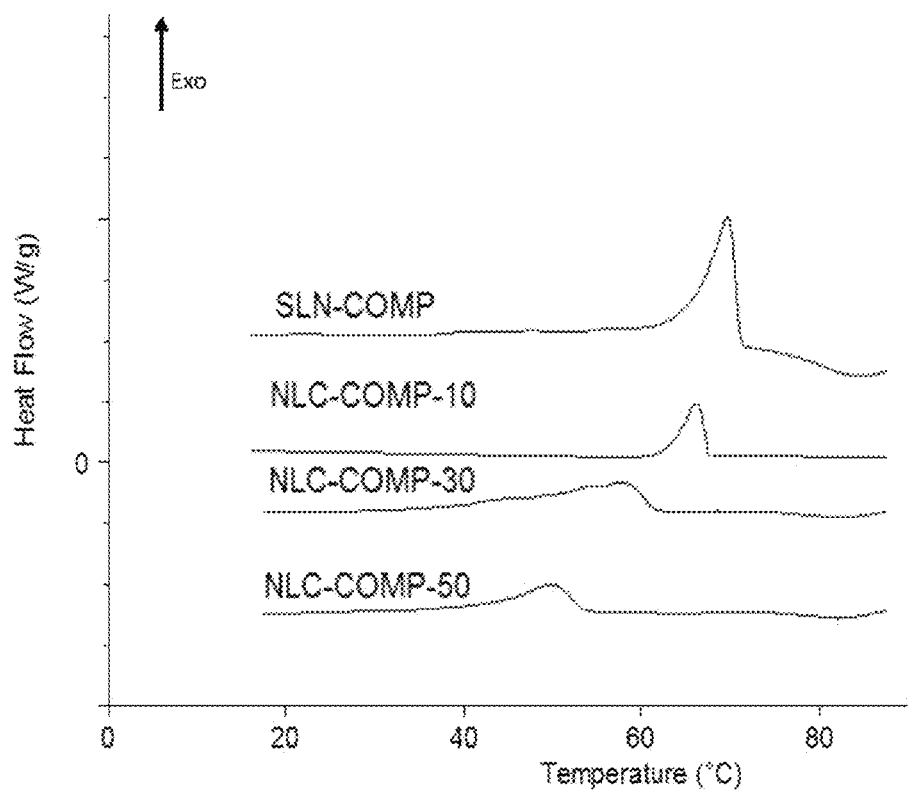
FIGS. 4A, 4B, 4C, and 4D show differential scanning calorimetry cooling thermocalorimetric graphs of solid lipid nanoparticles and nanostructured lipid carriers containing 10%, 30%, and 50% tocotrienol rich fraction loads in glyceryl behenate (FIG. 4A), cetyl palmitate (FIG. 4B), glycerol tristearate (FIG. 4C), glycerol palmitostearate (FIG. 4D)
Figure 4B:
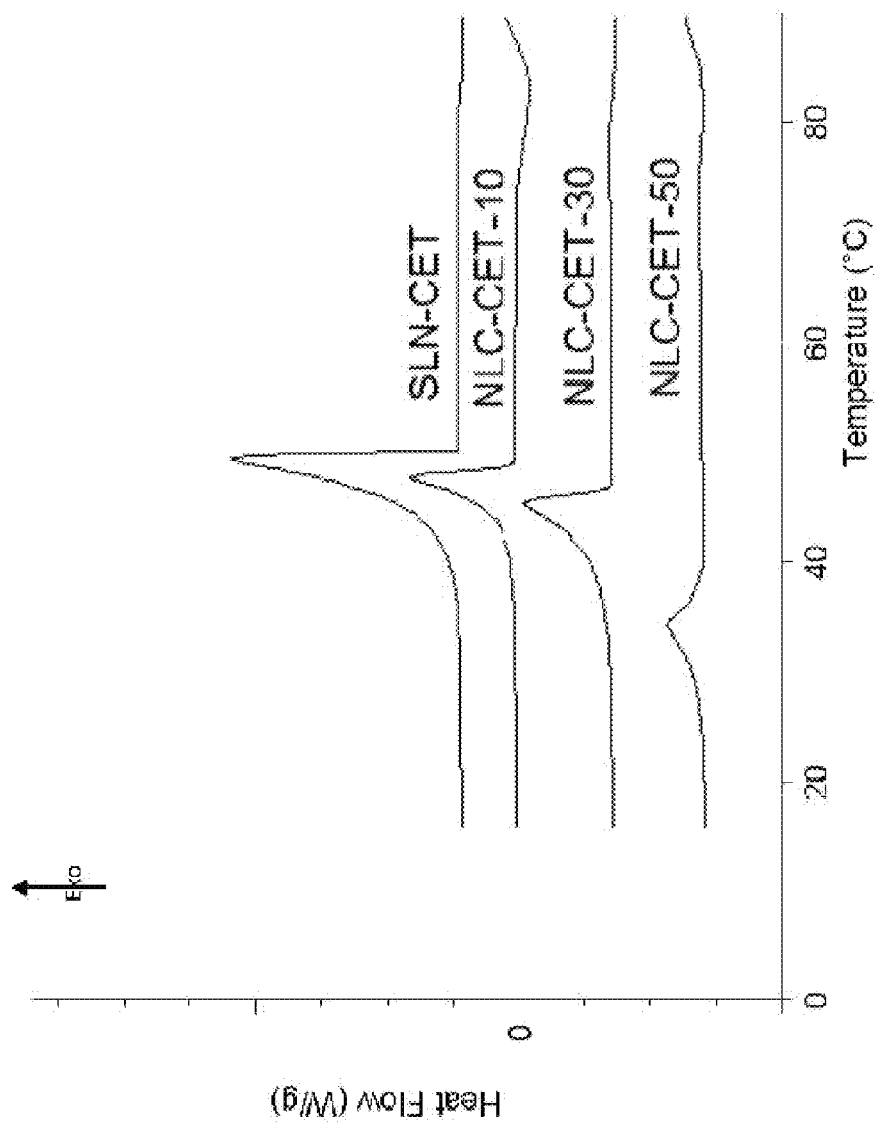
Figure 4C:
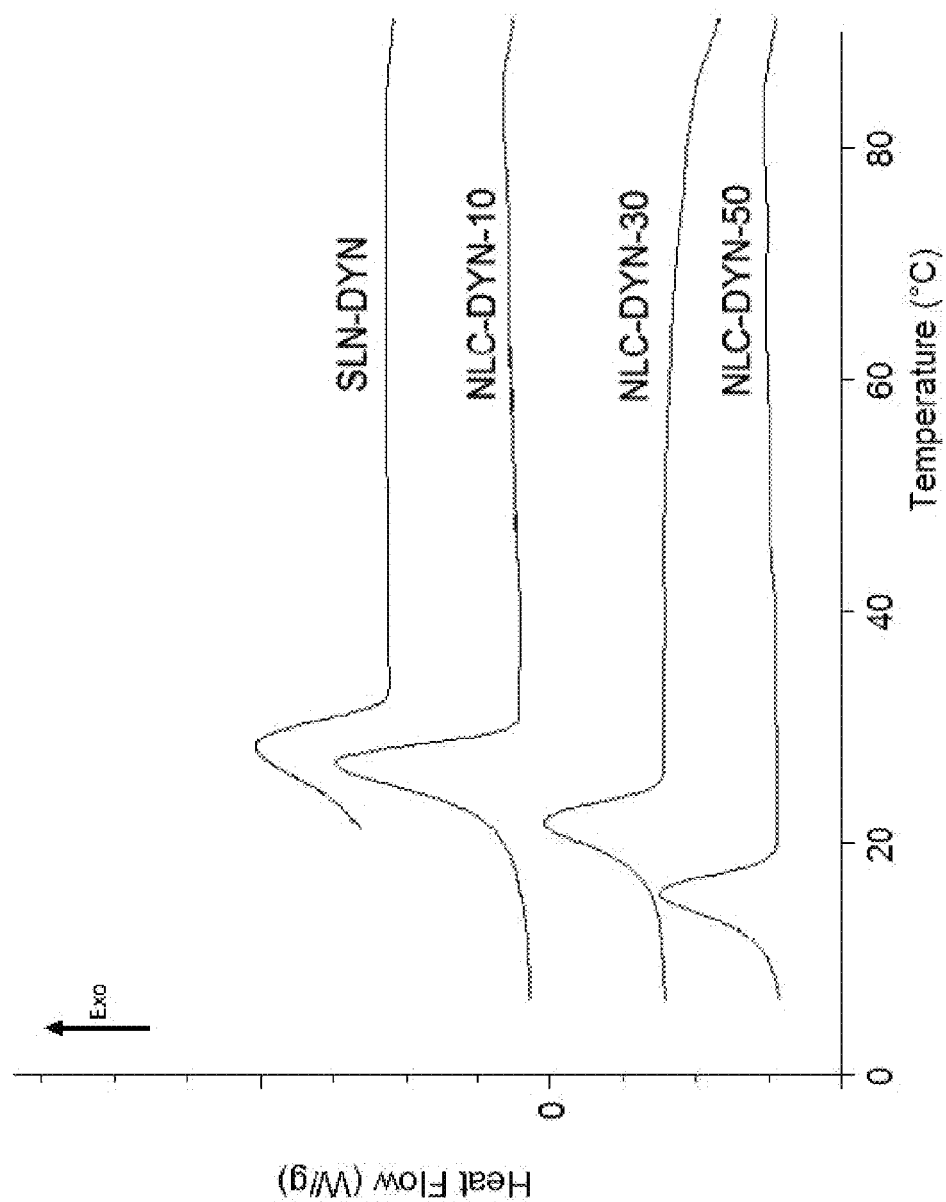
Figure 4D:
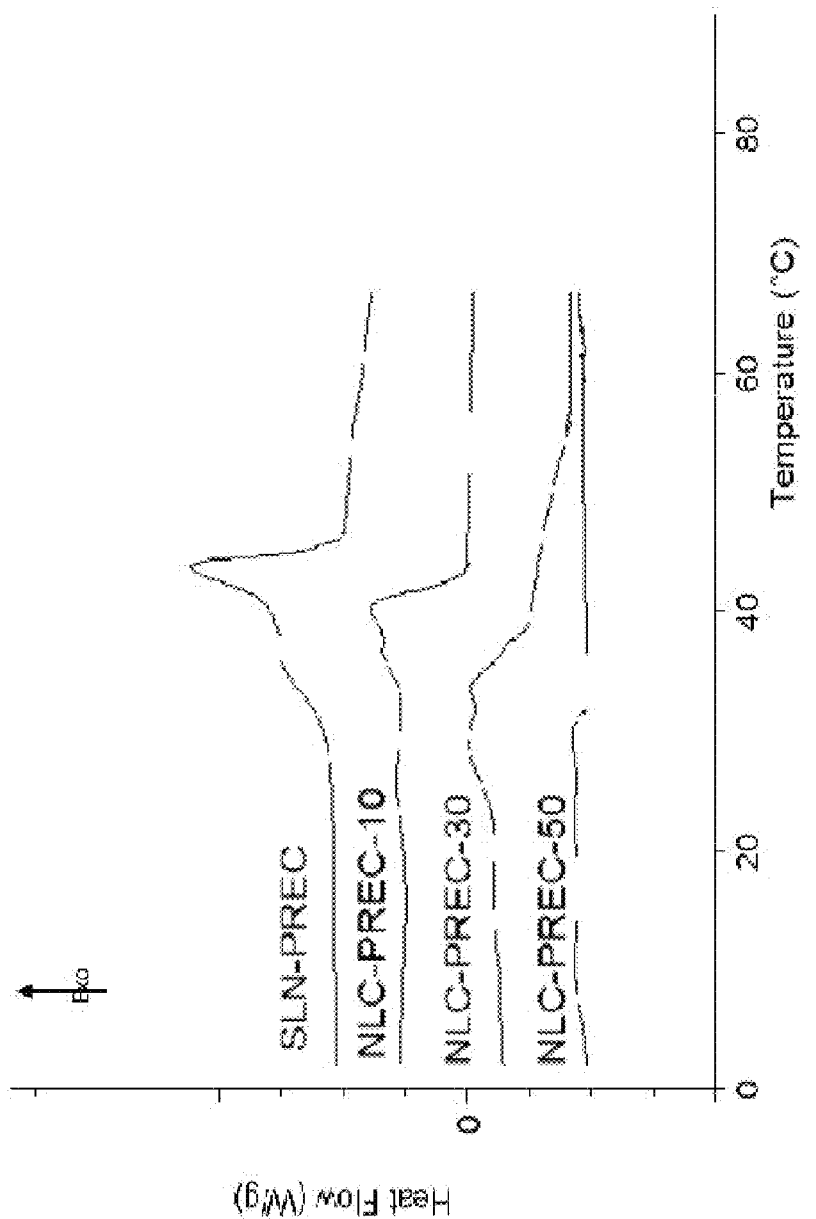

The shoulder appearing beside the main glycerol palmitostearate endothermic peak (indicated by arrows in FIG. 2D) is due to polymorphic transition or melting of other polymorphs present in glycerol palmitostearate. The intensity of this shoulder, however, decreased when glycerol palmitostearate was formulated as a solid lipid nanoparticle or nanostructured lipid carrier (FIG. 3D). The decrease in shoulder intensity could be attributed to the presence of surfactants and tocotrienol-rich-fraction in the solid lipid nanoparticle and nanostructured lipid carrier dispersions. Presence of poloxamer 188 and tocotrienol-rich-fraction may have decreased glycerol palmitostearate crystallization and polymorphic transition at higher temperatures during solid lipid nanoparticle and nanostructured lipid carrier preparation. The decrease in both crystallization and polymorphic transition may be attributed to a decrease in particle size brought by poloxamer 188 and/or tocotrienol-rich-fraction addition (Table II). However, the observed effect of particle size is in contrast to effects previously reported, which suggested that an increase in polymorphic transition of lipids with a consequent increase in shoulder intensity was accelerated by a decrease in particle size. See "Thermoanalysis of the Recrystallization Process of Melt-homogenized Glyceride Nanoparticles" by B. Siekmann and K. Westesen, Colloids Surf B. 3:159-175 (1994) and "Crystallization Tendency and Polymorphic Transitions in Triglyceride Nanoparticle" by H. Bunjes, K. Westesen, and M. H. J. Koch. Int J Pharm. 129:159-173 (1996). Similarly, in contrast to those same previous reports, solid lipid nanoparticle-glyceryl tristearate and solid lipid nanoparticle-glyceryl behenate did not display a peak that corresponds to their α-polymorph even after reheating of the crystallized solid lipid nanoparticles in a second differential scanning calorimetry run.

Example 1(D)

$^1$H-NMR $^1$H-NMR studies were performed to further elucidate the mode of tocotrienol-rich-fraction entrapment within nanostructured lipid carriers and to investigate whether tocotrienol-rich-fraction-poloxamer emulsion might have been formed as a byproduct during the preparation of nanostructured lipid carriers. These studies were based on the assumption that the width of the signals appearing in the liquid-state NMR profile is a reflection of the fluidity of the particles dispersed in the medium. Fluid liquid-like materials, such as tocotrienol-rich-fraction, generate characteristic narrow band signals with high amplitude. On the other hand, dispersed solid molecules, such as solid lipid nanoparticles, shorten the relaxation time and display broad signals with small amplitude, which may be attributed to their restricted mobility. Therefore, tocotrienol-rich-fraction entrapment within nanostructured lipid carriers was expected to generate signals of different amplitudes and widths, depending on tocotrienol-rich-fraction proportion and its interaction with the solid lipids.

Figure 5:
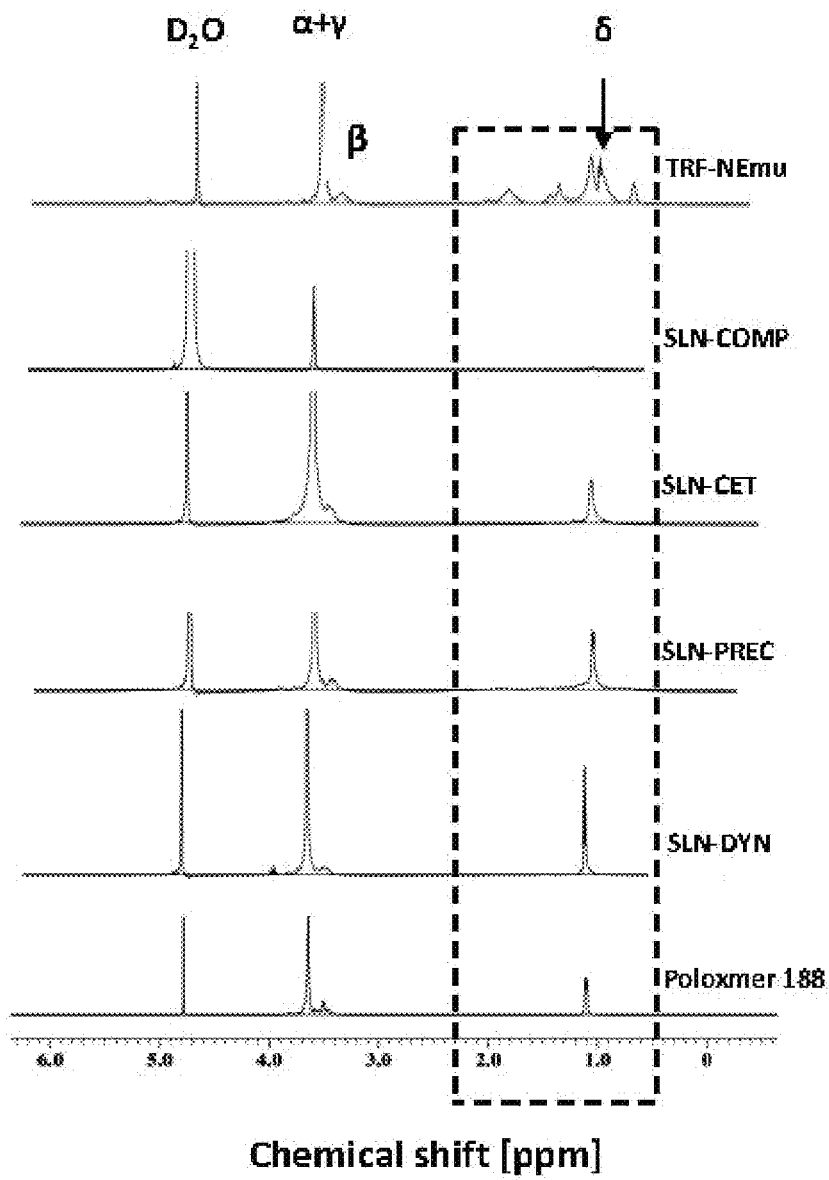
FIG. 5 shows a Full $^1$H-NMR spectra of poloxamer 188 solution, tocotrienol rich fraction nanoemulsion, and solid lipid nanoparticles made from glycerol tristearate, glycerol palmitostearate, cetyl palmitate, and glyceryl behenate.
Figure 6A:
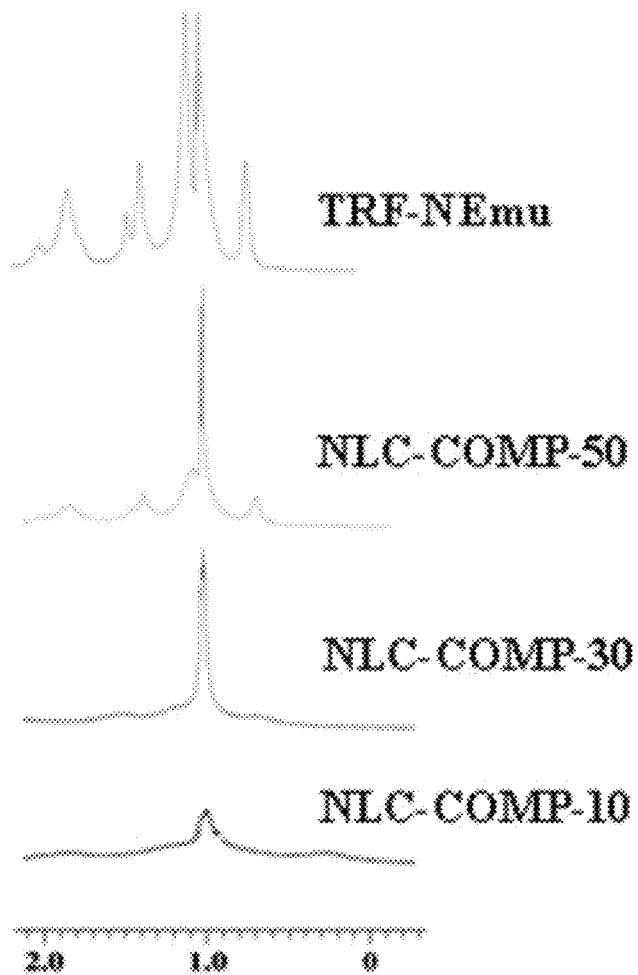
FIGS. 6A, 6B, 6C, and 6D show $^1$H-NMR spectra showing identifiable signals in the range of 0-2.2 ppm of nanostructured lipid carriers made from glyceryl behenate (FIG. 6A), cetyl palmitate (FIG. 6B), glycerol tristearate (FIG. 6C), and glycerol palmitostearate (FIG. 6D)
Figure 6B:
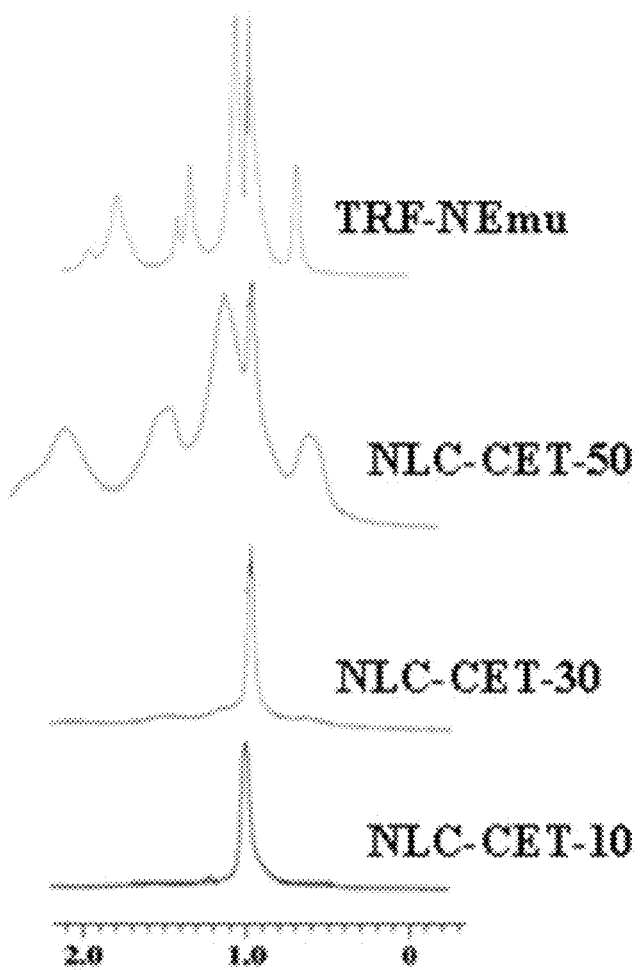
Figure 6C:
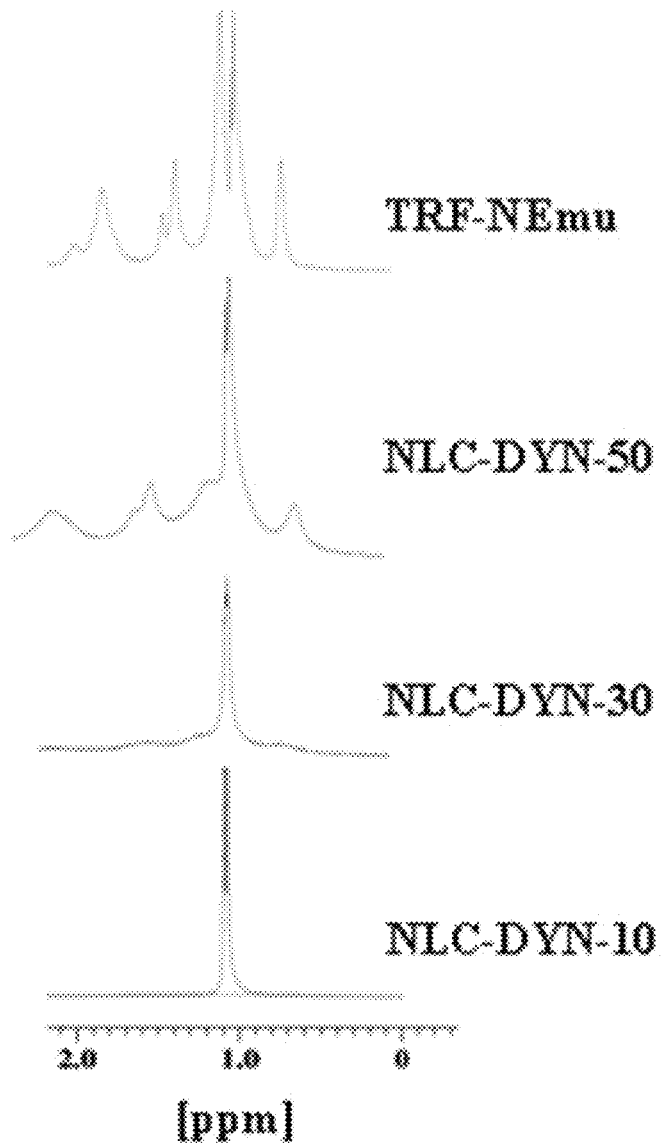
Figure 6D:
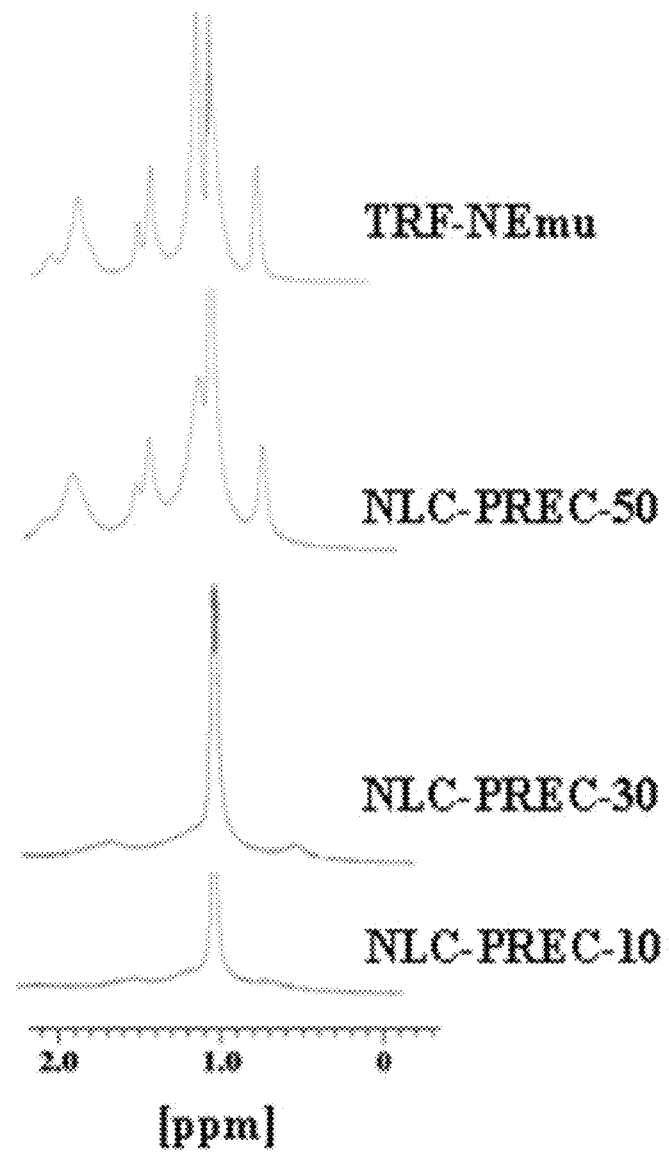

The nanodispersions under investigation (Table II) were analyzed as described in the experimental section. Initially the $^1$H-NMR spectra of the colloidal solid lipid nanoparticle formulations (solid lipid nanoparticle-cetyl palmitate, solid lipid nanoparticle-glyceryl behenate, solid lipid nanoparticle-glycerol tristearate, and solid lipid nanoparticle-glycerol palmitostearate) and the aqueous poloxamer solution were generated (FIG. 5). Although solid lipid nanoparticles were prepared from different lipids, the signals in the complex colloidal mixtures were comparable to those of the poloxamer aqueous solution, i.e., they appeared at the same chemical shift. The major signal at 4.81 ppm is for the deuterated water, which was used as the dispersion medium during the preparation of the nanoparticles. Three distinguishable signals were attributed to poloxamer 188 (FIG. 5); at 3.63 ppm (α,γ-H of poloxamer 188, brs), 3.55 ppm (β-H, integrated for one proton, multiplet), and 1.11 ppm (δ-H, integrated for three protons, doublet). Therefore, for the solid lipid nanoparticle samples, only poloxamer-derived signals, but no solid lipid-related signals were observed. The absence of NMR signals from the triglycerides in the solid lipid nanoparticle colloidal mixtures was expected due to the very short relaxation times associated with the solid ingredients, which can not be detected using liquid-state NMR. These findings suggest complete crystallization of the solid lipids and the absence of supercooled melts in the dispersions.

Nanostructured lipid carriers containing tocotrienol-rich-fraction were analyzed by $^1$H-NMR. To facilitate the assignment of tocotrienol-rich-fraction signals in the complex nanostructured lipid carriers mixtures, $^1$H-NMR signals of tocotrienol-rich-fraction-nanoemulsion were first analyzed and compared to those of the solid lipid nanoparticles and the aqueous poloxamer solution (FIGS. 6A, 6B, 6C, and 6D). Within the range from 2.2 to 5.0 ppm, it was observed that the solid lipid nanoparticles of the four lipids, tocotrienol-rich-fraction-nanoemulsion, and the aqueous poloxamer solution produced identical signals at 4.81 for deuterated water and at 3.63 and 3.55 for poloxamer protons. Nonetheless, the distinct signals in the 0.0-2.1 ppm range (Table V)—with the exception of the poloxamer signal at 1.11 ppm—were attributed to methyl signals of tocotrienol-rich-fraction components. Literature values for tocopherols and tocotrienols facilitated the assignment of tocotrienol-rich-fraction protons.

TABLE V

| Chemical shift (ppm) | Proton assignment/tocotrienol and tocopherol components of TRF |
|---|---|
| 2.11 | One benzylic $CH_3$ protons (C-8-$CH_3$) |
| 1.93 | Two benzylic $CH_3$ protons (C-5-$CH_3$ & C-7-$CH_3$) |
| 1.55 | Two allylic $CH_3$ protons (C-12a and 12'b-$CH_3$) |
| 1.47 | Two $CH_3$ protons (C-4'-$CH_3$ & C-8'-$CH_3$) |
| 1.18 | One $CH_3$ (C-2-$CH_3$) |

$^1$H-NMR assignment of TRF signals*
*These assignments are based on literature reports.

Once the tocotrienol-rich-fraction signals were identified, the nanostructured lipid carriers were analyzed by $^1$H-NMR. The $^1$H-NMR spectra of the tocotrienol-rich-fraction-nanoemulsion and the nanostructured lipid carriers, which reveal tocotrienol-rich-fraction asymmetric signals are shown in FIGS. 6A, 6B, 6C, and 6D. As expected, the protons' chemical shift did not change with a change in tocotrienol-rich-fraction loading. However, the tocotrienol-rich-fraction-nanoemulsion showed well-resolved sharp signals when compared to the broad lines of the nanostructured lipid carriers at 50% tocotrienol-rich-fraction load. The broadening of the lines could be attributed to the restricted mobility of the tocotrienol-rich-fraction in the nanostructured lipid carriers when compared to the fluid and less viscous tocotrienol-rich-fraction-nanoemulsion. At low tocotrienol-rich-fraction load (10%), tocotrienol-rich-fraction signals attenuated and eventually disappeared when 90% of the nanostructured lipid carrier core was displaced by solid lipids even with the use of long acquisition time (128 scans). Peak loss may be attributed to the strength of tocotrienol-rich-fraction interaction with the solid lipids within the matrix, which was reflected on the relaxation times of tocotrienol-rich-fraction protons, reducing detectability by NMR.

To confirm the entrapment of tocotrienol-rich-fraction within the solid matrix of the nanostructured lipid carriers and the absence of free tocotrienol-rich-fraction-poloxamer emulsion tocotrienol-rich-fraction-free solid lipid nanoparticles were physically mixed with tocotrienol-rich-fraction-nanoemulsion and analyzed by NMR. Line width and intensity of the tocotrienol-rich-fraction component-protons were observed in $^1$H-NMR spectra of the physical mixture (data not shown) and found to be superimposed to those observed with tocotrienol-rich-fraction-nanoemulsion (FIGS. 6A, 6B, 6C, and 6D). These results eliminated the possibility of tocotrienol-rich-fraction hydrophobic interaction with solid lipid nanoparticles in the physical mixture, which would have had a negative effect on tocotrienol-rich-fraction signal amplitude. In contrast, the tocotrienol-rich-fraction proton signals in nanostructured lipid carrier samples had lower signal amplitudes and broader lines, which could be attributed to a strong interaction between the tocotrienol-rich-fraction molecules and the solid lipids and suggests tocotrienol-rich-fraction immobilization and localization within the solid glyceride and tenside layer of the solid lipids. The extent of tocotrienol-rich-fraction immobilization in nanostructured lipid carriers was quantified by measuring the widths, at half height, of tocotrienol-rich-fraction signal amplitude. Reduction in the tocotrienol-rich-fraction concentration in the nanostructured lipid carrier formulations broadened the peaks (Table VI). Some of the tocotrienol-rich-fraction protons, however, exhibited an extensive peak broadening that rendered measurement at half-amplitude impossible. This was particularly evident in nanostructured lipid carrier formulations with 10% tocotrienol-rich-fraction loads, which were therefore not reported in Table VI.

TABLE VI

| | $^1$H-NMR line width at half amplitude of TRF protons [Hz]* | | | | |
|---|---|---|---|---|---|
| Formulation | C-8 CH$_3$ | C-5 & C-7 CH$_3$ | C-12a & C-12'b-CH$_3$ | C-4' & C-8' CH$_3$ | C-2 CH$_3$ |
| TRF-NEmu | 29.57 | 38.4 | 10.39 | 13.44 | 17.9 |
| NLC-CET-30 | — | 63.64 | — | 15.58 | — |
| NLC-CET-50 | — | 54.88 | — | 15.52 | — |
| NLC-COMP-30 | — | 59.4 | — | 15.12 | — |
| NLC-COMP-50 | — | 44.54 | — | 13.79 | — |
| NLC-PREC-30 | — | 59.24 | — | 21.68 | — |
| NLC-PREC-50 | — | 46.54 | — | 14.31 | — |
| NLC-DYN-30 | — | 59.76 | — | 21.68 | — |
| NLC-DYN-50 | — | 57.76 | — | 14.31 | — |

Widths at half height of TRF $^1$H-NMR signal amplitude (values indicated by — represents extensive peak broadening with difficulty in peak width measurement. In NLC-10 complete signal loss took place)
*The unit is expressed in Hz = width [ppm] × 400.

Figure 7:
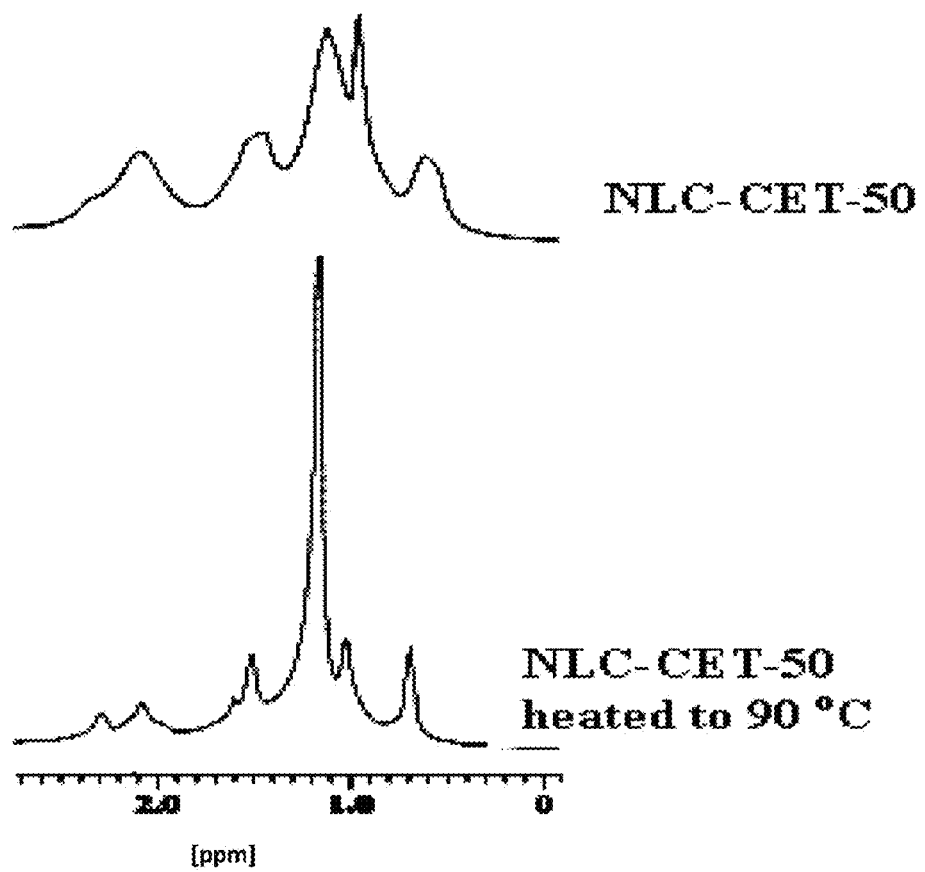
FIG. 7 shows $^1$H-NMR spectra of NLC-CET-50, showing influence of heat on peak amplitude.

To demonstrate the relationship between signal intensity and tocotrienol-rich-fraction mobility, the $^1$H-NMR spectrum for nanostructured lipid carrier-cetyl palmitate, which had the lowest melting point of the four lipids, was acquired at 90° C. Heating nanostructured lipid carriers above their melting points reverts them to their fluid microemulsion state. The unique tocotrienol-rich-fraction C-2 methyl signal at 1.18 ppm became narrower and had a sharper intensity when compared to the same C-2 methyl signal of tocotrienol and tocopherol components of nanostructured lipid carrier-cetyl palmitate formulations when measured at room temperature (FIG. 7). Similar results were obtained for the other lipids (glyceryl behenate, glycerol tristearate, and glycerol palmitostearate). Not wishing to be bound by theory, this observation is likely attributed to the increase in mobility of the C-2 methyl protons of the tocotrienol-rich-fraction components induced by heating with a subsequent decrease in hydrophobic interaction with the solid lipid matrix.

Figure 8A:
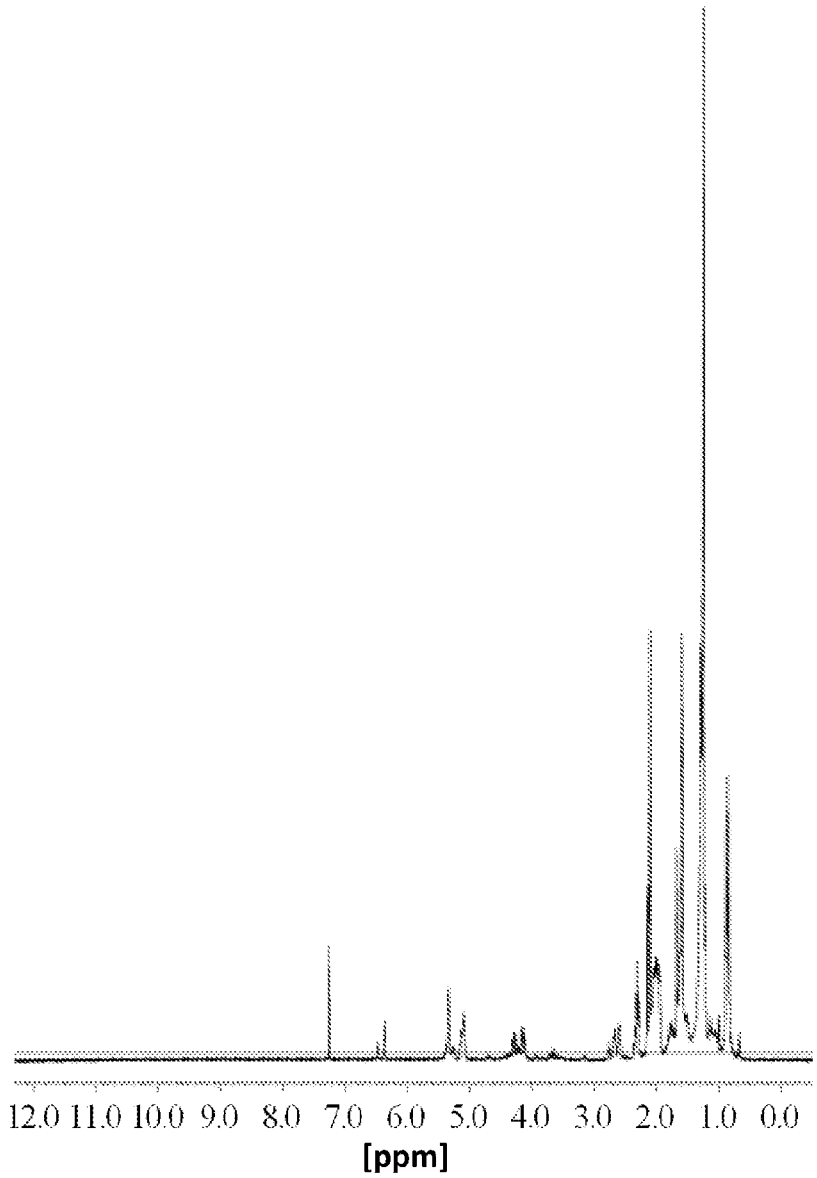
FIGS. 8A, 8B, 8C, and 8D show $^1$H-NMR graphs of tocotrienol rich fraction in $CD_3Cl$ (FIG. 8A), glycerol tristearate in $CD_3Cl$ (FIG. 8B), chloroform layer after extraction (FIG. 8C), and supernatant aqueous layer after extraction (FIG. 8D). Solid arrows represent proton signals of tocotrienol rich fraction, and dashed arrows represent overlapped proton signals of the methyl groups of tocotrienol rich fraction and glycerol tristearate.
Figure 8B:
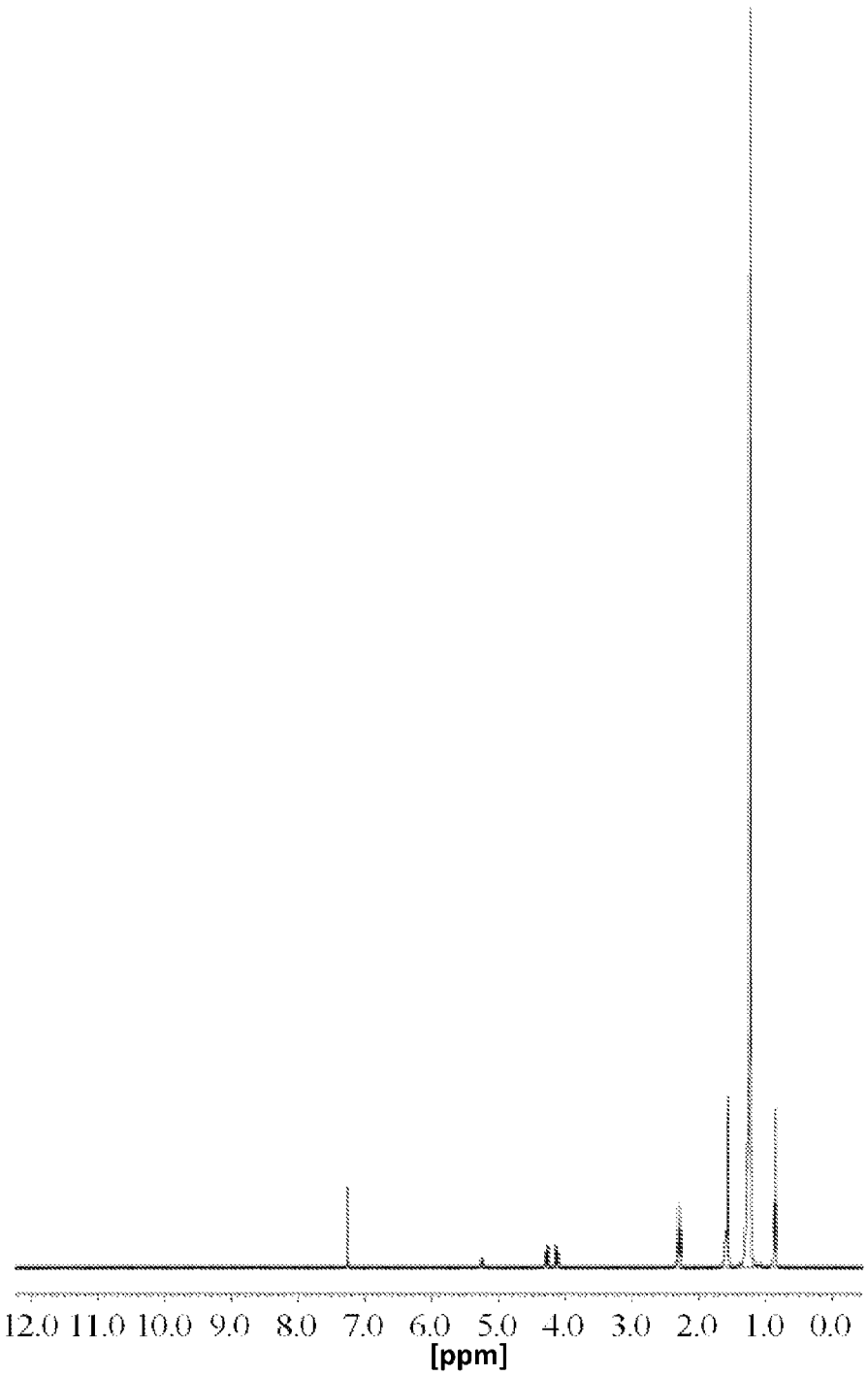
Figure 8C:
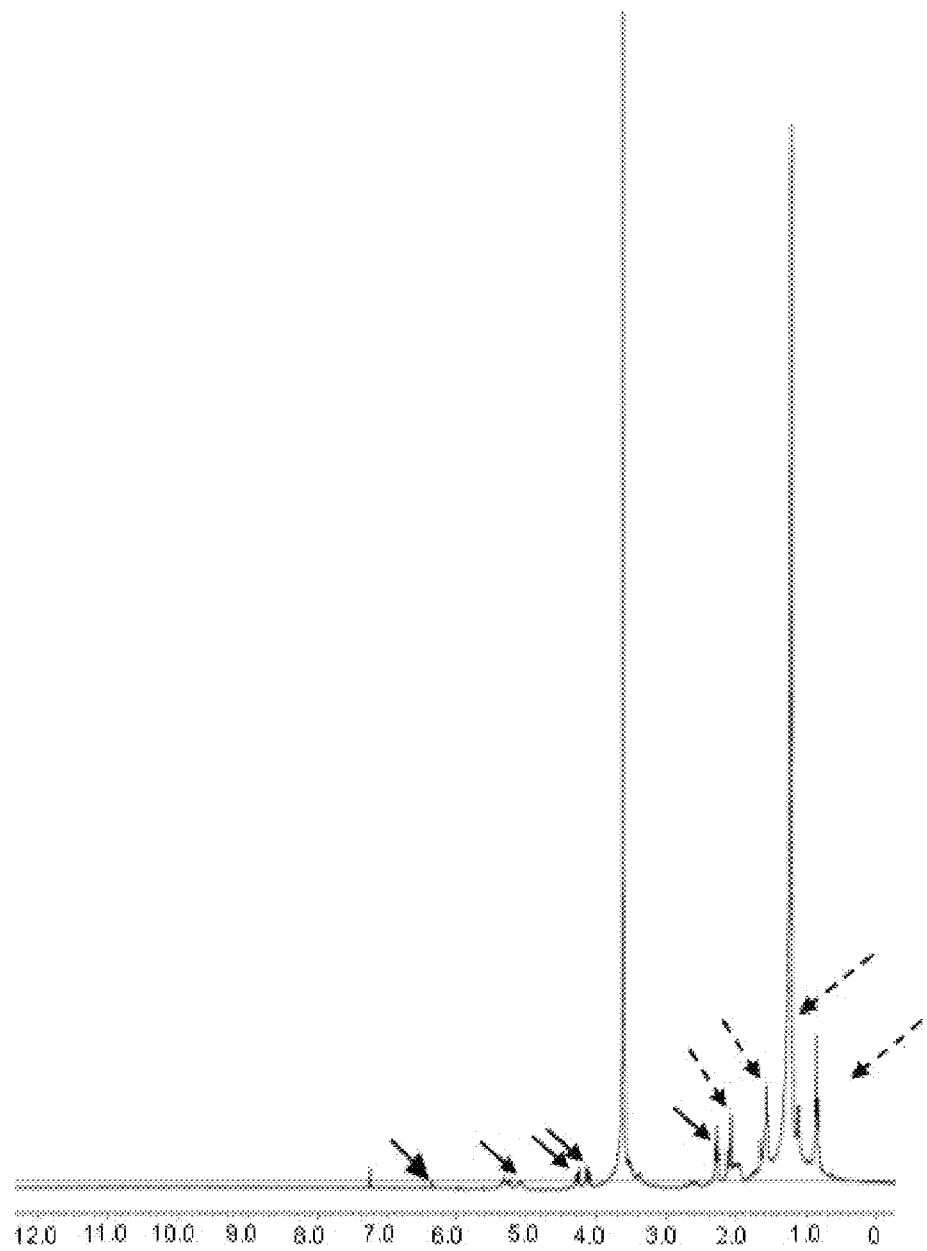
Figure 8D:
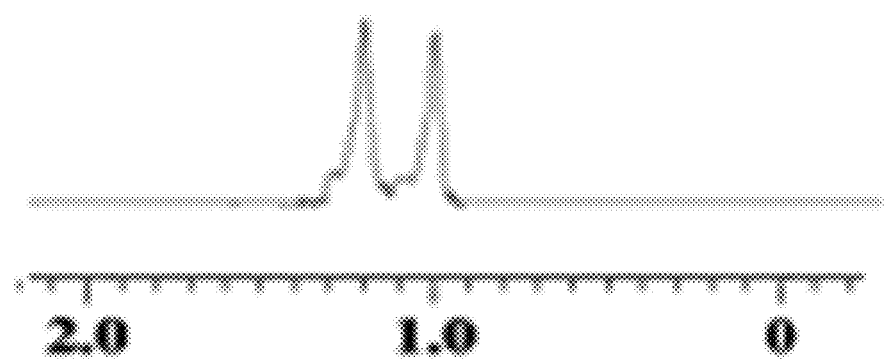
Figure 9A:
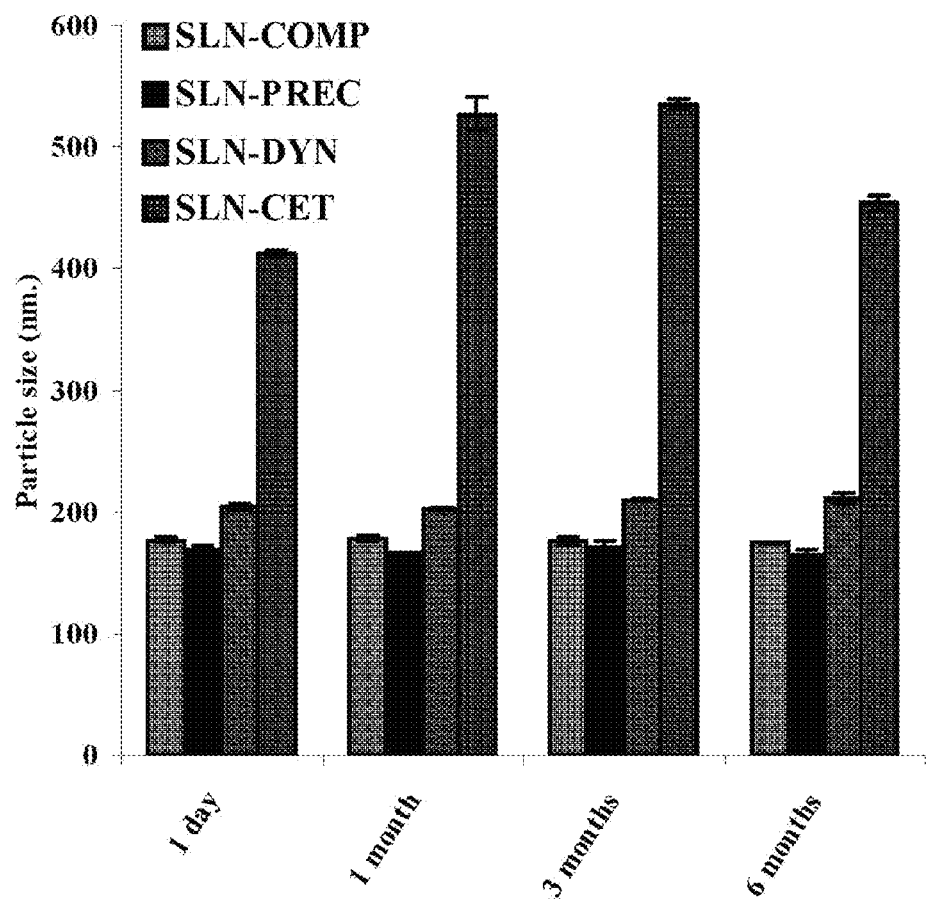
FIGS. 9A, 9B, 9C, and 9D show the long-term stability study results of unloaded solid lipid nanoparticles and nanostructured lipid carriers at different tocotrienol rich fraction loads by percent at 0% (FIG. 9A), 10% (FIG. 9B) 30% (FIG. 9C), and 50% (FIG. 9D).
Figure 9B:
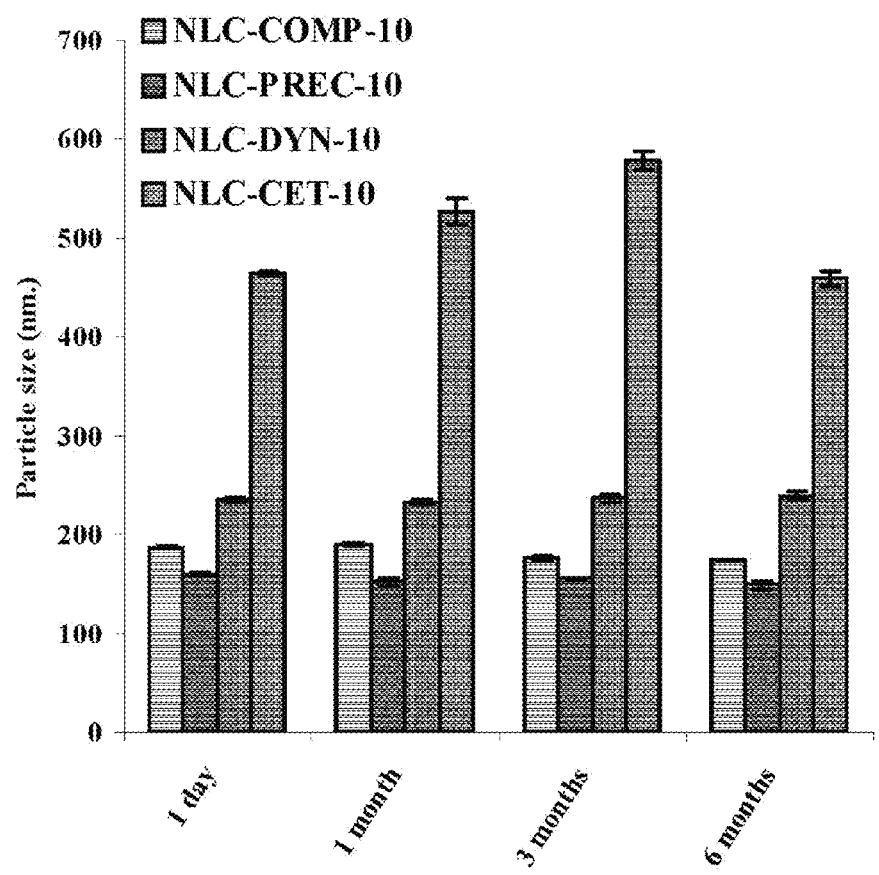
Figure 9C:
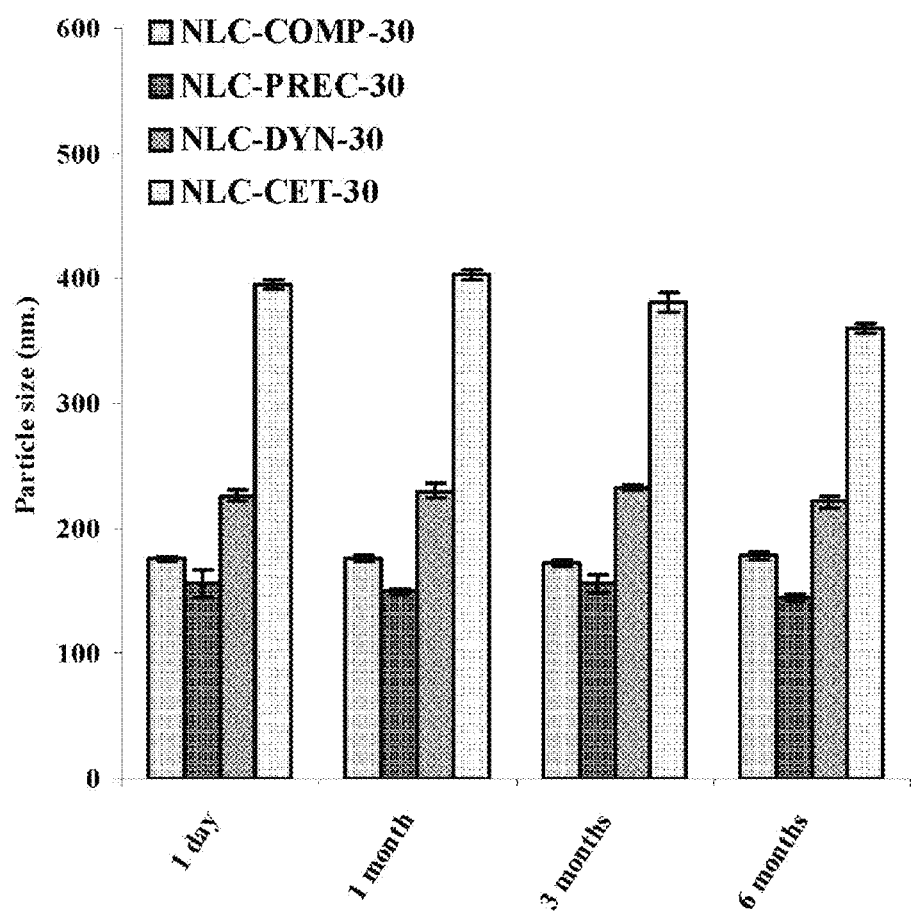
Figure 9D:
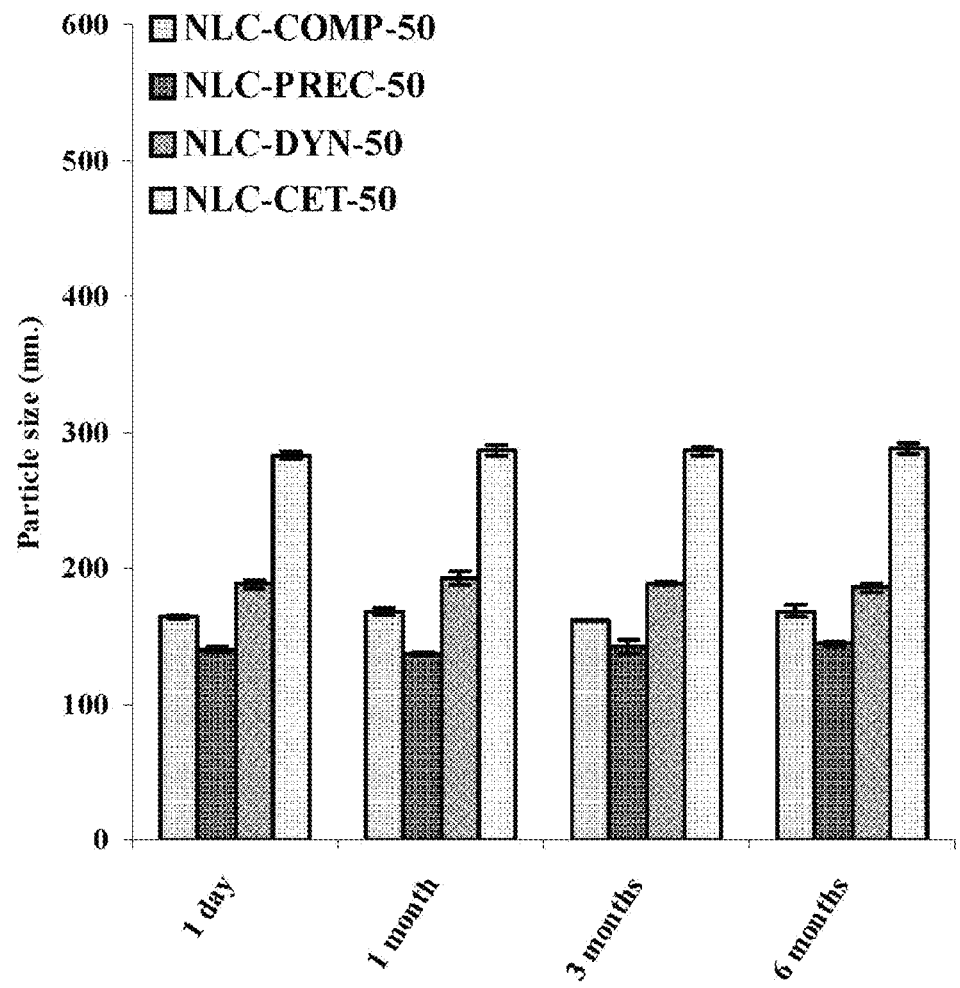
Figure 10:
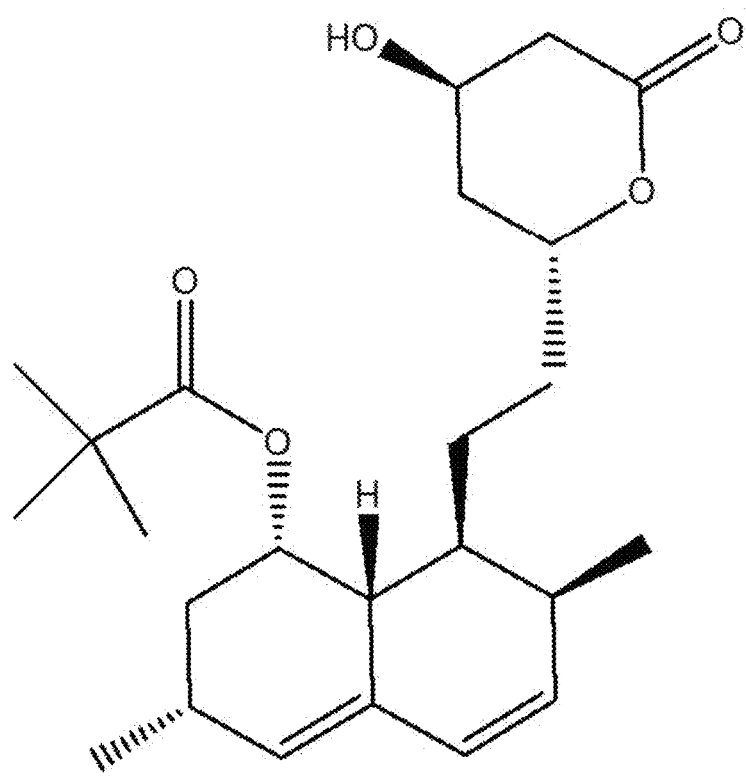
FIG. 10 shows the chemical structure of simvastatin.

To eliminate the possibility of tocotrienol-rich-fraction decomposition or loss during nanostructured lipid carriers preparation as a cause for tocotrienol-rich-fraction signal attenuation, the tocotrienol-rich-fraction was extracted from the nanostructured lipid carriers and analyzed by NMR. Briefly, nanostructured lipid carrier formulations were thoroughly mixed with deuterated chloroform. The blends were then allowed to separate into aqueous and organic layers. Both layers were analyzed independently by $^1$H-NMR and the data were compared to the spectral data of the stock solutions of tocotrienol-rich-fraction and solid lipid dissolved in chloroform-D. FIGS. 8A, 8B, 8C, and 8D shows the spectra for tocotrienol-rich-fraction in CD$_3$Cl (8A), glycerol tristearate (8B), chloroformic layer after extraction took place (8C), and the aqueous layer (8D). Signal matching based on literature reports of tocotrienol protons assignment indicated that tocotrienol-rich-fraction should not decompose or degrade by the preparation procedure. $^1$H-NMR analysis of the chloroform layer after extraction revealed the characteristic tocotrienol-rich-fraction signals (FIG. 8A), which were distinguishable from the signals of the solid lipids (FIG. 8B). The solid arrows in FIG. 8C indicate tocotrienol-rich-fraction protons, and the dashed arrows point towards both tocotrienol-rich-fraction and glycerol tristearate protons (FIGS. 8A and 8B). The signal at approximately 3.81 ppm may be attributed to poloxamer 188, which may have been partly extracted into the chloroform layer (FIG. 8C). In the aqueous layer, the distinct poloxamer 188 proton at 1.11 ppm clearly prevailed.

For further confirmation, tocotrienol-rich-fraction concentration in the nanostructured lipid carriers was quantified by HPLC. This HPLC analysis, revealed 90-110% tocotrienol-rich-fraction entrapment efficiency.

Solid lipid nanoparticle, nanostructured lipid carrier, and tocotrienol-rich-fraction-nanoemulsion samples were stored at 25° C. and subjected to a 6 months stability study. The average particle size of the dispersions was measured as described above after appropriate time intervals, which included one day following preparation and one, three, and six months after preparation. The average particle size of the samples is given in FIGS. 9A, 9B, 9C, and 9D. As shown, the particle size of the formulations did not significantly ($p > 0.05$) differ from those measured after one day of preparation. These results imply good long-term stability of the formulations, which was further confirmed by particle size homogeneity and the absence of visible phase separation.

Solid lipid nanoparticles could be readily prepared by a hot o/w microemulsion procedure. Furthermore, solid lipid nanoparticles and nanostructured lipid carriers were shown to be stable over an extended period of time at controlled room temperature with respect to particle size, phase homogeneity, and lipid content. The results indicate that tocotrienol-rich-fraction-nanostructured lipid carriers likely localize tocotrienol rich fraction in the core of nanostructured lipid carriers. Incorporating tocotrienol-rich-fraction into solid lipid nanoparticles created nanosystems that were not comparable to the physical mixtures of tocotrienol-rich-fraction-nanoemulsion and tocotrienol-rich-fraction-unloaded solid lipid nanoparticles. This was confirmed by $^1$H-NMR data and suggested strong interaction between the tocotrienol-rich-fraction molecules and the solid lipid nanoparticles. These results also inferred that tocotrienol-rich-fraction might be concentrated in the interior cores of nanostructured lipid carriers or uniformly distributed over the lipid phase. However, the ability of solid lipids to generate spatial vacancies for the accommodation of tocotrienol-rich-fraction drug molecules rendered the signals of aromatic protons of the chromane ring undetectable and strongly suggests the internalization of tocotrienol-rich-fraction within nanostructured lipid carriers. Differential scanning calorimetry measurements provided further confirmation on the retention of the tocotrienol-rich-fraction within the inner compartments of the solid matrix.

Differential scanning calorimetry and NMR data reflected the degree of mobility and/or fluidity of the nanostructured lipid carriers, which was strongly influenced by the ordered crystal lattice structure of the solid lipids. This was readily seen when nanostructured lipid carriers were analyzed by $^1$H-NMR at elevated temperature that exceeded the melting point of the solid lipids. Initially, the internalization of tocotrienol-rich-fraction into solid lipid nanoparticles (Crystal doping by tocotrienol-rich-fraction oil molecules) distorted the crystalline structure of the lipid core. By heating the nanostructured lipid carrier dispersions to 90° C., the tocotrienol-rich-fraction chromane ring diffuses to the external surfaces of the particles and becomes exposed to the poloxamer solution. Such an increase in tocotrienol-rich-fraction mobility and the exposure of the chromane ring to the aqueous medium improved peak shape and amplitude. The intensity of the peaks when the formulations were allowed to cool to room temperature, however, decreased significantly, implying the restriction in mobility of the chromane ring methylene group and the formation of strong tocotrienol-rich-fraction and solid lipid nanoparticles bonds. The results of this research support the idea of tocotrienol-rich-fraction internalization within nanostructured lipid carriers rather than surface adsorption. The mobility of the hydrophilic head moieties was maintained outside towards the aqueous surfactant solution. Whereas protons of the benzene ring were embedded inside solid lipid nanoparticles cores and were sterically obstructed by solid lipids.

Not wishing to be bound by theory, it is believed that tocotrienol-rich-fraction molecules are attracted to the solid lipids forming the cores of the nanoparticles. The imbibition of tocotrienol-rich-fraction within the nanostructured lipid carriers rather than a mere surface adsorption was confirmed by the gradient change in the melting endotherm as evident by differential scanning calorimetry data and the broad $^1$H-NMR signals. NMR studies were also capable of quantifying the extent of particle mobility within the aqueous dispersions, which provided further evidence on the internalization of tocotrienol-rich-fraction molecules within nanostructured lipid carriers. Of particular interest was the observation that the mobility of the molecules increased with an increase in tocotrienol-rich-fraction concentration, nonetheless, particles retained their physical form with tocotrienol-rich-fraction loading as high as 50% of the total lipid content. tocotrienol-rich-fraction, at high loading, was not ejected from the molten lipid phase during the lipid crystallization process at the cooling step and did not relocate into the more polar environment, which is the aqueous surfactant bulk. This data confirms the possibility of creating lipid nanoparticles with blends of high and low melting points lipids and indicates that inner oil domains exist in the solid lipid nanoparticles. This is essential to enable higher drug loading and suppression of premature drug release, which are frequently cited problems with solid lipid nanoparticles. The nanostructured lipid carriers did not contain free tocotrienol rich fraction and they did not demonstrate instability issues.

Examples 2(A)-2(K)

Tocotrienol rich fraction is an oily mixture of tocopherols and tocotrienols, in which tocotrienols constitute 70-90% of the blend. The Vitamin E general formula discussed above shows the generalized chemical structure of the vitamin E compounds including the variations between the different forms of vitamin E compounds. Both tocopherols and tocotrienols have similar chemical structure characterized by a phytyl side chain attached to a chromane ring. Lipid nanoparticles such as nanostructure lipid carriers (NLCs) and solid lipid nanoparticles (SLNs) are aqueous colloidal dispersions with a size in the range of 50-1000 nm. The matrix of solid lipid nanoparticles is composed of biodegradable and biocompatible solid lipids. Unlike solid lipid nanoparticles, however, the cores of the nanostructured lipid carriers are composed of blends of lipids in which liquid low melting-point lipids, such as tocotrienol rich fraction, are entrapped in the form of oily nanocompartments within a solid matrix. The physiochemical properties of the simvastatin-tocotrienol rich fraction nanoparticles, such as particle size, surface morphology, drug entrapment efficiency, in vitro drug release, and stability, were assessed and the cellular antiproliferative effect of the simvastatin-tocotrienol rich fraction nanoparticles against the highly malignant neoplastic +SA mammary epithelial cells was evaluated.

Multiple compounds were used in the development and evaluation of embodiments relating to examples 2(A)-2(K). Glyceryl behenate (COMP) sold as Compritol® 888 ATO has a melting point of 71-74°, which is a mixture of ~15% mono-, 50% di- and 35% triglycerides of behenic acid, was provided by Gattefossé (Saint-Priest, Cedex, France); methanol HPLC grade, (±)-α-tocopherol (α-T); methylthiazolyldiphenyl tetrazolium bromide (MTT), bovine serum albumin (BSA), and other chemicals for cell culture experiments were purchased from Sigma Chemical Company (St. Louis, Mo., USA); Poloxamer 188 is a compound having a general formula described above and is sold under the trade name Lutrol® F 68 NF, and obtained from BASF (Florham Park, N.J.); simvastatin (SIM) was purchased from Haorui Pharma-Chem. Inc. (Edison, N.J.); tocotrienol-rich-fraction of palm oil (TRF), which contains 9.8% α-tocopherol, 27.9% α-tocotrienol, 41.4% γ-tocotrienol, 19.2% δ-tocotrienol was a gift from Davos Life Science PTE LTD (Singapore); deionized water was obtained from NanoPure purification system. All chemicals were used as supplied without further modification.

Example 2(A)

Dissolution Study

In order to incorporate a drug into solid lipid nanoparticles, it should possess a sufficiently high solubility in the solid lipid. Therefore, prior to solid lipid nanoparticle preparation, a preliminary study was performed to determine if simvastatin could be dissolved in glyceryl behenate. This was done by dissolving various amounts of simvastatin in molten glyceryl behenate. After cooling and re-solidification, however, simvastatin crystals were readily seen when the glyceryl behenate/simvastatin blends were inspected by polarized light microscopy. Nanostructured lipid carriers in which a liquid oil is added to the solid lipid in order to enhance simvastatin payload in the nanoparticles were developed. This was achieved by substituting a portion of the lipid phase (i.e., glyceryl behenate) with either tocotrienol rich fraction (or α-tocopherol). Evidence indicated that the presence of tocotrienol rich fraction and α-tocopherol were correlated with disorder in the crystalline structure of glyceryl behenate.

Example 2(B)

Nanoparticle Preparation

Nanoparticles were prepared by an oil in water (o/w) microemulsion technique using a variation of the high-shear homogenization described in "Optimization of Procedure Parameters and Physical Stability of Solid Lipid Nanoparticles in Dispersions" by Ahlin P, Kristl J, Šmid-Kober J. Acta Pharm 1998; 48: 257-67. Briefly, glyceryl behenate alone or in combination with simvastatin, tocotrienol rich fraction (or α-tocopherol), were allowed to melt at 80° C. Meanwhile in a separate vial, Poloxamer 188 was dissolved in purified water and heated to 80° C. The hot surfactant solution was then added to the molten lipid under high-shear homogenization at 20,000 rpm using a homogenizer sold as the IKA® Ultra-Turrax T8 mixer (IKA® Works Inc., NC, USA). After 5 minutes, the o/w microemulsion was sonicated for 10 minutes using an ultrasonic homogenizer at 60% pulsar rate (Model 150VT, Biologics, Inc., Manassas, Va.). Pulsar rate represents the percentage of the time that the ultrasonic homogenizer is running during a given homogenization time. After homogenization, nanoparticles were formed by annealing the sonicated dispersions overnight at 4° C. The concentrations of the lipid phase, including the drug(s) and the emulsifier in the dispersions, were 0.25% and 0.125% w/v, respectively. The amount of simvastatin and tocotrienol rich fraction (or α-tocopherol) added to the lipid phase was adjusted so as to obtain dispersions that contain 1 mM of simvastatin and 5 mM of either tocotrienol rich fraction or α-tocopherol. The compositions of the nanoparticles that were evaluated in this study are listed in the table of FIG. 11. FIG. 11 also contains the composition, intensity weighed Z-average particle diameter (Z-ave), and zeta potential (zeta potential) of unloaded solid lipid nanoparticles and tocotrienol rich fraction for α-tocopherol nanostructured lipid carriers with or without simvastatin. Each data point in FIG. 11 represents mean±SD.

Example 2(C)

Differential Scanning Calorimetry

For the differential scanning calorimetry and powder X-ray diffraction studies, either binary blends of tocotrienol rich fraction (or α-tocopherol) with glyceryl behenate or ternary blends of simvastatin, tocotrienol rich fraction (or α-tocopherol), and glyceryl behenate were evaluated. The binary blends were prepared by mixing the tocotrienol rich fraction (or α-tocopherol) with molten glyceryl behenate at 85° C. Ternary blends were prepared by dissolving simvastatin in the molten glyceryl behenate/tocotrienol rich fraction (or α-tocopherol) blends. Molten blends were allowed to re-congeal at room temperature overnight prior to their analysis.

Thermal analysis was performed to examine the physical state of simvastatin in the nanoparticles. Differential scanning calorimetry analyses were performed using modulated differential scanning calorimetry (2920 Modulated differential scanning calorimetry machine from TA Instruments-Waters LLC, New Castle, Del.). Samples (2-10 mg) hermetically sealed in aluminum pans were heated from 20° C. to 170° C. at a rate of 10° C./min. Melting endotherms were estimated from the generated data by computer. The software used was sold under the name Universal Analysis 2000 version 4.2E available from TA Instruments-Waters LLC, New Castle, Del.

Tocotrienol rich fraction-glyceryl behenate and α-tocopherol-glyceryl behenate binary blends were characterized by differential scanning calorimetry. Binary blends were prepared by mixing either tocotrienol rich fraction or α-tocopherol with the molten lipid (glyceryl behenate) at 85° C. Once cooled, the melting point of the solid mixtures was measured by differential scanning calorimetry. The thermograms of tocotrienol rich fraction-glyceryl behenate and α-tocopherol-glyceryl behenate binary blends revealed endothermic peaks at approximately 63° C. and 65° C., respectively (see FIGS. 12A and 12B, respectively), which were lower than the melting point of the bulk glyceryl behenate (~73° C.). Lower melting points implied that an interaction between glyceryl behenate and either tocotrienol rich fraction (or α-tocopherol) resulted in a decrease in the crystallinity of the glyceryl behenate-tocotrienol rich fraction (or α-tocopherol) lipid matrix.

Figure 12A:
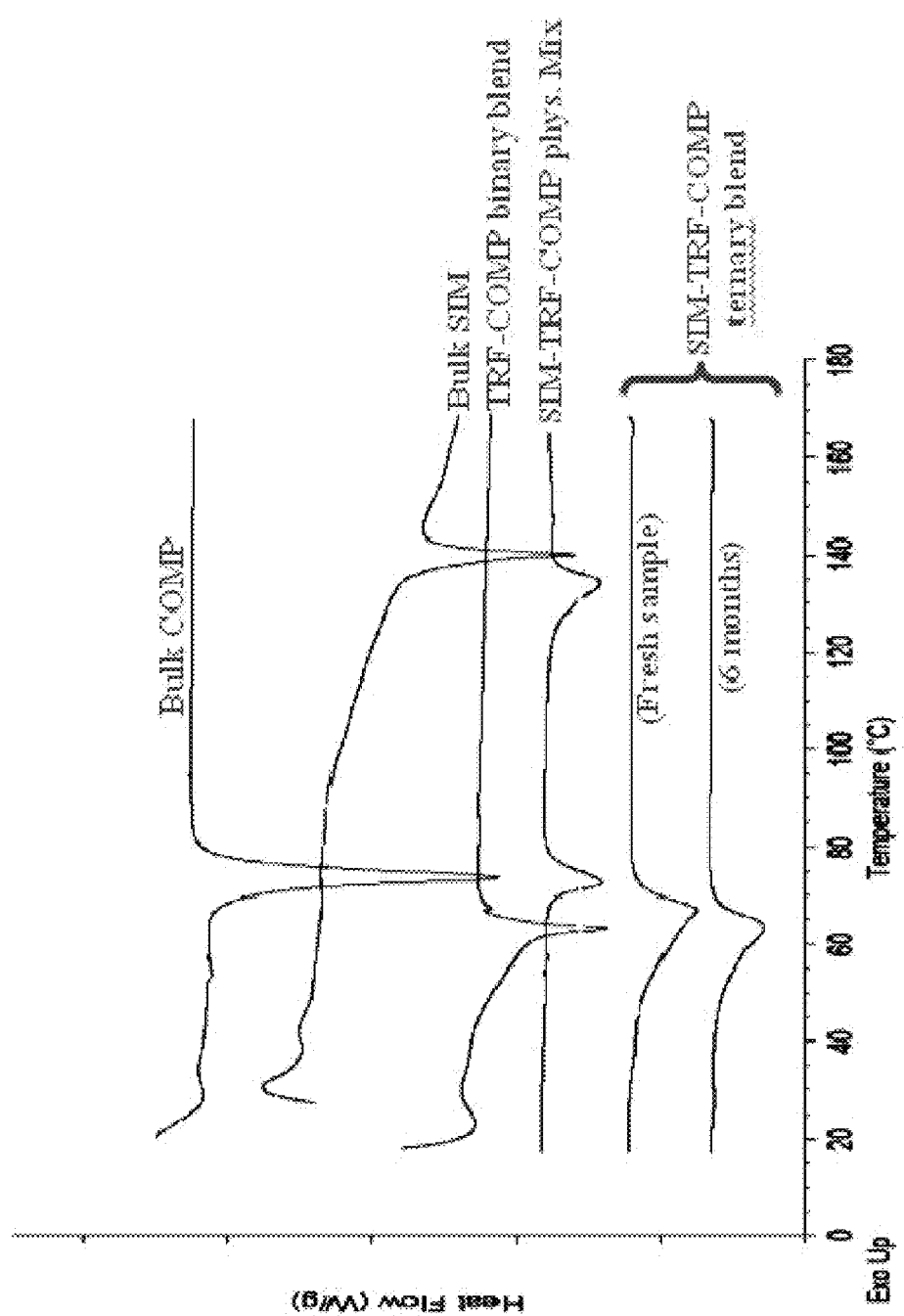
FIG. 12A shows differential scanning calorimetry profiles for various tocotrienol rich fraction based blends.
Figure 12B:
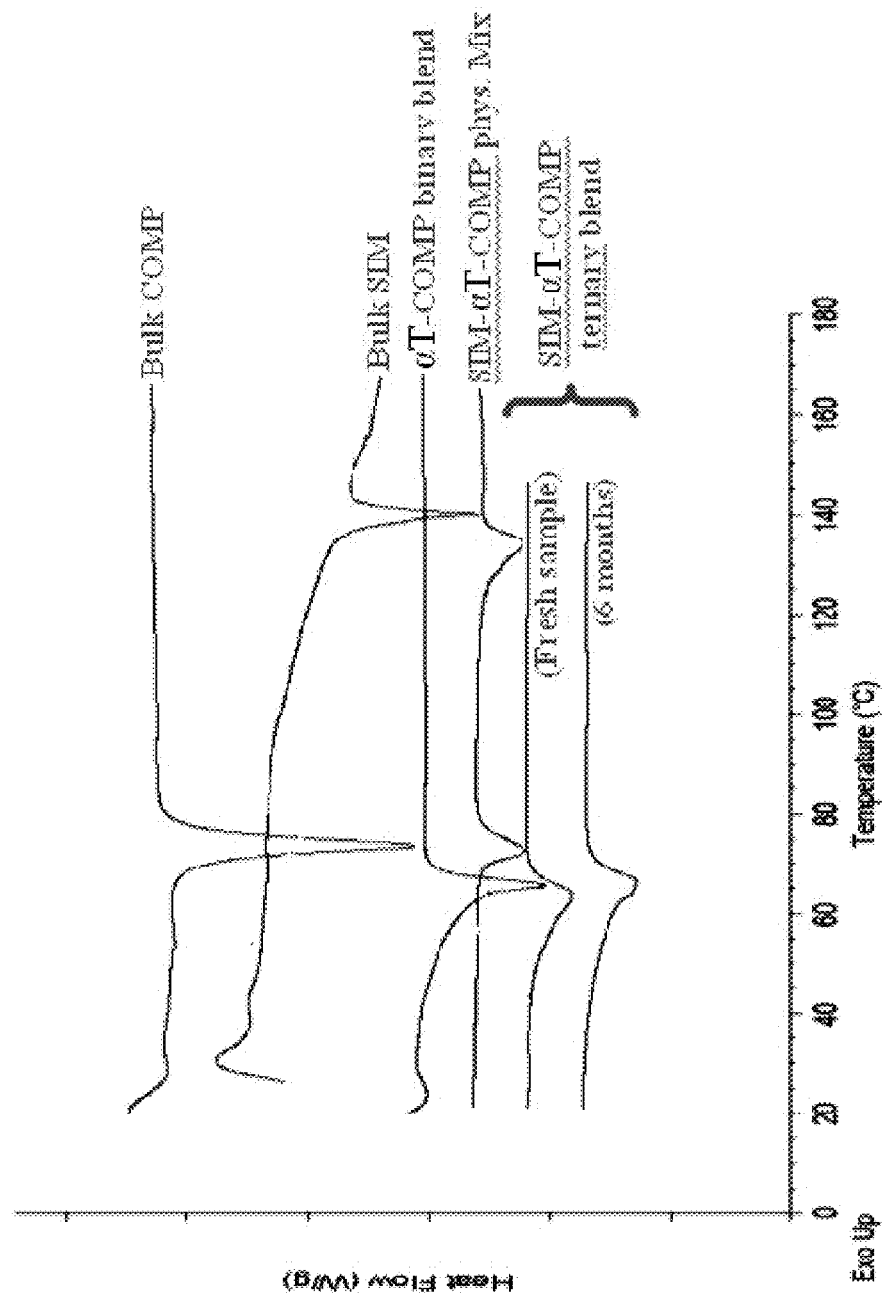
FIG. 12B shows differential scanning calorimetry profiles for various α-tocopherol based blends.

Differential scanning calorimetry complemented with powder X-ray diffraction measurements were used to investigate the physical state of simvastatin in either tocotrienol rich fraction-glyceryl behenate or α-tocopherol-glyceryl behenate blends. The differential scanning calorimetry thermograms corresponding to the physical mixtures of simvastatin, glyceryl behenate, and either tocotrienol rich fraction or α-tocopherol were compared to those of simvastatin-tocotrienol rich fraction-glyceryl behenate or simvastatin-α-tocopherol-glyceryl behenate ternary blends. The ternary blends were prepared by solubilizing simvastatin in the molten tocotrienol rich fraction-glyceryl behenate or α-tocopherol-glyceryl behenate blends. As shown in the differential scanning calorimetry thermograms (FIGS. 12A and 12B), the physical mixture of either simvastatin-tocotrienol rich fraction-glyceryl behenate or simvastatin-α-tocopherol-glyceryl behenate showed two distinct endothermic peaks at approximately 73° C., which corresponded to the melting point of glyceryl behenate, and 133° C. (or 140° C. in the case of α-tocopherol), which corresponded to the melting point of simvastatin. The presence of two distinctive endotherms indicated that both simvastatin and glyceryl behenate were in crystalline state and that an interaction did not exist between glyceryl behenate and either tocotrienol rich fraction or α-tocopherol. In contrast, differential scanning calorimetry profiles of the ternary blends revealed a single broad endotherm at 60° C. and 71° C., for simvastatin-tocotrienol rich fraction-glyceryl behenate and simvastatin-α-tocopherol-glyceryl behenate, respectively, which suggested the presence of simvastatin as a molecular dispersion in the partially crystalline glyceryl behenate. No change was observed in the thermal plots of the ternary blends after 6 month of storage. FIGS. 12A and 12B show differential scanning calorimetry profiles of tocotrienol rich fraction based (see FIG. 12A) and α-tocopherol based (see FIG. 12B) blends showing the endotherms of glyceryl behenate (Comp), bulk simvastatin (SIM), glyceryl behenate-tocotrienol rich fraction (or α-tocopherol) binary blend, physical mixture of simvastatin-tocotrienol rich fraction (or α-tocopherol)-glyceryl behenate (at ratio 0.2:1:1), and simvastatin-tocotrienol rich fraction (or α-tocopherol)-glyceryl behenate ternary blend (at ratio 0.2:1:1), when freshly prepared and after 6 months of storage. The curves of FIGS. 12A and 12B were displaced along the ordinate for better visualization.

Example 2(D)

X-Ray Diffraction

The crystallinity of the simvastatin-tocotrienol rich fraction-glyceryl behenate or simvastatin-α-tocopherol-glyceryl behenate ternary blends was evaluated by powder X-ray diffraction. X-ray diffraction patterns were obtained by wide-angle X-ray scattering (WARS, 2τ=5–50°, step size=0.5) using an X-ray generator available under the name Philips PW 1830 X-ray generator from Philips, Amedo, Netherlands, fitted with a copper anode tube (Cu—Kα radiation, λ=1.5418 nm) and a Goniometer detector sold as the Goniometer PW 18120 detector. Data of the scattered radiation were recorded at an anode voltage of 40 kV and a current of 35 mA.

Figure 13:
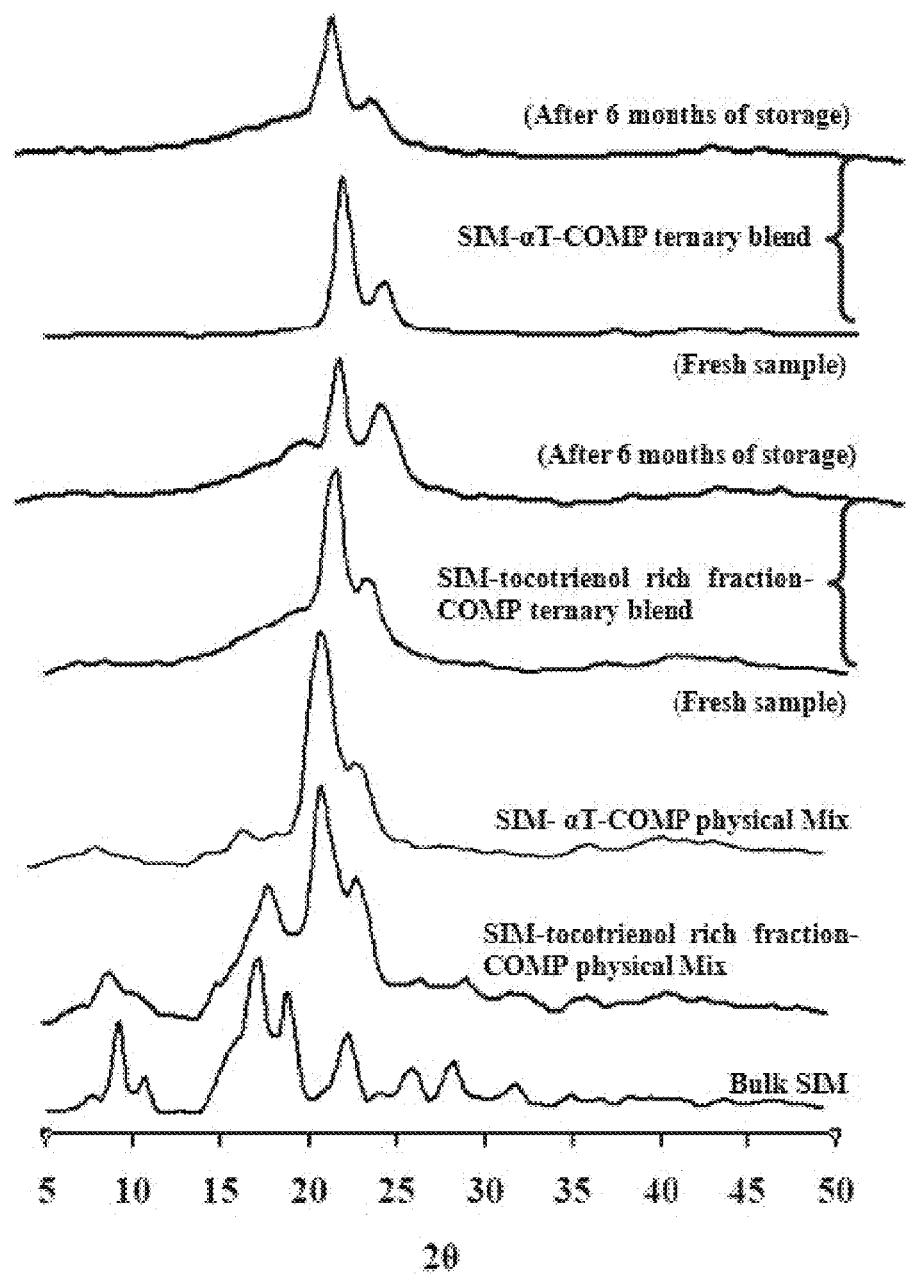
FIG. 13 shows powdered X-ray diffraction patterns for various compositions tested.

The wide-angle powder X-ray diffraction pattern for bulk simvastatin (see FIG. 13) revealed major peaks at 2θ=9.25, 16.75, 17.25, 18.75, 22.75, 25.25, 28.25, and 31.75. The intensity of the peaks decreased when simvastatin was physically mixed with either tocotrienol rich fraction (or α-tocopherol), and glyceryl behenate, which could be attributed to lower simvastatin loading. Nonetheless, the apparent peaks at 2θ=16.75, 17.25, and 18.75 in the physical mixture indicate the presence of simvastatin in crystalline form. These peaks disappeared from the diffraction pattern of the solidified ternary blends. These blends were prepared by solubilizing simvastatin in the molten tocotrienol rich fraction (or α-tocopherol) glyceryl behenate blends in a process that simulated nanostructured lipid carrier production. The peak at 2θ=20.75, accompanied with a small shoulder of low intensity at 2θ=21.25, corresponds to glyceryl behenate β'-modification. These results confirmed the existence of simvastatin as a molecular dispersion in the tocotrienol rich fraction-glyceryl behenate or α-tocopherol-glyceryl behenate blends. As with differential scanning calorimetry, no changes in the crystallinity of the ternary blends were seen after six months of storage (see FIG. 13), which validated the observed long term stability and high entrapment efficiency of simvastatin in the nanoparticles as discussed below. FIG. 13 shows powder X-ray diffraction patterns. From bottom to top in FIG. 13 are bulk simvastatin, simvastatin in physical mixture with tocotrienol rich fraction and glyceryl behenate (0.2:1:1), simvastatin in physical mixture with α-tocopherol and glyceryl behenate (0.2:1:1), simvastatin blend with tocotrienol rich fraction and glyceryl behenate (0.2:1:1) freshly prepared and after six months of storage at controlled room temperature, simvastatin blend with α-tocopherol and glyceryl behenate (0.2:1:1) freshly prepared and after six months of storage. The curves of FIG. 13 were displaced along the ordinate for better visualization.

Example 2(E)

Entrapment Efficiency Study

After the preparation of the nanoparticles, there was no evidence of separation of either liquid oils or simvastatin. To confirm simvastatin retention within the nanostructured lipid carriers, an entrapment efficiency study was performed. The EE % of simvastatin in simvastatin-tocotrienol rich fraction nanostructured lipid carriers and simvastatin-α-tocopherol nanostructured lipid carriers was 99.9±1.3 and 99.9±0.8, respectively. High entrapment efficiency of simvastatin in the nanostructured lipid carriers could be attributed to the presence of the liquid nanocompartments formed by tocotrienol rich fraction (or α-tocopherol), which were entrapped within the solid matrix of the nanostructured lipid carriers. Not wishing to be bound by theory, the nanostructured lipid carriers may serve as nano-reservoir drug delivery systems for simvastatin. These results confirm earlier differential scanning calorimetry and powder X-ray diffraction data with regard to simvastatin dissolution in the glyceryl behenate/tocotrienol rich fraction (or α-tocopherol) blends.

The entrapment efficiency (EE) of the simvastatin nanostructured lipid carriers was determined by measuring the concentration of the free unloaded simvastatin in the aqueous phase of the nanostructured lipid carrier dispersions. Approximately 1.0 mL of the dispersion was placed in the inner chamber of a 30K Millipore filters assembly (Ultracel-30K Millipore filter) having a molecular weight cutoff (MWCO) of 30,000 Da (Millipore Corporation, Billerica, Mass.). The assembly was then centrifuged at 5000 rpm (approximately 3000×g) for 15 minutes at 5° C. using an Eppendorf® 580R centrifuge (Hamburg, Germany). The nanostructured lipid carriers, along with the encapsulated simvastatin, remained in the inner chamber, whereas the aqueous dispersion medium containing the free simvastatin moved to the sample recovery chamber through the filter membrane. After separation, the amount of the free simvastatin in the dispersion medium was estimated by HPLC. Simvastatin entrapment efficiency and simvastatin loading were subsequently calculated from the following equation:

$$\text{Entrapment efficiency}(\%) = \frac{\text{Amount of } SIM \text{ entrapped in } NLCs}{\text{Theoretical total amount of } SIM \text{ added to } NLCs} \times 100$$

$$SIM \text{ loading}(\%) = \frac{\text{Amount of } SIM \text{ entrapped in } NLCs}{\text{Amount of solid lipid} + \text{amount of } SIM} \times 100$$

The amount of simvastatin entrapped in nanostructured lipid carriers was calculated by subtracting the amount of free simvastatin from the theoretical amount of simvastatin added to the nanostructured lipid carriers.

Example 2(F)

Particle Characterization

The intensity-weighed mean particle size, population distribution (polydispersity index), and zeta potential of the nanoparticles were measured by photon correlation spectroscopy (PCS) at 25° C. and 90° fixed angle using a zeta potential and submicron particle size analyzer sold as the Nicomp™ 380 ZLS from PSS Inc., Santa Barbara, Calif. When needed, samples were diluted with 0.2 µM filtered and deionized water. Analyses were performed in triplicate unless otherwise specified.

Various formulations were screened by substituting 10% to 50% of glyceryl behenate with either tocotrienol rich fraction or α-tocopherol. Complete dissolution was observed when blends with 50% tocotrienol rich fraction (or α-tocopherol) were used. This was confirmed when the blends were inspected by polarized light microscopy. Absence of visible crystals indicated that simvastatin was present as a solid solution and was molecularly dispersed in the lipid matrix. This information coupled with the results from the differential scanning calorimetry and powder X-ray diffraction studies further confirmed the dissolution of simvastatin in the glyceryl behenate-tocotrienol rich fraction (or α-tocopherol) blends.

Nanoparticles were prepared from their microemulsion precursors by high-shear homogenization followed by ultra-sonication. The compositions of the nanoparticles, their Z-ave diameters, and polydispersity indexes (PI) are listed in the data table presented in FIG. 11. The Z-ave of the solid lipid nanoparticles was 152 nm. The size of the nanoparticles, however, decreased significantly when 50% of glyceryl behenate was substituted with tocotrienol rich fraction (or α-tocopherol). For instance, the Z-ave for tocotrienol rich fraction based nanostructured lipid carriers was ~100 nm, whereas the Z-ave of unloaded solid lipid nanoparticles was ~152 nm. Lower particle size could be attributed to the efficient packing of the disrupted crystalline structure of glyceryl behenate when blended with tocotrienol rich fraction (or α-tocopherol). These data also suggested that solid lipid nanoparticles can encapsulate liquid oils up to 50% by weight without compromising the size of the nanoparticles. The entrapment of simvastatin into nanostructured lipid carriers did not change the size of the nanoparticles. Simvastatin nanoparticles had particle sizes of about 100 nm, which should be ideal for future in vivo administration. Nonetheless, the size of the nanoparticles may vary with factors such as the difference in temperature between the warm microemulsion and the refrigerator during the cooling process and the composition of each formulation. These factors were maintained constant in this study.

Polydispersity Index (PI) is considered an indicator of particle distribution. The nanoparticle dispersions tested had PI values in the range from 0.20 to 0.29 (Table VII), which indicated that the nanoparticles prepared in this study were mono-disperse. Tocotrienol rich fraction or α-tocopherol incorporation into solid lipid nanoparticles, however, significantly decreased PI, which reflected their positive impact on dispersion uniformity.

With regard to the stability of solid lipid nanoparticles and nanostructured lipid carriers, it has been reported that zeta potential values below −30 mV impart sufficient electrostatic repulsion between the nanoparticles, which favor improved physical stability. The use of steric stabilizers was also shown to produce stable formulations. The nanoparticles studied had zeta potential values in the range from −9.0 to −21.0 mV. While the zeta potential values were in a range not indicated by previous reports to have a desired level of electrostatic repulsion, the Z-ave did not significantly change over six months of storage at room temperature (data shown in stability section below). The long-term stability of the nanoparticles could be attributed to poloxamer 188. Furthermore, glyceryl behenate may contribute to the stability of the nanoparticles.

Example 2(G)

SEM Analysis

The size and morphology of the nanoparticles were observed using a scanning electron microscope (Type FP 2012/13 Quanta 200 from FEI, Netherlands) fitted with a cryotransfer system (Gatan/Alto 2100 Cryotrans System from Gatan Instruments, Oxon, UK). To minimize potential morphological changes during the SEM drying process, nanostructured lipid carriers were cryotransferred with liquid nitrogen prior to analysis. This was achieved by first cooling and maintaining the nanostructured lipid carrier samples for at least 1 min at −170° C. by liquid nitrogen in the cryotransfer system. Then the samples were freeze-fractured with a cryohoning device. The temperature of the freeze-fractured specimen was then raised to −80° C. to allow controlled sublimation of the water. This etching process was arrested by rapidly lowering the temperature to −170° C. Finally, the specimens were coated with gold and examined by a scanning electron microscope.

Figure 17:
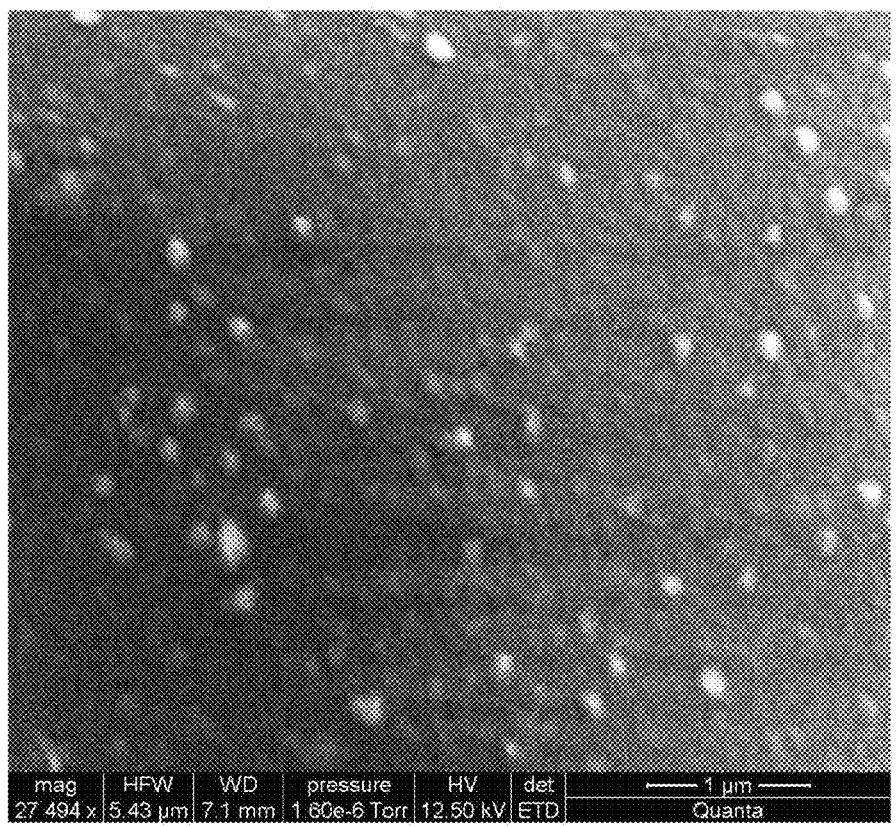
FIG. 17 shows a cryo-scanning electron microscope image of simvastatin-tocotrienol rich fraction nanostructured lipid carriers.

FIG. 17 shows a representative image of simvastatin-tocotrienol rich fraction nanostructured lipid carriers. The nanoparticles have spherical or ellipsoidal shapes. No simvastatin nanocrystals were visible. The size of the nanoparticles as determined from the Cryo-SEM images correlated well with the particle size data that were reported in the table of FIG. 11.

Example 2(G)

Drug Release Studies

The release of simvastatin from either simvastatin-tocotrienol rich fraction nanostructured lipid carriers or simvastatin-α-tocopherol nanostructured lipid carriers was measured at 37° C. under sink conditions. One milliliter of either nanostructured lipid carrier dispersion (equivalent to 0.4 mg simvastatin) was suspended in 9.0 mL phosphate buffer saline (PBS, pH 7.4 and 6.5) containing 30% ethanol. Aliquots of the dissolution medium were withdrawn at different time intervals and replaced with fresh dissolution medium to maintain a constant volume. Collected samples were centrifuged using 30K millipore filters (Ultracel) at 5000 rpm (approximately 3000×g) for 15 minutes at 5° C. using a centrifuge (Eppendorf® 580R from Hamburg, Germany) to separate the nanoparticles from the free simvastatin. The nanostructured lipid carriers along with the encapsulated simvastatin remained in the inner chamber whereas simvastatin released into the dissolution medium was recovered in the outer chamber. The concentration of the released simvastatin was determined by HPLC. All experiments were carried out in triplicate. Results were expressed as mean±standard deviation.

Figure 14:
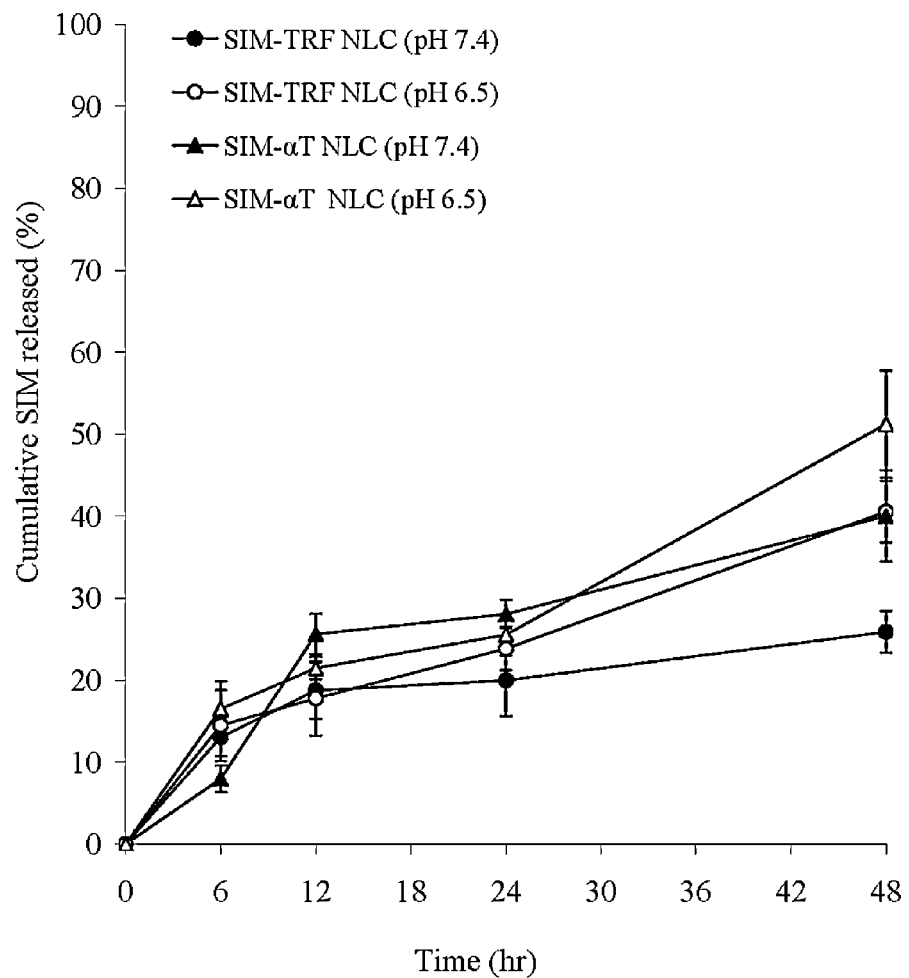
FIG. 14 shows in vitro release profiles for Simvastatin-tocotrienol rich fraction nanostructured lipid carriers and for Simvastatin-α-tocopherol nanostructured lipid carriers at a pH of 7.4 and 6.5.

The release of simvastatin from the nanostructured lipid carrier formulations was measured in vitro over a 48 hour period. Due to the low water solubility of simvastatin, 30% of ethanol in PBS buffer (pH 7.4 and 6.5) was used as the dissolution medium. The release profiles of simvastatin from the nanostructured lipid carriers at pH 7.4 and 6.5 are shown in FIG. 14. As shown, a biphasic simvastatin release pattern was observed. A burst period characterized by a fast drug release was evident in the first 10 hours, followed by a slower and controlled release until the end of the experiments. Simvastatin release from the nanoparticles at pH 7.4 was slower than its release at pH 6.5. The mechanism by which pH impacts the release of simvastatin from the nanoparticles is not clear. Nonetheless, the cumulative percentage of simvastatin released in either media ranged from 25% to 51% over the 48 hour test period. The cumulative amount of simvastatin released from α-tocopherol based nanostructured lipid carriers was higher than the corresponding cumulative amount released from the tocotrienol rich fraction based nanostructured lipid carriers. A significantly lower amount of simvastatin was released from the simvastatin-tocotrienol rich fraction-glyceryl behenate nanostructured lipid carriers, with only 25% released after 48 hours at pH 7.4. These results indicated that simvastatin, which was incorporated into tocotrienol rich fraction based nanostructured lipid carriers, was likely to remain associated with the nanoparticles. Not wishing to be bound by theory, the difference in release between the tocotrienol rich fraction and α-tocopherol based nanostructured lipid carriers could be attributed to the higher viscosity of tocotrienol rich fraction, which may retard the diffusion of simvastatin from the nanoparticles as predicted by the Stokes-Einstein's law. Furthermore, the slow and sustained release of simvastatin after the initial burst period indicated that simvastatin was likely not present at or near the surface of the nanoparticles but instead within the cores of the nanostructured lipid carriers as ideally predicted by the enhanced solvation ability of the nanocompartmental domains formed by either tocotrienol rich fraction or α-tocopherol. FIG. 14 shows the in vitro release profiles of simvastatin-nanostructured lipid carrier formulations at 37° C. in phosphate buffer saline containing 30% ethanol at pH 7.4 and 6.5. Data are represented as the mean±SD (n=3).

The concentration of simvastatin in the nanoparticle dispersions was determined by the following validated reversed-phase HPLC method. Briefly, the solution collected from the recovery chamber as discussed above was injected into a $C_{18}$ (4.6×100 mm) monolithic analytical column sold under the trademark Onyx® from Phenomenex®, Inc., Torrance, Calif., supported by a HPLC sold under the SpectraSystem brand by Thermo Electron Corporation, San Jose, Calif., equipped with a UV3000 UV/Visible variable wavelength detector. The detection of simvastatin was carried out at $\lambda_{max}$=238 using a 15% v/v water in methanol solution as the mobile phase, which was allowed to run at a flow rate of 1 mL/min. Data acquisition was performed using a chromatography software sold as ChromQuest™ version 4.2 by Thermo Electron Corporation, San Jose, Calif.

Example 2(H)

Stability Studies

Figure 15:
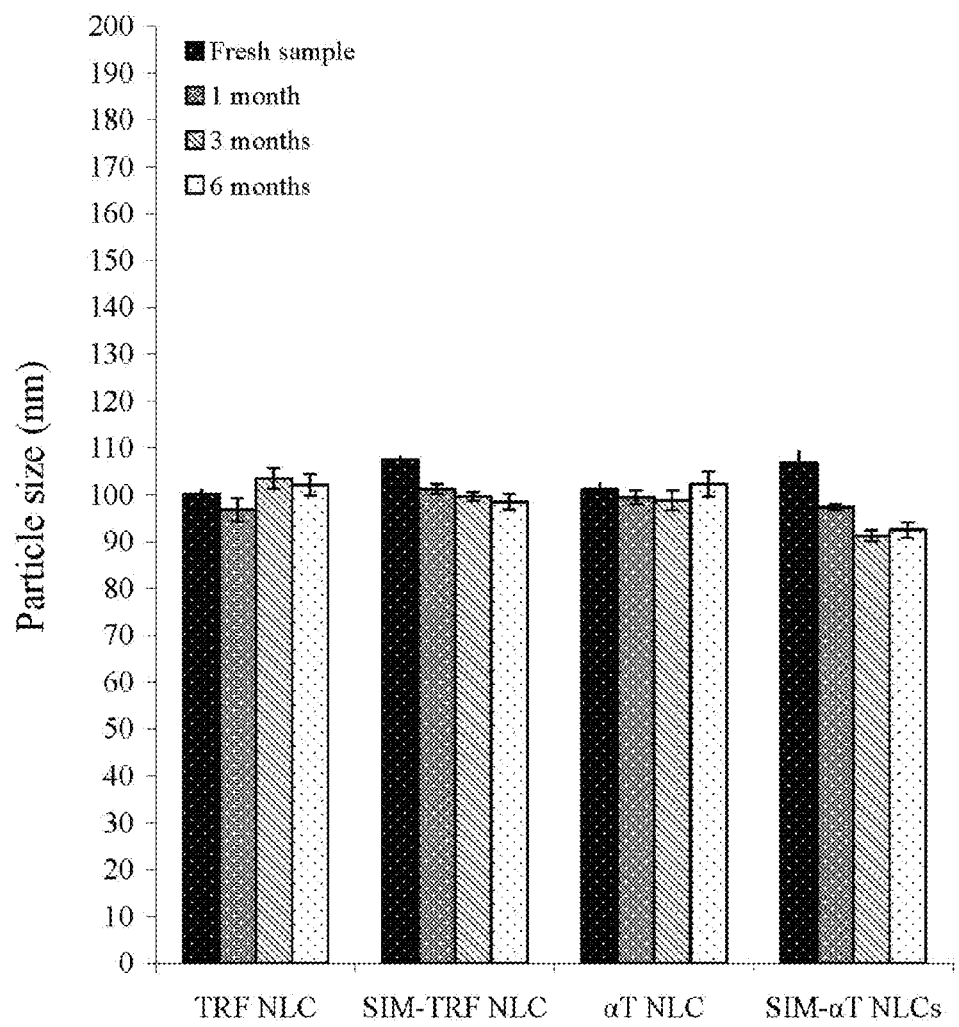
FIG. 15 shows long term particle size stability data for various nanostructured lipid carriers' formulations.

Nanoparticle dispersions were stored protected from light at controlled room temperature for 6 months. At different time intervals the particle size (Z-ave), population distribution measured by polydispersity index (PI), entrapment efficiency (EE), and zeta potential (ZP) of the dispersions were measured after 1, 3, and 6 months. After 6 months of storage, the Z-ave and zeta potential of the nanostructured lipid carriers did not significantly differ from the freshly prepared samples. FIG. 15 shows the Z-ave of nanostructured lipid carriers over 6 months of storage. As shown in the figure, the Z-ave changed from 100 to 102 nm, from 107 to 99 nm, from 101 to 103 nm, and from 106 to 92 nm for tocotrienol rich fraction-nanostructured lipid carriers, simvastatin-tocotrienol rich fraction nanostructured lipid carriers, α-tocopherol-nanostructured lipid carriers, and simvastatin-α-tocopherol nanostructured lipid carriers, respectively. PI for all samples was <0.35, indicating narrow distribution and monodispersity. All data are represented as the mean±SD (n=3). These results reflected good long-term stability of the nanostructured lipid carrier formulations, which was further confirmed by the absence of a distinctive simvastatin endothermic peak or crystalline pattern when analyzed after 6 months by differential scanning calorimetry and powder X-ray diffraction, respectively. To eliminate the possibility of drug expulsion from the nanoparticles during storage, nanostructured lipid carrier dispersions were visually inspected for signs of phase separation and were analyzed for simvastatin entrapment efficiency. The percentage of simvastatin that remained entrapped in the nanoparticles after 6 months of storage only marginally decreased from 99.9±1.3 to 99.2±0.43 and from 99.9±0.8 to 98.9±0.45 for the tocotrienol rich fraction and α-tocopherol based nanostructured lipid carriers, respectively.

Example 2(I)

Cell Culture Studies

Experiments conducted in this study utilized the highly malignant +SA mammary epithelial cell line. This cell line was derived from an adenocarcinoma that developed spontaneously in a BALB/c female mouse. The +SA cell line is characterized as being highly malignant, estrogen-independent, and displays anchorage-independent growth when cultured in soft agarose gels. When +SA cells are injected back into the mammary gland fat pad of syngeneic female mice, they form rapidly growing anaplastic adenocarcinomas that are highly invasive and metastasize to the lung. Cell cultures and the experimental procedures used in this present study have been previously described in detail in "Antiproliferative and Apoptotic Effects of Tocopherols and Tocotrienols on Preneoplastic and Neoplastic Mouse Mammary Epithelial Cells" McIntyre BS, Briski K P, Gapor A, Sylvester P W. Proc Soc Exp Biol Med 2000; 224: 292-301. Briefly, cells were grown and maintained in serum-free Dulbecco's modified Eagle's medium (DMEM)/F12 control media containing 5 mg/mL bovine serum albumin (BSA), 10 μg/mL transferrin, 100 μg/mL soybean trypsin inhibitor, 100 U/mL penicillin 100 μg/mL streptomycin, 10 μg/mL insulin, and 10 ng/mL EGF as a mitogen. Cells were maintained at 37° C. in a humidified atmosphere of 95% air and 5% $CO_2$.

Viable cell number was determined using the 3-(4,5-dimethylthiazol-2yl)-2,5-diphenyl tetrazolium bromide (MTT) colorimetric assay. Briefly, at the end of the treatment period, media in all treatment groups was removed and replaced with fresh control media containing 0.42 mg/mL MTT, and the cells were returned to the incubator for a period of 4 hours. At the end of the incubation period, media were removed, the MTT crystals were dissolved in 1 mL of isopropanol, and the optical density of each sample was read at 570 nm on a microplate reader (SpectraCount, Packard BioScience Company, Meriden, Conn.). Cell number was calculated against a standard curve prepared by plating known concentrations of cells, as determined by the hemocytometer, at the start of each experiment.

For all experiments, freshly prepared nanoparticle dispersions were filtered through either 0.22 or 0.45 μM sterile syringe filters. These dispersions were then added to the culture media at various concentrations to prepare treatment media supplemented with tocotrienol rich fraction or α-tocopherol nanostructured lipid carriers with or without simvastatin. Each time, the treatment media was prepared freshly just before the treatment. The sterile stock formulations were stored at 4° C. throughout the duration of the experiment.

+SA cells were initially plated at a density of $5\times10^4$ cells/well (6 wells/group) in serum-free defined control media in 24-well culture plates and allowed to adhere overnight. The following day, cells were divided into different treatment groups and media was removed and replaced with fresh control or treatment media, and then returned to the incubator. Cells in their respective treatment groups were fed fresh media every other day throughout experimentation. $IC_{50}$ values (dose resulting in 50% cell growth inhibition) for the tocotrienol rich fraction or α-tocopherol nanostructured lipid carriers with or without simvastatin were determined by non-linear regression curve fit analysis using GraphPad Prism 5 from GraphPad Software, La Jolla, Calif. Differences among the various treatment groups in cell growth and viability studies were determined by analysis of variance (ANOVA) followed by Duncan's t-test. A difference of $p<0.05$ was considered to be significant as compared to vehicle-treated controls.

Figure 16A:
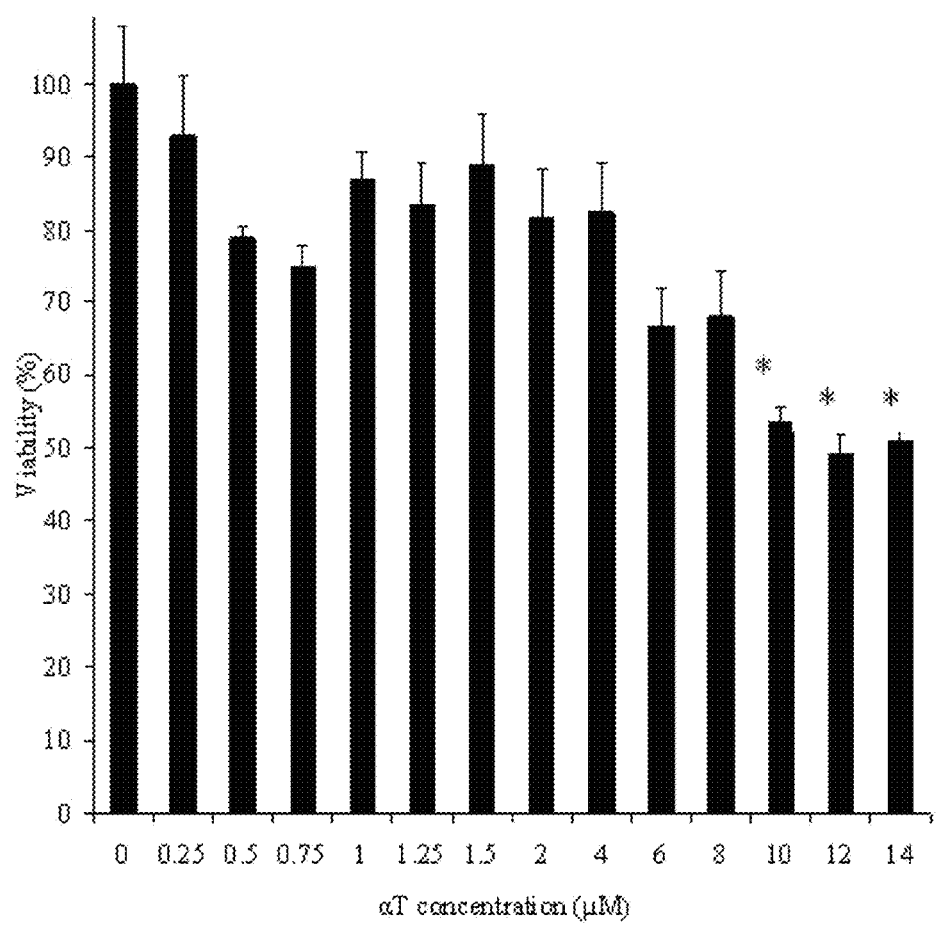
FIGS. 16A, 16B, 16C, and 16D show the anticancer effects on neoplastic +SA mammary epithelial cells of α-tocopherol nanostructured lipid carriers (16A), tocotrienol rich fraction nanostructured lipid carriers (16B), simvastatin/α-tocopherol nanostructured lipid carriers (16C), and simvastatin/tocotrienol rich fraction nanostructured lipid carriers (16D), respectively.
Figure 16B:
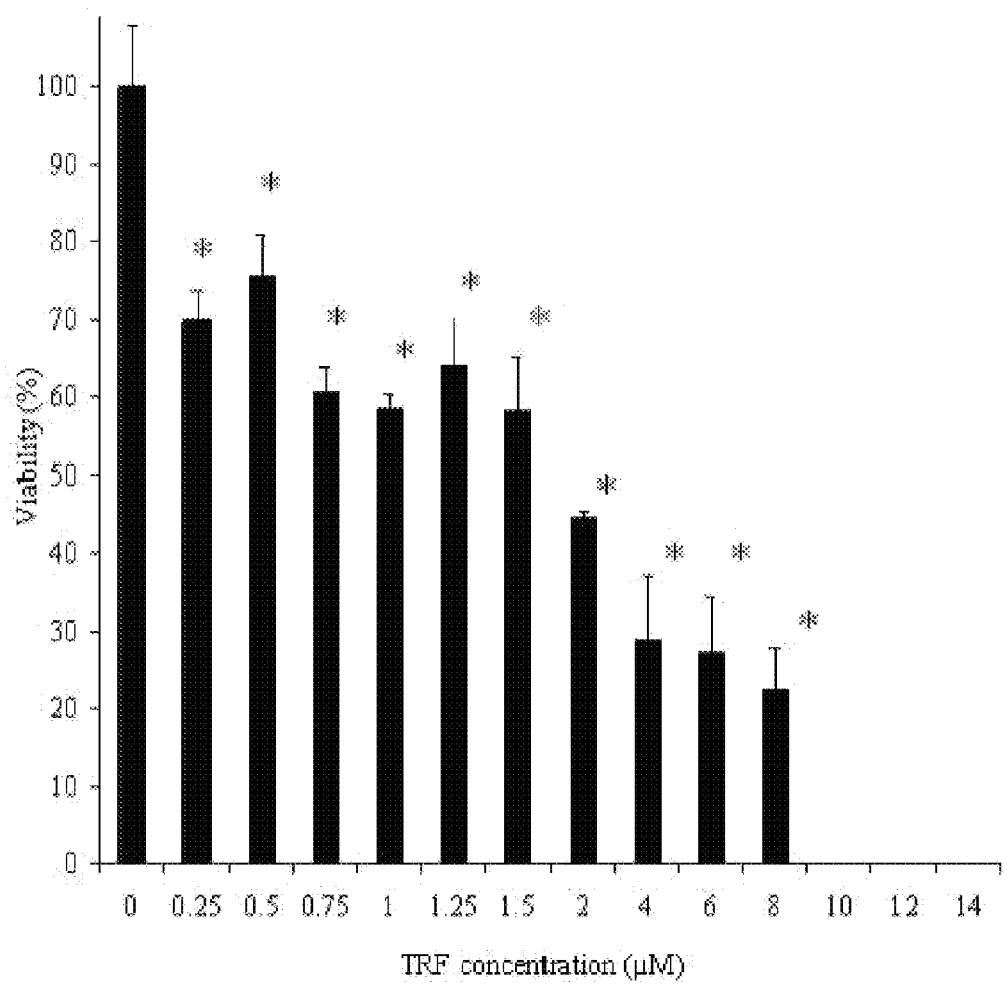
Figure 16C:
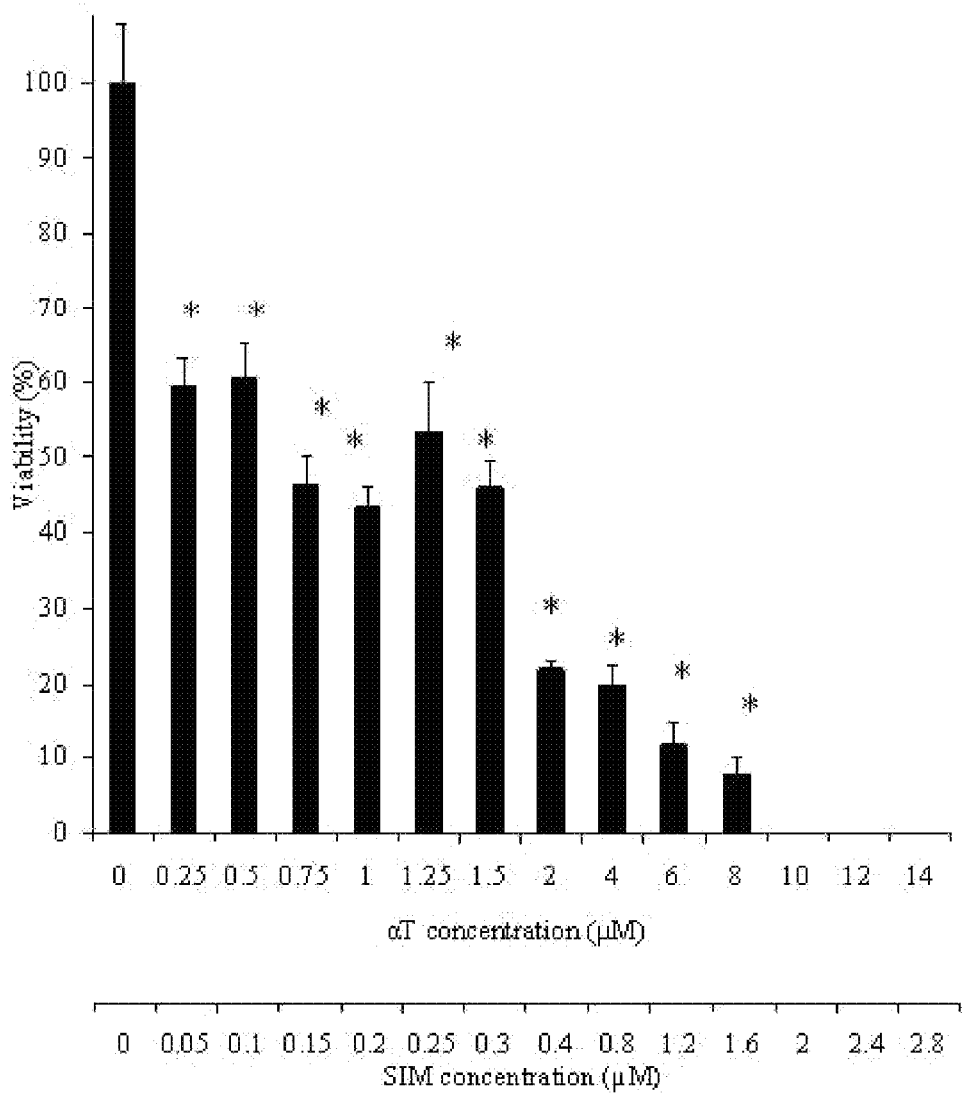
Figure 16D:
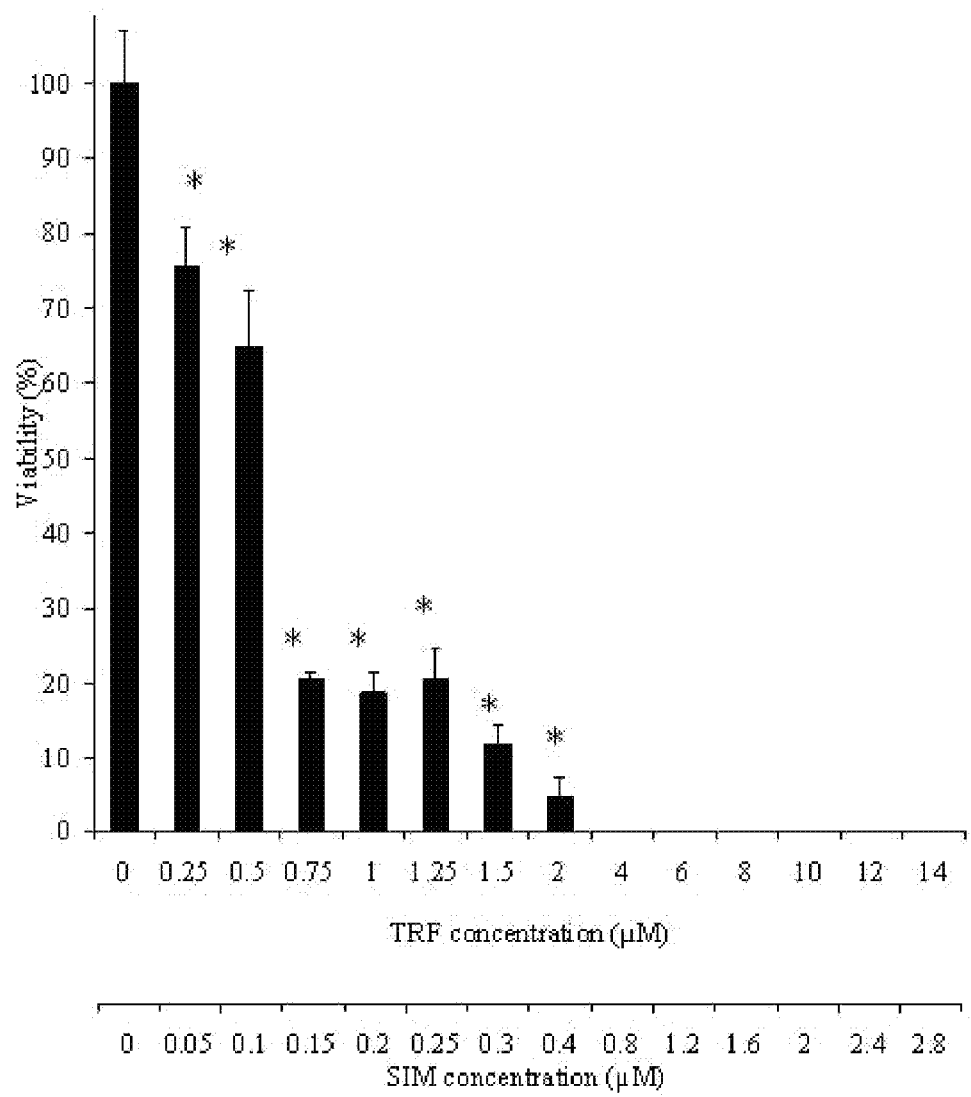

The antiproliferative effect of tocotrienol rich fraction and simvastatin against tumor cells when tested in vitro was further potentiated when simvastatin and tocotrienol rich fraction were combined in the same treatment, reflecting their synergistic activity against tumor cells. α-Tocopherol did not show antitumor activity at low concentrations, and therefore it was used as an inert ingredient to solubilize simvastatin in α-tocopherol based nanostructured lipid carriers. To confirm that the antiproliferation activity of tocotrienol rich fraction and simvastatin was retained when they were encapsulated within nanostructured lipid carriers, in vitro cell viability studies were carried out using neoplastic +SA mammary epithelial cells. The effects of nanostructured lipid carriers at various doses of α-tocopherol and tocotrienol rich fraction with or without simvastatin on cell proliferation over a 4 day culture period are shown in FIGS. 16A, 16B, 16C, and 16D. α-Tocopherol based nanostructured lipid carriers (FIG. 16A) did not exhibit any significant effect on cellular viability, when compared to the unloaded solid lipid nanoparticles (data not shown), indicating absence of cytotoxic effect. Addition of simvastatin to the α-tocopherol based nanostructured lipid carriers significantly inhibited +SA cell growth in a dose-responsive manner (FIG. 16C). Similarly, when α-tocopherol was substituted with tocotrienol rich fraction (FIG. 16B), the cellular viability decreased significantly as tocotrienol rich fraction treatment increased from 0.25 µM to 14 µM. The antiproliferative effect of the nanostructured lipid carriers was further potentiated when the cells were treated with simvastatin/tocotrienol rich fraction nanoparticles (FIG. 16D). FIGS. 16A, 16B, 16C, and 16D show the anticancer effects of α-tocopherol nanostructured lipid carrier (FIG. 16A), tocotrienol rich fraction nanostructured lipid carriers (FIG. 16B), simvastatin-α-tocopherol nanostructured lipid carriers (FIG. 16C), and simvastatin-tocotrienol rich fraction nanostructured lipid carriers (FIG. 16D) on neoplastic +SA mammary epithelial cells. Vertical bars in FIGS. 16A, 16B, 16C, and 16D indicate the mean cell count +SEM (n=6).

The antiproliferative effect of the nanostructured lipid carriers and the impact of tocotrienol rich fraction, simvastatin, and their combination on potentiating the effect of the nanoparticles could be deduced from their 50% growth inhibitory concentration ($IC_{50}$) values shown in Table VII below.

TABLE VII $IC_{50}$ values for the tocotrienol rich fraction or α-tocopherol nanostructured lipid carriers with or without simvastatin (mean ± SEM, n = 6)

| Formulation | $IC_{50}$ (µM) |
|---|---|
| simvastatin-tocotrienol rich fraction nanostructured lipid carrier | 0.52 ± 0.02[a] |
| simvastatin-α-tocopherol nanostructured lipid carrier | 0.76 ± 0.05[b] |
| tocotrienol rich fraction-nanostructured lipid carrier | 1.50 ± 0.12[a] |
| α-tocopherol-nanostructured lipid carrier | 17.70 ± 0.74[b] |

[a] The $IC_{50}$ values for the simvastatin-tocotrienol rich fraction nanostructured lipid carrier and tocotrienol rich fraction nanostructured lipid carrier represent the inhibitory concentration of tocotrienol rich fraction when the antiproliferative effect of the nanoparticles was tested with or without the presence of simvastatin, respectively.
[b] The $IC_{50}$ values for the simvastatin-α-tocopherol nanostructured lipid carrier and α-tocopherol nanostructured lipid carriers represent the inhibitory concentration of α-tocopherol when the antiproliferative effect of the nanoparticles was tested with or without the presence of simvastatin, respectively.

α-Tocopherol based nanostructured lipid carriers did not exhibit anticancer activity as evident from their high $IC_{50}$ value (17.7 µM). While treatment with high doses of α-tocopherol may induce anticancer effect, the delivery of such doses is impractical. In comparison, when α-tocopherol was replaced with tocotrienol rich fraction, $IC_{50}$ decreased significantly to 1.5 µM, which is less than the reported $IC_{50}$ value (6 µM) when cells were treated with tocotrienol rich fraction bound to bovine serum albumin. The lower $IC_{50}$ value of the tocotrienol rich fraction nanostructured lipid carrier, when compared to the albumin bound tocotrienol rich fraction, might be due to improved internalization of the nanostructured lipid carriers by endocytosis into the cells. Similarly, when simvastatin was added to the α-tocopherol based nanostructured lipid carriers, at a simvastatin to α-tocopherol ratio of 1:5, the $IC_{50}$ decreased to 0.76 µM, reflecting the cytotoxic effect of simvastatin against +SA mammary epithelial cells. Of most significance, however, was the observed decrease in cell viability and $IC_{50}$ (0.52 µM) when simvastatin and tocotrienol rich fraction were coencapsulated into nanoparticles at simvastatin to tocotrienol rich fraction ratio of 1:5, which demonstrated the potential therapeutic benefits of a combined simvastatin and tocotrienol rich fraction treatment.

Tocotrienol rich fraction and α-tocopherol were readily incorporated into nanostructured lipid carriers. However, simvastatin required the presence of a liquid microenvironment within the cores of the nanostructured lipid carrier to facilitate its dissolution. Therefore, the dissolution of 1 mM simvastatin required tocotrienol rich fraction or α-tocopherol at 50% substitution. This approach led to an approximately 100% entrapment efficiency. Once dissolved, a solid solution was formed in which simvastatin was molecularly dispersed in the binary blends of tocotrienol rich fraction (or α-tocopherol) with glyceryl behenate. Simvastatin dissolution was confirmed by differential scanning calorimetry and powder X-ray diffraction that showed the absence of endothermic or crystalline peaks, respectively. When placed in sink conditions, simvastatin nanostructured lipid carriers exhibited an initial burst release followed by a more gradual release. This might have been due to the high concentration of tocotrienol rich fraction (or α-tocopherol) in the nanoparticles, rendering them leakier than solid lipid nanoparticles made from solid cores. While simvastatin had no effect on particle size, tocotrienol rich fraction (or α-tocopherol) significantly reduced the size of the nanoparticles. Not wishing to be bound by theory, this may be attributed to the interaction between tocotrienol rich fraction (or α-tocopherol) with the solid lipid that resulted in a morphological change in the crystalline structure of glyceryl behenate accompanied by a more efficient particle packing. The data suggest that stable nanoparticles with high tocotrienol rich fraction and simvastatin loading could be readily prepared by the microemulsion technique. The viability of these nanoparticles for use in cancer therapy was confirmed when the antiproliferative effect of the nanostructured lipid carriers was evaluated against neoplastic +SA mammary epithelial cells. Not only was the antiproliferative effect of tocotrienol rich fraction and simvastatin retained, their activity was potentiated by their encapsulation into nanoparticles. Without wishing to be bound by theory, this could be attributed to enhanced cell binding or nanostructured lipid carrier internalization.

Example 2(J)

Drug Delivery

The compositions associated with examples 2(A)-2(K) may be delivered intravenously, intraperitoneally, subcutaneously, intramuscularly, ocularly, orally, transdermally, topically or by inhalation.

In a prophetic example, any of the individual compounds disclosed herein could be administered to a human patient having a need for cancer prevention or treatment by any one of the various known means of drug administration.

Example 2(K)

Composition Usage

In a prophetic example, the compositions described herein could be used for the purpose of treating medical conditions that have been shown to be treatable by statins including the treatment of cholesterol levels. In such treatments, any of the statins currently known to be efficacious could be used. Examples of such statins include atorvastatin, cerivastatin, fluvastatin, lovastatin, mevastatin, pitavastatin, pravastatin, rosuvastatin, and simvastatin.

The data associated with examples 2(A)-2(I) tends to indicate that many of the compositions disclosed herein are capable of causing enhanced cellular uptake of simvastatin and tocotrienol.

Examples 3(A)-3(F)

Nanostructured lipid carriers loaded with tocotrienol-rich-fraction of palm oil were prepared. The anti-proliferative effects of those nanostructured lipid carriers was evaluated against neoplastic +SA mammary epithelial cells. Methods and compositions relating to the preparation of the nanostructured lipid carriers were evaluated to determine the parameters affecting the properties of those nanostructured lipid carriers. In one embodiment of the invention nanoparticles were obtained from dispersions containing a surfactant to lipid ratio of about 0.5:1, with a total lipid concentration of about 0.25% w/v (0.0025 g/mL), from sonication at about 60% pulsar rate for about 10 minutes. The nanoparticles evaluated showed stability after several months of storage and exhibited potent anti-proliferative effect against neoplastic +SA mammary cells.

Solid lipid nanoparticles are aqueous colloidal dispersions with a diameter in the range of 50-1000 nm, the matrix of which is composed of biodegradable and biocompatible solid lipids. Unlike solid lipid nanoparticles, however, the cores of the nanostructured lipid carriers are composed of blends of lipids in which low melting-point lipids are entrapped in the form of oily nanocompartments within a solid matrix.

Several techniques have been used for the preparation of solid lipid nanoparticles and nanostructured lipid carriers such as high pressure homogenization, solvent emulsification/evaporation, and melt emulsification. Melt emulsification was used in the preparation of the nanostructured lipid carriers for the present evaluations. However, it is contemplated that other techniques could be used for commercial scale production. Homogenization of dispersions by ultrasound was used to prevent the occurrence of large particles (microparticles), which may result in batch polydispersity. The impact of process parameters such as sonication time, power and pulsar rate on the size and polydispersity of lipid nanoparticles was evaluated.

For Examples 3(A)-3(F) Cetyl palmitate (CET) (melting point: 45-55° C.) was purchased from TCI America (Portland, Oreg.); glyceryl tristearate (DYN), sold under the trademark Dynasan® 118, (melting point: 70-72° C.) was provided by Sasol Chemicals North America LLC (Houston, Tex.); glyceryl behenate (COMP), sold under the trademark Compritol® 888 ATO, (melting point: 71-74° C.), which is a mixture of ~15% mono-, 50% di- and 35% triglycerides of behenic acid, and glyceryl palmitostearate (PREC), sold under the trademark Precirol® ATO 5, (melting point: 53-56° C.) were provided by Gattefossé (Saint-Priest, Cedex, France). Poloxamer 188 is a compound arranged according the general formula described above. Poloxamer 188 is sold under the trade name Lutrol® F 68 NF, and was obtained from BASF (Florham Park, N.J.). The tocotrienol-rich-fraction of palm oil, which contains 20.2% α-tocopherol, 16.8% α-tocotrienol, 44.9% γ-tocotrienol, 14.8% δ-tocotrienol, and 3.2% of a non-vitamin E lipid soluble contaminants, was obtained from the Malaysian Palm Oil Board (Selangor, Malaysia); methylthiazolyldiphenyl tetrazolium bromide (MTT), bovine serum albumin (BSA), and other chemicals used in cell culture experiments were purchased from Sigma Chemical Company (St. Louis, Mo., USA); deionized water was obtained from NanoPure purification system. All chemicals were used as supplied without further modification.

Example 3(A)

Solid Lipid Nanoparticle Preparation

Unloaded solid lipid nanoparticles were prepared by a hot oil in water (o/w) microemulsion technique using high-shear homogenization in a manner similar to that described in "Optimization of Procedure Parameters and Physical Stability of Solid Lipid Nanoparticles in Dispersions" P. Ahlin, J. Kristl, J. Šmid-Kober, Acta Pharm 48, 257-267 (1998) with slight modifications. Glyceryl behenate was allowed to melt at 80° C., meanwhile in a separate vial, Poloxamer 188 was dissolved in purified water and then the Poloxamer 188 solution was heated to 80° C. The hot surfactant solution was then added to the molten glyceryl behenate under high-shear homogenization at 20,000 rpm using a homogenizer sold as the IKA® Ultra-Turrax T8 mixer by IKA® Works Inc., NC, USA. The concentration of glyceryl behenate, as the lipid phase, in the dispersion was 0.25% (w/v) whereas the surfactant to lipid ratio was 0.5:1. After 5 minutes, the o/w microemulsion was further processed by probe sonication using an ultrasonic homogenizer (Model 150VT, Biologics, Inc., Manassas, Va.). Sonication time and pulsar rate were adjusted according to the experimental design. During sonication, the temperature of the dispersions was recorded in real-time every 10 seconds using a digital dip probe (Traceable® thermometer Type K Rs 232, Calibration Control Company, Houston, Tex.) connected to a computer preloaded with a data acquisition software. After homogenization, solid lipid nanoparticles were formed by annealing the sonicated dispersions overnight at 4° C. To study the effect of formulation composition, unloaded solid lipid nanoparticles were prepared as described above with minor adjustments. Different solid lipid nanoparticles were prepared using one of the following four lipids as their lipid core: cetyl palmitate, glyceryl tristearate, glyceryl behenate, and glyceryl palmitostearate.

Example 3(B)

Sonication and Pulsar Rates

The effect of sonication time and pulsar rate on the diameter and distribution of unloaded (blank) solid lipid nanoparticles at a surfactant to lipid ratio of 0.5:1, with a total lipid concentration of 0.25 w/v were evaluated. These parameters were evaluated using a full factorial design which allowed for estimation of the optimal conditions for the production of solid lipid nanoparticles. A two-factor, three-level, full factorial design was applied to construct second order polynomial models, which were used to describe the effect of ultrasonic homogenization process parameters on the physical properties of unloaded solid lipid nanoparticles. The experimental design and the polynomial models were generated with the aid of Statgraphics Plus 5.1 software (SAS Inc., Minneapolis, Minn.). The following is the general formula for the models:

$$Y = A_0 + A_1 X_1 + A_2 X_2 + A_3 X_3 + A_4 X_1 X_2 + A_5 X_2 X_3 + A_6 X_1 X_3 + A_7 X_1^2 + A_8 X_2^2 + A_9 X_3^2 + E$$

where $A_0$-$A_9$ are the coefficients of the respective variables and their interaction terms, and E is an error term. The independent variables or factors were sonication time ($X_1$) and pulsar rate ($X_2$), which is the percent of time the sonicator is turned on and producing pulses. The dependent variables or responses were intensity-weighed mean particle size ($Y_1$), polydispersity index, denoted as PI ($Y_2$), and the change in the temperature of the dispersions during sonication, denoted as $\Delta T$ ($Y_3$). $\Delta T$ ($Y_3$) was estimated from the difference between the temperature of the dispersion at the beginning and end of sonication. PI describes the deviation of the measured autocorrelation function during particle size analysis from that of a monodisperse sphere dispersions with the same diameter.

Intensity-weighed mean particle size and the population distribution (polydispersity index, PI) of solid lipid nanoparticles and nanostructured lipid carriers were measured by photon correlation spectroscopy (PCS) at 25° C. and a fixed angle of 90° using Nicomp™ 380 ZLS submicron particle size analyzer (PSS Inc., Santa Barbara, Calif.). When needed, samples were diluted with a 0.2 μM filtered and deionized water. Analyses were performed in triplicates unless otherwise specified. The independent and dependent design variables are listed in Table VIII and the observed responses are given in Table IX.

TABLE VIII

The full factorial design summary: Independent and dependent design variables

| Independent variables | Units | Levels | | |
|---|---|---|---|---|
| | | Low | Medium | High |
| $X_1$: Time | Minutes | 2.0 | 6.0 | 10.0 |
| $X_2$: Pulsar rate | % | 30.0 | 60.0 | 90.0 |

| Dependent variables | Units | Observed Responses | |
|---|---|---|---|
| | | Minimum | Maximum |
| $Y_1$: Particle size | nm | 113.6 | 578.9 |
| $Y_2$: Polydispersity index (PI) | N/A | 0.25 | 0.45 |
| $Y_3$: Change in Temperature ($\Delta T$) | ° C. | 1.6 | 13.0 |

TABLE IX

Experimental runs and the observed responses for the full factorial design (mean ± SD, n = 3)

| Run | Time (min) $X_1$ | Pulsar rate (%) $X_2$ | Particle size (nm) $Y_1$ | Polydispersity index (PI) $Y_2$ | Temperature change ($\Delta T$) $Y_3$ |
|---|---|---|---|---|---|
| 1 | 6 | 60 | 116.1 ± 1.0 | 0.26 ± 0.00 | 5.9 |
| 2 | 6 | 30 | 379.9 ± 5.5 | 0.45 ± 0.02 | −5.8 |
| 3 | 10 | 30 | 334.5 ± 5.4 | 0.37 ± 0.05 | −6.0 |
| 4 | 2 | 90 | 163.3 ± 2.0 | 0.38 ± 0.01 | 4.4 |
| 5 | 2 | 60 | 258.2 ± 4.8 | 0.43 ± 0.02 | 1.6 |
| 6 | 10 | 60 | 110.5 ± 0.9 | 0.25 ± 0.01 | 7.3 |
| 7 | 10 | 90 | 107.1 ± 2.5 | 0.26 ± 0.02 | 13.0 |
| 8 | 6 | 90 | 106.9 ± 1.6 | 0.26 ± 0.03 | 10.7 |
| 9 | 2 | 30 | 578.9 ± 10.8 | 0.40 ± 0.01 | −1.9 |
| 10 | 6 | 60 | 113.6 ± 2.6 | 0.27 ± 0.03 | 4.8 |

Responses, $Y_1$, $Y_2$, and $Y_3$ were initially analyzed by analysis of variance (ANOVA) and lack-of-fit tests to determine whether the quadratic model fit the data. Results of model analysis and lack of fit tests are given in Tables X(a)-X(c). The quadratic model was statistically significant for $Y_1$ and $Y_3$ (p<0.0001 and p=0.003, respectively). Furthermore, the lack of fit test was insignificant (p>0.05) for $Y_1$ and $Y_3$ indicating that the quadratic model adequately fits the data for both responses. Solid lipid nanoparticles formulations with significantly smaller PI were not obtained by manipulating $X_1$ and $X_2$. The quadratic model was found to be statistically insignificant (p=0.0625) and the sonication process parameters had an insignificant effect (p>0.05) on PI, which varied from 0.25 to 0.45 (Table VIII). The PI of all formulations was equal to or less than approximately 0.4. Overall, the observed PI values smaller than 0.40 indicated a particle size distribution that were near monomodal and values of <0.35 indicating even better monomodal particle size distribution.

Figure 18:
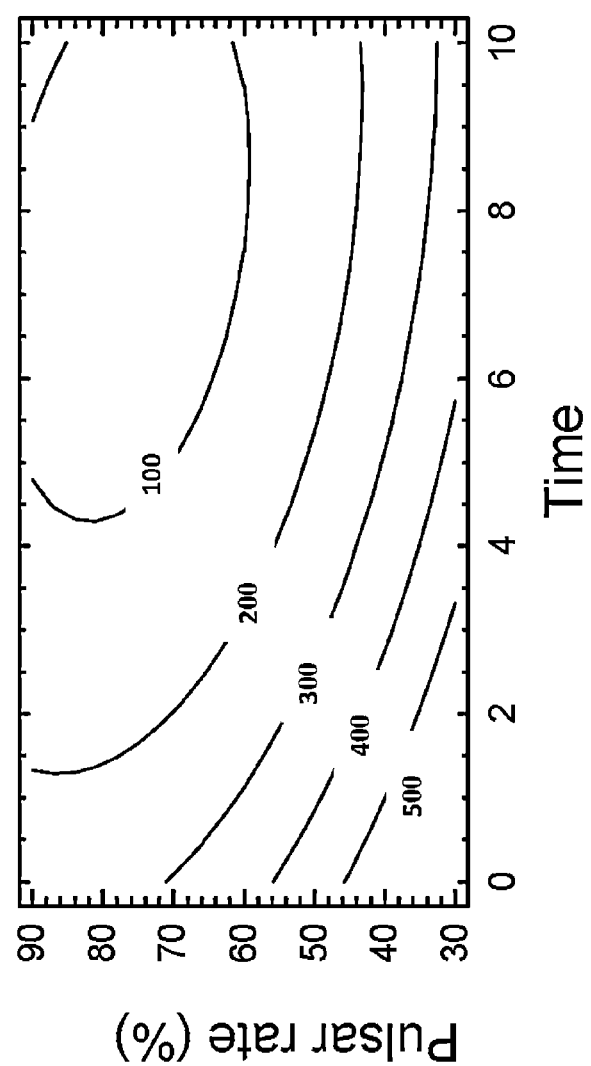
FIG. 18 shows the particle size measured in nanometers as a function of the time of sonication in minutes and the pulsar rate from the evaluation of sonication variables.
Figure 19:
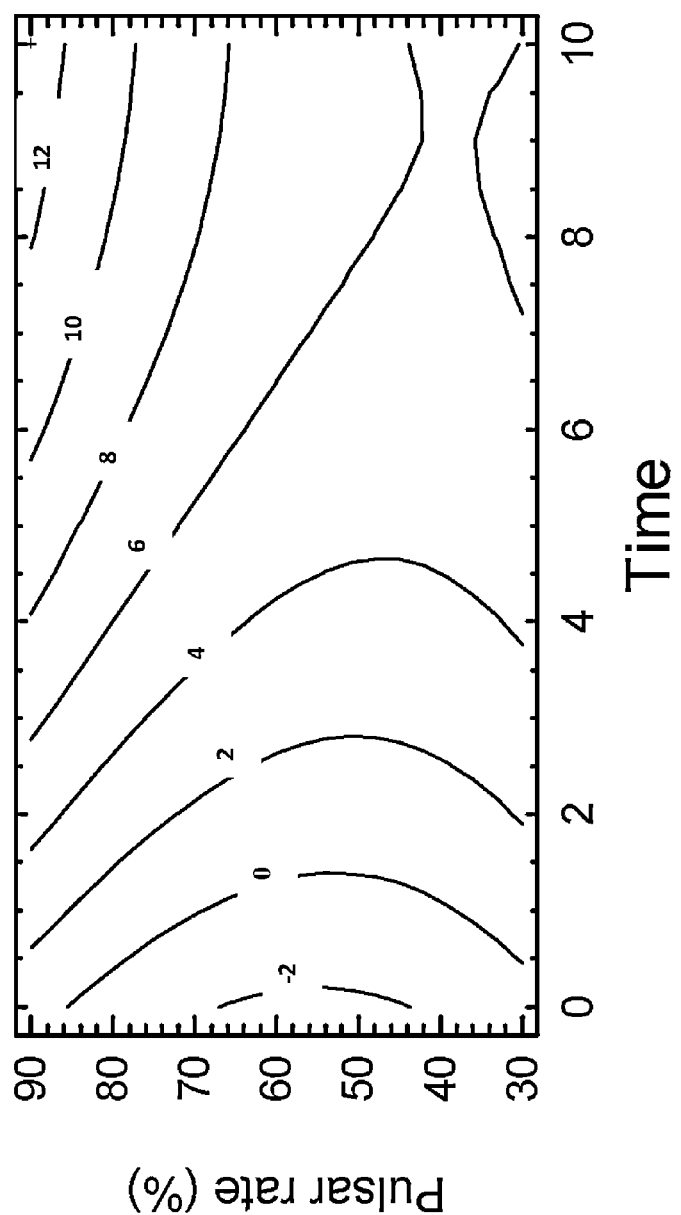
FIG. 19 shows a contour plot from the evaluation of sonication variables of the change in temperature measured in degrees Celsius versus the time of sonication in minutes and the pulsar rate.

The following second order polynomial equations were constructed and used to generate the contour plots shown in FIG. 18 and FIG. 19. FIG. 18 shows the particle size measured in nanometers as a function of the time of sonication in minutes and the pulsar rate. FIG. 19 shows a contour plot of the change in temperature measured in degrees Celsius as a function of the time of sonication in minutes and the pulsar rate. These equations represent the quantitative effect of process variables ($X_1$ and $X_2$) and their interactions on the responses $Y_1$ and $Y_3$:

$$Y_1 = 1288.29 - 87.06X_1 - 23.29X_2 + 3.74X_1^2 + 0.39X_1X_2 + 0.13X_2^2$$

$$Y_3 = -12.52 - 0.39X_2 + 0.026X_1X_2$$

$X_1$ is the sonication time and $X_2$ is pulsar rate. Terms with insignificant p-values were excluded from the equation. The significant effect of each factor in the quadratic model is given in tables X(a)-X(c). A value of p<0.05 for any factor in analysis of variance (ANOVA) indicates a significant influence of the corresponding factors on the response. As shown in the tables X(a)-X(b) pulsar rate had a significant effect on both responses, whereas sonication time had a significant effect on particle size and an insignificant effect (p>0.05) on the change in temperature of the dispersions. The coefficient estimates for $X_1$ and $X_2$ are related to the effect of these variables. A positive value represents an effect that favors the response, while a negative value indicates an antagonistic effect.

TABLE X(a)

Analysis of variance (ANOVA) for the response $Y_1$.

| Source | Sum of Squares | DF* | Mean Square | F-Ratio | Regression coefficient | P value | |
|---|---|---|---|---|---|---|---|
| Model | 484.9 | 5 | 96.9866 | 99.64 | | <0.0001 | Significant |
| Lack of fit | 4.3 | 4 | 1.06540 | 1.760 | | 0.5069 | Non-significant |

TABLE X(a)-continued

Analysis of variance (ANOVA) for the response $Y_1$.

| Source | Sum of Squares | DF* | Mean Square | F-Ratio | Regression coefficient | P value | |
|---|---|---|---|---|---|---|---|
| $X_1$: Time | 33495.5 | 1 | 33495.5 | 140.5 | −87.065 | 0.0003 | Significant |
| $X_2$: Pulser | 139843.0 | 1 | 139843 | 586.6 | −23.290 | <0.0001 | Significant |
| $X_1 \cdot X_1$ | 8348.08 | 1 | 8348.10 | 35.00 | 3.7384 | 0.0041 | Significant |
| $X_1 \cdot X_2$ | 8854.81 | 1 | 8854.80 | 37.10 | 0.3921 | 0.0037 | Significant |
| $X_2 \cdot X_2$ | 32967.0 | 1 | 32967.0 | 138.3 | 0.1321 | 0.0003 | Significant |
| Total error | 953.6 | 4 | 238.400 | | | | |

*DF: Degrees of freedom

TABLE X(b)

Analysis of variance (ANOVA) for the response $Y_2$.

| Source | Sum of Squares | DF | Mean Square | F-Ratio | Regression coefficient | P value | |
|---|---|---|---|---|---|---|---|
| Model | 0.0408 | 5 | 0.0081 | 5.46 | | 0.0625 | Non-significant |
| Lack of fit | 0.0058 | 3 | 0.0019 | 13.5 | | 0.1970 | Non-significant |
| $X_1$: Time | 0.0187 | 1 | 0.0187 | 5.90 | −0.03020 | 0.0721 | Non-significant |
| $X_2$: Pulser | 0.0171 | 1 | 0.0171 | 5.40 | −0.00063 | 0.0805 | Non-significant |
| $X_1 \cdot X_1$ | 0.0028 | 1 | 0.0028 | 0.90 | 0.00210 | 0.3962 | Non-significant |
| $X_1 \cdot X_2$ | 0.0016 | 1 | 0.0016 | 0.50 | −0.00016 | 0.5167 | Non-significant |
| $X_2 \cdot X_2$ | 0.0041 | 1 | 0.0041 | 1.30 | 0.00004 | 0.3182 | Non-significant |
| Total error | 0.0126 | 4 | 0.0031 | | | | |

*DF: Degrees of freedom

TABLE X(c)

Analysis of variance (ANOVA) for the response $Y_3$.

| Source | Sum of Squares | DF | Mean Square | F-Ratio | Regression coefficient | P value | |
|---|---|---|---|---|---|---|---|
| Model | 364.30 | 5 | 72.860 | 29.4 | | 0.003 | Significant |
| Lack of fit | 9.2972 | 3 | 3.0990 | 5.12 | | 0.3115 | Non-significant |
| $X_1$: Time | 17.340 | 1 | 17.340 | 7.00 | −0.8410 | 0.0572 | Non-significant |
| $X_2$: Pulser | 291.21 | 1 | 291.21 | 118 | 0.3972 | 0.0004 | Significant |
| $X_1 \cdot X_1$ | 0.4285 | 1 | 0.4290 | 0.20 | −0.0267 | 0.6987 | Non-significant |
| $X_1 \cdot X_2$ | 40.323 | 1 | 40.323 | 16.3 | 0.0264 | 0.0157 | Significant |
| $X_2 \cdot X_2$ | 13.761 | 1 | 13.761 | 5.60 | −0.0026 | 0.0779 | Non-significant |
| Total error | 9.9023 | 4 | 2.4750 | | | | |

*DF: Degrees of freedom

The effects of sonication time and pulsar rate on the intensity-weighed particle size is illustrated in the contour plot in FIG. 18. When samples were subjected to ultrasonic homogenization for 2 minutes, particle size decreased from 578 to 163 nm when pulsar rate was raised from 30% to 90%. Similarly, when the samples were homogenized for 10 minutes, particle size decreased from 334 to 107 nm when pulsar rate was raised from 30% to 90%.

During sonication heat is generated from the vibrations brought by the ultrasonic waves. Heat generated during sonication may play a secondary role in reducing particle size by maintaining the temperature of the dispersion above the melting point of the lipid. The temperature of the dispersions was measured in real-time and ΔT was calculated from the temperature readings at the beginning and end of each sonication cycle. The effect of sonication time and pulsar rate on ΔT is illustrated in FIG. 19 and Table IX. When samples were subjected to ultrasonic homogenization for 2 minutes, ΔT increased from −1.9 to 4.4° C. when pulsar rate was raised from 30% to 90%. Similarly, when the samples were homogenized for 10 minutes, ΔT increased from −6.0 to 13.0° C. when pulsar rate was raised from 30% to 90%. While a direct relationship could not be established between ΔT and particle size, it was apparent by observing FIGS. 18 and 19, that solid lipid nanoparticles dispersions in which heat was generated during sonication had smaller particle sizes.

All preparations had a mean particle size ranging from 107 to 578 nm. By visually inspecting FIG. 18, pulsar rates of 60% and greater yielded particle sizes within a desirable range. Since time had an insignificant effect on temperature but a significant effect on particle size, a time of 10 minutes was selected for subsequent use. Ultrasonic homogenization for 10 minutes at 60% pulsar rate was selected for the preparations of solid lipid nanoparticles and nanostructured lipid carriers for evaluation in the subsequent studies.

Example 3(C)

Surfactant to Lipid Ratios

The effect of lipid composition and lipid to surfactant ratio on the size and polydispersity of the nanoparticles was evaluated. Therefore, the effects of four lipids; glyceryl tristearate, glyceryl behenate, glycerol palmitostearate, and cetyl palmitate; and their proportion in the solid lipid nanoparticles on the physical properties of the solid lipid nanoparticles were evaluated in this study.

Figure 20:
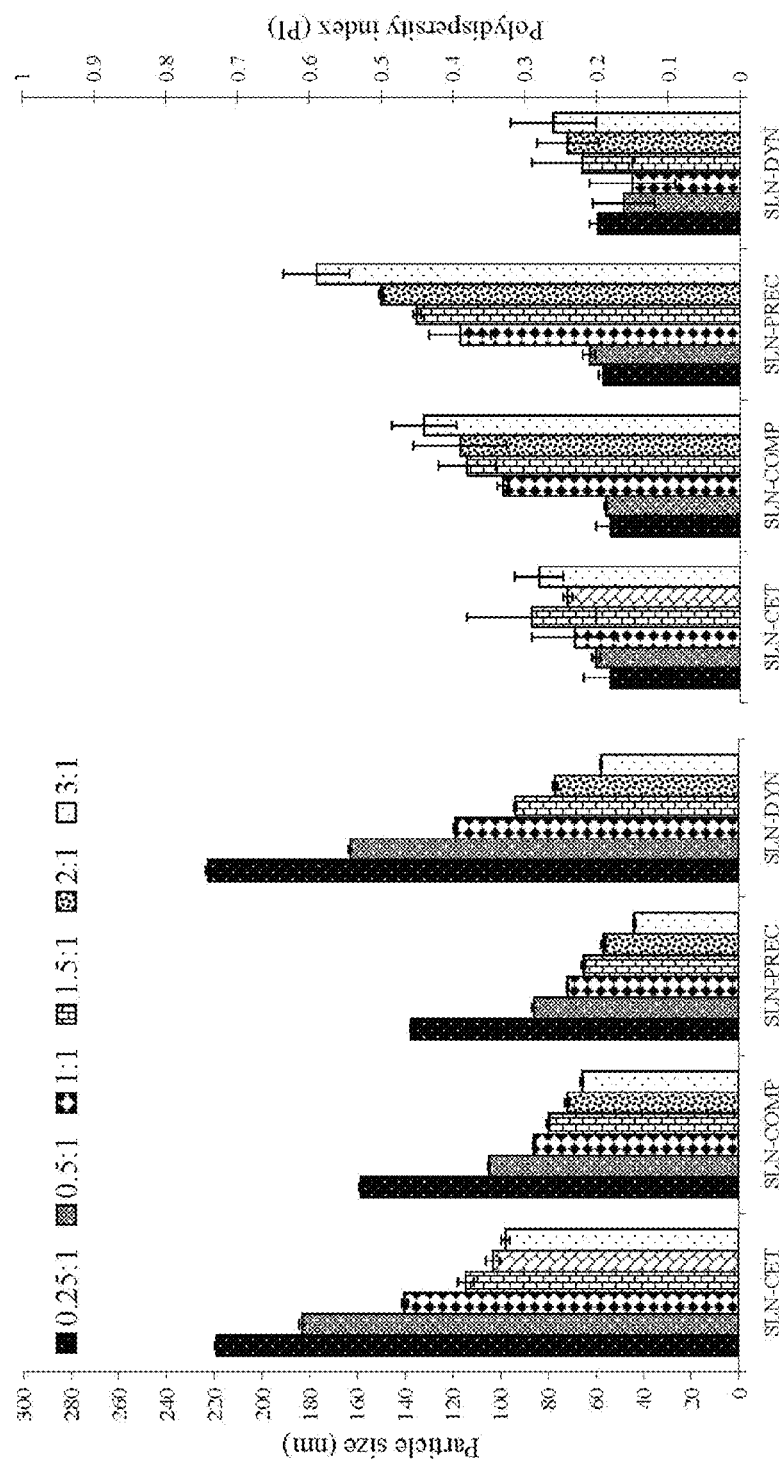
FIG. 20 shows the mean particle diameter and polydispersity index (PI) for various surfactant to lipid ratios using glycerol tristearate, glyceryl behenate, glycerol palmitostearate, and cetyl palmitate used in the creation of nanoparticles.

The effect of surfactant (poloxamer 188) concentration on solid lipid nanoparticles size and PI was evaluated by varying the surfactant to lipid ratio from 0.25:1 to 3:1 while maintaining the concentration of the lipid phase constant at 0.25% w/v of the dispersion. Solid lipid nanoparticles were prepared as described above using the ultrasonication parameters that were identified in the sonication tests. FIG. 20 shows the mean particle size and polydispersity index (PI) for various surfactant to lipid ratios using glycerol tristearate, glyceryl behenate, glycerol palmitostearate, and cetyl palmitate. In FIG. 20 the vertical bars indicate the average value with lines indicating plus or minus one standard deviation. As seen in FIG. 20, the size of the solid lipid nanoparticles significantly decreased ($p<0.05$) with an increase in the surfactant to lipid ratio. Nonetheless, PI was also found to increase with an increase in the surfactant to lipid ratio, which could be attributed to the bridging between the nanoparticles caused by higher poloxamer concentration and their subsequent aggregation and/or coalescence. A surfactant to lipid ratio of 0.5:1 was selected for subsequent evaluation based on a comparison of the particle size, the PI, and a consideration of potential cytotoxic effects of the surfactant. At this ratio, all solid lipid nanoparticles had a particle size of less than 200 nm with a PI of less than 0.3, which was suitable for sterilization by filtration prior to performing cell culture studies.

Example 3(D)

Lipid Concentrations

Figure 21:
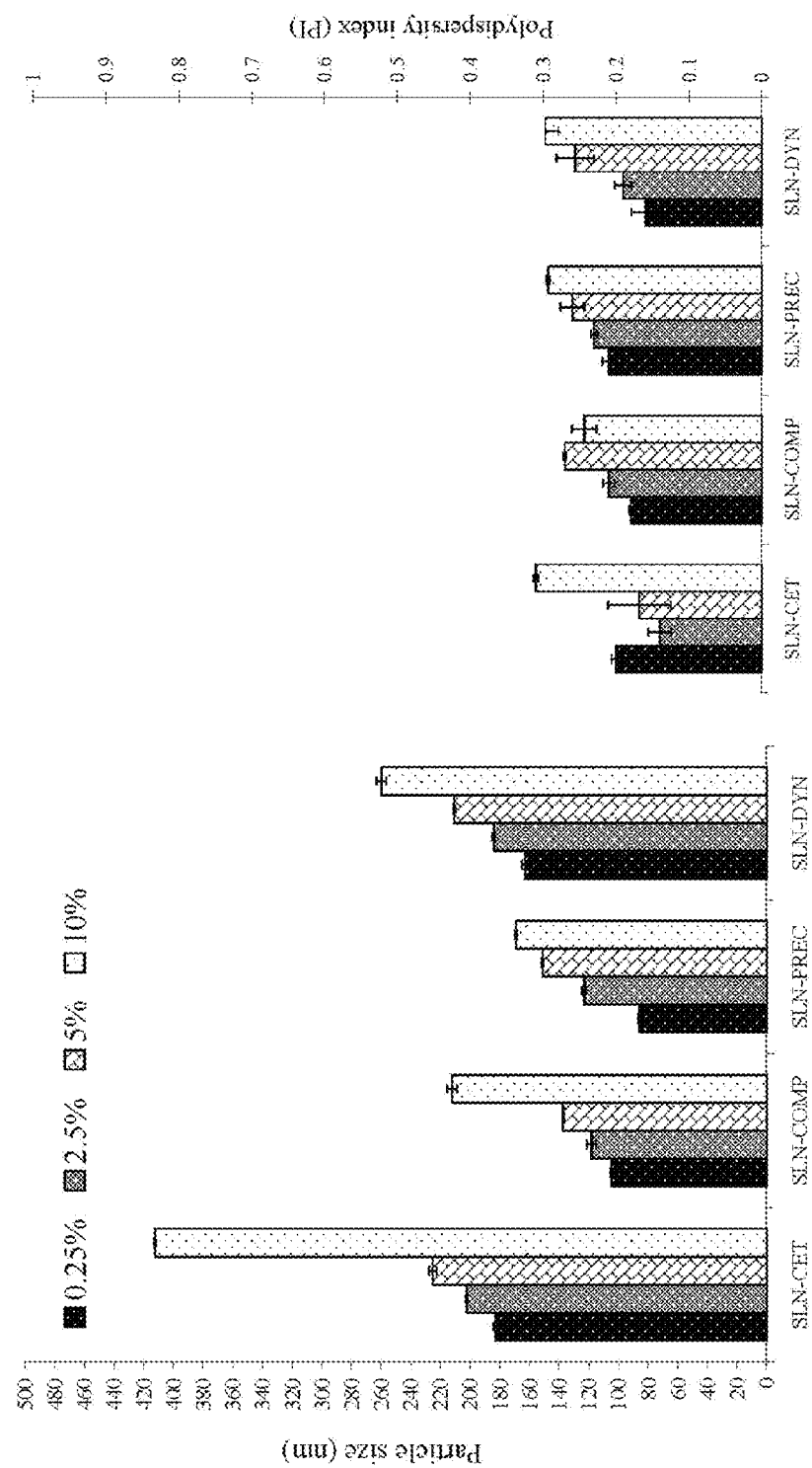
FIG. 21 shows the effect of total lipid concentration in the dispersions used to create the particles on the particle size and polydispersity index (PI) for the unloaded solid lipid nanoparticles.

The ratio of the surfactant (poloxamer 188) to the lipid was maintained constant at 0.5:1, and only the total lipid concentration was raised from 0.25% to 10% w/v of the aqueous dispersion. FIG. 21 shows particle size and polydispersity index (PI) for the unloaded solid lipid nanoparticles showing the effect of total lipid concentration in the dispersions. Vertical bars indicate the average value and lines indicate plus or minus one standard deviation. The particle size of the nanoparticles increased with an increase in lipid concentration from 0.25% to 10%. More precisely, the mean particle size increased from 85 to 169 nm, from 104 to 212 nm, from 162 to 259 nm, and from 183 to 412 nm for solid lipid nanoparticles prepared from glyceryl palmitostearate, glyceryl behenate, glyceryl tristearate, and cetyl palmitate, respectively. While solid lipid nanoparticles with a particle size of approximately 100 nm were only obtained when glyceryl behenate and glyceryl palmitostearate were used, all solid lipid nanoparticles prepared at a lipid concentration of 0.25% had a particle size of less than 200 nm. Accordingly, in subsequent studies a concentration of 0.25% was used. Furthermore, unlike particle size, PI only marginally increased to a maximum value of 0.31 for solid lipid nanoparticles-cetyl palmitate, which remains below the 0.35.

Example 3(E)

Stability Tests

The tocotrienol-rich-fraction was incorporated into lipid nanoparticles using the process conditions and formulation composition determined above. The long term stability of the tocotrienol-rich-fraction nanostructured lipid carriers was evaluated with respect to particle diameter.

Figure 22:
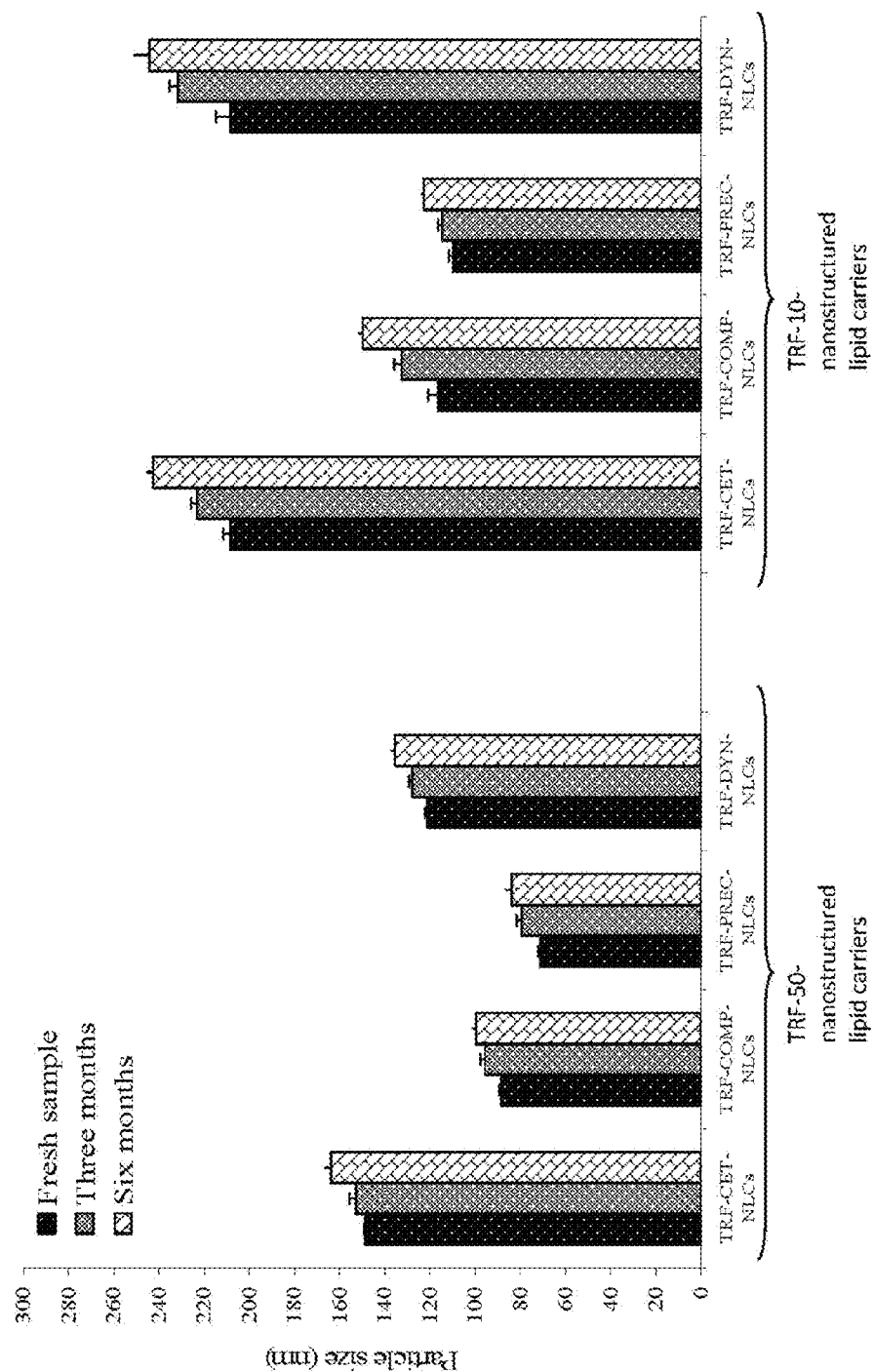
FIG. 22 shows the effect of storage time at controlled room temperature (20-25)° C. on particle diameter of tocotrienol-rich-fraction-50-nanostructured lipid carriers and tocotrienol-rich-fraction-10-nanostructured lipid carriers.

Using the process and formulation parameters selected above, the tocotrienol-rich-fraction was incorporated into solid lipid nanoparticles by substituting 10% (for tocotrienol-rich-fraction-10-nanostructured lipid carriers) or 50% (for tocotrienol-rich-fraction-50-nanostructured lipid carriers) of the lipid phase with tocotrienol-rich-fraction. Tocotrienol-rich-fraction entrapment within solid lipid nanoparticles to form nanostructured lipid carriers was verified by HPLC analysis. Even after one month of storage at controlled room temperature, measurements indicated 90-110% of tocotrienol-rich-fraction was retained within the nanostructured lipid carriers, which also reflected good chemical stability of the nanoparticles. For physical stability, the particle size of the tocotrienol-rich-fraction-nanostructured lipid carriers was measured for samples freshly prepared and after storage for 3 and 6 months at controlled room temperature and protected from light. FIG. 22 shows the effect of storage time at controlled room temperature (20-25)° C. on particle size of tocotrienol-rich-fraction-50-nanostructured lipid carriers and tocotrienol-rich-fraction-10-nanostructured lipid carriers. Vertical bars indicate the average value with lines indicating plus or minus a single standard deviation. The particle size of the tocotrienol-rich-fraction-nanostructured lipid carriers did not significantly change after storage ($p>0.05$) when compared to the freshly prepared samples. After 6 months, the average size of the nanoparticles marginally increased from 148 to 163 nm, from 88 to 99 nm, from 71 to 83 nm, and from 121 to 135 nm for tocotrienol-rich-fraction-50-nanostructured lipid carriers made from cetyl palmitate, glyceryl behenate, glyceryl palmitostearate, and glyceryl tristearate, respectively. Similarly, the average particle size increased from 208 to 242 nm, from 110 to 149 nm, from 109 to 122 nm, and from 208 to 244 nm for tocotrienol-rich-fraction-10-nanostructured lipid carriers made with cetyl palmitate, glyceryl behenate, glyceryl palmitostearate, and glyceryl tristearate, respectively. These results reflected good long-term stability of the nanoparticles, which was further confirmed by particle size homogeneity and the absence of visible phase separation.

Intensity-weighed mean particle size and population distribution of the samples were measured at different time intervals by PCS as described above. To overrule the possibility of tocotrienol-rich-fraction decomposition or loss during preparation or storage, tocotrienol-rich-fraction-nanostructured lipid carriers dispersions were subjected to HPLC analysis. Tocotrienol-rich-fraction concentration was quantified in these dispersions by a validated reversed-phase HPLC method reported in "Development and validation of a reversed-phase HPLC method for the simultaneous analysis of simvastatin and tocotrienols in combined dosage forms, Journal of pharmaceutical and biomedical analysis" by H. Ali, S. Nazzal, 49 (4), 950-6 (2009). 50 µL of each tocotrienol-rich-fraction-nanostructured lipid carriers dispersion was first mixed with 5 mL methanol and then centrifuged at 5000 rpm for 15 minutes prior to analysis. The methanolic tocotrienol-rich-fraction solutions were then injected into a C18 (4.6×100 mm) monolithic analytical column (sold under the trademark Onyx® by Phenomenex®, Inc., Torrance, Calif.) supported by a HPLC (sold under the trademark SpectraSystem by Thermo Electron Corporation, San Jose, Calif.) equipped with a UV3000 UV/Visible variable wavelength detector. Detection of tocotrienol-rich-fraction was carried out at $\lambda_{max}$=295 nm. A 5% v/v water in methanol solution was used as the mobile phase, which was allowed to run at a flow rate of 0.8 mL/min. Data acquisition was performed using chromatography software sold under the trademark ChromQuest™ by Thermo Electron Corporation, San Jose, Calif. (version 4.2).

Example 3(F)

Cell Cultures

Tocotrienol-rich-fraction was incorporated into lipid nanoparticles using the process conditions and formulation composition determined above. The tocotrienol-rich-fraction nanostructured lipid carriers were evaluated to assess the cellular anti-proliferative affect of tocotrienol-rich-fraction-nanostructured lipid carriers against neoplastic +SA mammary epithelial cells.

For the anti-proliferation studies, tocotrienol-rich-fraction-nanostructured lipid carriers were prepared by substituting either 10% (for tocotrienol-rich-fraction-10-nanostructured lipid carriers) or 50% (for tocotrienol-rich-fraction-50-nanostructured lipid carriers) of the lipid phase in the solid lipid nanoparticles with tocotrienol-rich-fraction. The surfactant to lipid ratio was maintained constant at 0.5:1. The concentration of the lipid phase, which included tocotrienol-rich-fraction, however, was adjusted so that the concentration of tocotrienol-rich-fraction in the dispersions was 1 mM, which is also equivalent to a total lipid concentration of 1.25% and 0.25% w/v for tocotrienol-rich-fraction-10-nanostructured lipid carriers and tocotrienol-rich-fraction-50-nanostructured lipid carriers, respectively.

Highly malignant +SA mammary epithelial cells were used to evaluate anti-proliferative effects. This cell line was derived from an adenocarcinoma that developed spontaneously in a BALB/c female mouse. The +SA cell line is characterized as being highly malignant, estrogen-independent, and displays anchorage-independent growth when cultured in soft agarose gels. When +SA cells are injected back into the mammary gland fat pad of syngeneic female mice, they form rapidly growing anaplastic adenocarcinomas that are highly invasive and metastasize to the lung. The cell culture and experimental procedures used in this study were previously described in "Anti-proliferative and apoptotic effects of tocopherols and tocotrienols on preneoplastic and neoplastic mouse mammary epithelial cells," B. S. McIntyre, K. P. Briski, A. Gapor, and P. W. Sylvester, Proceedings of the Society for Experimental Biology and Medicine, Society for Experimental Biology and Medicine, New York, N.Y. 224 (4), 292-301 (2000). Cells were grown and maintained in serum-free medium sold as Dulbecco's modified Eagle's (DMEM)/F12 control media containing 5 mg/mL bovine serum albumin (BSA), 10 µg/mL transferrin, 100 µg/mL soybean trypsin inhibitor, and 100 U/mL penicillin and 100 µg/mL streptomycin, 10 µg/mL insulin, and 10 ng/mL epidermal growth factor (EGF) as a mitogen. Cells were maintained at 37° C. in a humidified atmosphere of 95% air and 5% $CO_2$.

Viable cell number was determined using the 3-(4,5-dimethylthiazol-2yl)-2,5-diphenyl tetrazolium bromide (MTT) colorimetric assay. Briefly, at the end of the treatment period, media in all treatment groups was removed and replaced with fresh control media containing 0.42 mg/mL MTT, and the cells were returned to the incubator for a period of 4 hours. At the end of the incubation period, the media was removed, the MTT crystals were dissolved in 1 mL of isopropanol, and the optical density of each sample was read at 570 nm on a microplate reader (SpectraCount, Packard BioScience Company, Meriden, Conn.). Cell number was calculated against a standard curve prepared by plating known concentrations of cells, as determined by the hemocytometer, at the start of each experiment.

For the cell culture experiments, freshly prepared solid lipid nanoparticles, tocotrienol-rich-fraction/BSA, and tocotrienol-rich-fraction-nanostructured lipid carriers stock formulations were filtered through either 0.22 or 0.45 µM sterile syringe filters. These stock formulations were then added to the culture media at various concentrations to prepare the unloaded solid lipid nanoparticles or tocotrienol-rich-fraction supplemented treatment media. Each time, the media was freshly prepared just before the treatment. The sterile stock formulations were stored at 4° C. throughout the duration of the experiment.

+SA cells were initially plated at a density of $5 \times 10^4$ cells/well (6 wells/group) in serum-free defined control media in 24-well culture plates and allowed to adhere overnight. The following day, cells were divided into different treatment groups and the media was removed and replaced with fresh control or treatment media, and then returned to the incubator. Cells in their respective treatment groups were fed fresh media every other day throughout experimentation. $IC_{50}$ (dose resulting in 50% cell growth inhibition) values for tocotrienol-rich-fraction/BSA, tocotrienol-rich-fraction-50-nanostructured lipid carriers, and tocotrienol-rich-fraction-10-nanostructured lipid carriers, were determined by non-linear regression curve fit analysis using GraphPad Prism 5 from GraphPad Software, La Jolla, Calif. Differences among the various treatment groups in cell growth and viability studies were determined by analysis of variance (ANOVA) followed by Duncan's t-test. A difference of $p<0.05$ was considered to be significant.

Figure 23:
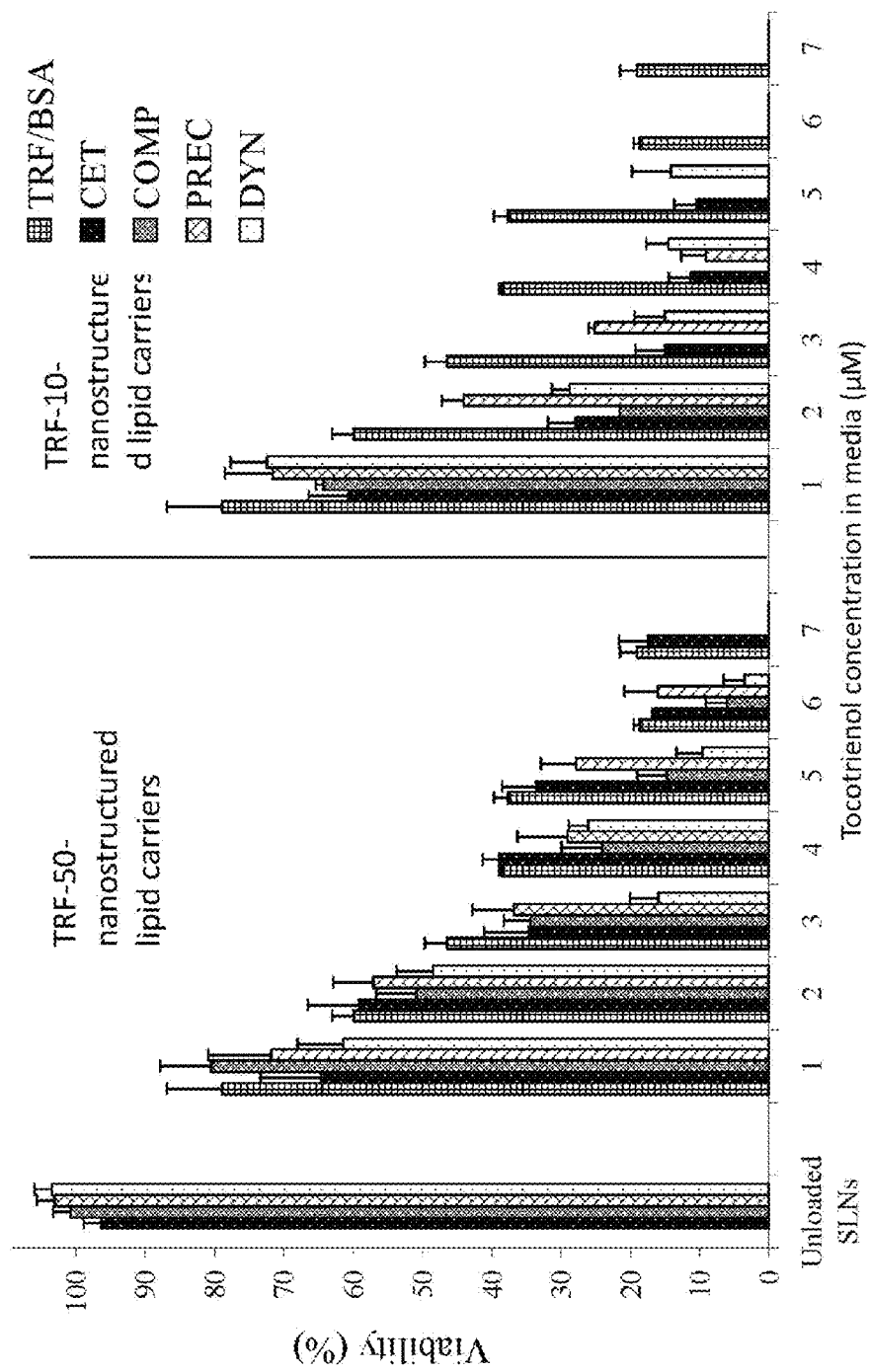
FIG. 23 shows the anti-proliferative effects of unloaded solid lipid nanoparticles as compared to tocotrienol-rich-fraction-nanostructured lipid carriers at 10% and 50% tocotrienol-rich-fraction load of the total lipid phase, and tocotrienol-rich-fraction/BSA on neoplastic +SA mammary epithelial cells.

FIG. 23 shows the anti-proliferative effects of unloaded solid lipid nanoparticles, and tocotrienol-rich-fraction-nanostructured lipid carriers at 10% and 50% tocotrienol-rich-fraction load of the total lipid phase on neoplastic +SA mammary epithelial cells. Also shown is the anti-proliferative effect of the tocotrienol-rich-fraction/BSA solution as a reference. Cells were initially plated at a density of $5 \times 10^4$ cells/well (6 wells/group) in 24-well plates and exposed to formulation-supplemented media for a 4-day treatment period. Vertical bars indicate the mean cell count with lines indicating the standard error of the mean. The concentration of the lipid phase in solid lipid nanoparticles when cells were treated with the unloaded solid lipid nanoparticles was equivalent to the concentration of the lipid phase of the nanostructured lipid carriers when cells were treated with the highest dose of tocotrienol-rich-fraction. Even at this level, unloaded solid lipid nanoparticles did not show any significant effect (p>0.05) on cell proliferation. The viability of the cells was above 95%, which suggested negligible effect on cell viability and the suitability of the solid lipid nanoparticles as drug carriers. Conversely, the cellular viability after treatment with tocotrienol-rich-fraction/BSA and tocotrienol-rich-fraction-nanostructured lipid carriers decreased significantly at the same incubation conditions. As shown in FIG. 23, treatment with 1-7 µM of tocotrienol-rich-fraction as either tocotrienol-rich-fraction/BSA or tocotrienol-rich-fraction-nanostructured lipid carriers significantly (p<0.05) inhibited +SA cell growth in a dose-responsive manner, as compared to cells treated with unloaded solid lipid nanoparticles. The 50% growth inhibition ($IC_{50}$) values for tocotrienol-rich-fraction/BSA and tocotrienol-rich-fraction-nanostructured lipid carriers are given in Table XI. Overall, $IC_{50}$ values for the tocotrienol-rich-fraction-nanostructured lipid carriers were lower than the $IC_{50}$ value for the tocotrienol-rich-fraction/BSA solution. Tocotrienol-rich-fraction-10-nanostructured lipid carriers had significantly (p<0.05) lower $IC_{50}$ values than those observed for the tocotrienol-rich-fraction-50-nanostructured lipid carriers of the same lipid type.

TABLE XI $IC_{50}$ values for tocotrienol-rich-fraction/BSA, tocotrienol-rich-fraction-50-nanostructured lipid carriers, and tocotrienol-rich-fraction-10-nanostructured lipid carriers (mean ± SEM, n = 6)

| Formulation | Secondary lipid | $IC_{50}$ (µM) |
|---|---|---|
| tocotrienol-rich-fraction/BSA | N/A | 2.73 ± 0.11 |
| tocotrienol-rich-fraction-50-nanostructured lipid carriers | Cetyl palmitate | 2.12 ± 0.21 |
|  | glyceryl behenate | 2.08 ± 0.003 |
|  | glyceryl palmitostearate | 2.15 ± 0.007 |
|  | glyceryl tristearate | 1.51 ± 0.05 |
| tocotrienol-rich-fraction-10-nanostructured lipid carriers | Cetyl palmitate | 1.25 ± 0.13 |
|  | glyceryl behenate | 1.22 ± 0.05 |
|  | glyceryl palmitostearate | 1.67 ± 0.14 |
|  | glyceryl tristearate | 1.46 ± 0.08 |

Anti-proliferation data shown in FIG. 23, however, demonstrated that entrapment of tocotrienol-rich-fraction within nanostructured lipid carriers increased their potency, which was evident from the $IC_{50}$ values shown in table XI and the viability of the cells treated with tocotrienol-rich-fraction-nanostructured lipid carriers at 10% tocotrienol-rich-fraction load. The observed decrease in cell viability might be attributed to improved tocotrienol-rich-fraction encapsulation and internalization of the nanostructured lipid carriers by endocytosis into the cells. The importance of drug encapsulation could explain the higher number of viable cells when treated with tocotrienol-rich-fraction-nanostructured lipid carriers at 50% tocotrienol-rich-fraction load. Not wishing to be bound by theory, tocotrienol-rich-fraction may form a matrix with the secondary lipid rather than oily nanocompartments within the cores of the nanostructured lipid carriers at higher concentrations. In comparison, the cores of the tocotrienol-rich-fraction-10-nanostructured lipid carriers are composed of 10% tocotrienol-rich-fraction and 90% of the secondary lipid, which might be sufficient for complete tocotrienol-rich-fraction encapsulation. While the secondary or adjuvant lipids were shown to have insignificant effect on cell viability as evident from the data generated for the unloaded solid lipid nanoparticles, the number of viable cells treated with tocotrienol-rich-fraction-nanostructured lipid carriers varied with the type of the lipid used for the preparation of the nanostructured lipid carriers, which could be readily deduced from their $IC_{50}$ data. For example, nanostructured lipid carriers made with 10% tocotrienol-rich-fraction and 90% glyceryl behenate as a secondary lipid had the greatest impact on cell viability when compared to the nanostructured lipid carriers made from the other lipids. These results might be attributed to the chemical differences between the lipids that affect their ability to efficiently encapsulate tocotrienol-rich-fraction to form the inner cores of the nanostructured lipid carriers or differences in how those lipids interact with the cells.

The compositions associated with examples 3(A)-3(F) may be delivered intravenously, intraperitoneally, subcutaneously, intramuscularly, ocularly, orally, transdermally, topically or by inhalation.

In a prophetic example, any of the individual compounds disclosed herein could be administered to a human patient having a need for cancer prevention or treatment by any one of the various known means of drug administration.

The data contained in examples 3(A)-3(F) tends to indicate that many of the compositions disclosed herein are capable of causing the body to absorb tocotrienol at levels greater than typically associated with the oral consumption of tocotrienol. In a prophetic example compositions disclosed herein may be administered orally or by any other known means causing a blood concentration of tocotrienol in the mammal greater than 4 µM.

Research associated with the individual groups of examples 1(A)-1(D), 2(A)-2(K), and 3(A)-3(F) were conducted in groups, and for that reason contextual interpretation of terms and concepts should be sought within a related group of examples before seeking context from other examples within the application.

Ratios and percentages presented herein are weight based percentages and weight based ratios unless otherwise indicated.

As used herein, the term "therapeutic amount" indicates an amount which is sufficient to effect beneficial or desired clinical results. As used herein, the term "tocotrienol" includes the various isoforms of tocotrienol and compounds which may be derived from one or more of those isoforms and share beneficial therapeutic properties with one or more of the isoforms of tocotrienol. As used herein the terms "surfactant" and "surface active agent" refer to compounds that are capable of significantly lowering the surface tension of a liquid. As used herein, the term "pharmaceutically acceptable salt" refers to a salt prepared from any one or multiple non-toxic acid(s) or base(s), including both organic and inorganic acids and bases that are suitable for use in contact with living animal or human tissue without causing adverse physiological responses.

Any and all reference to patents, documents and other writings contained herein shall not be construed as an admission as to their status with respect to being or not being prior art. It is understood that the array of features and embodiments taught herein may be combined and rearranged in a large number of additional combinations not directly disclosed, as will be apparent to one having skill in the art. There are, of course, other alternate embodiments which are obvious from the foregoing descriptions of the invention, which are intended to be included within the scope of the invention, as defined by the following claims.

We claim:

1. A pharmacological composition comprising:
   a. a group of particles having a mean diameter of less than or about 1000 nm;
   b. wherein the particles contain a therapeutic amount of tocotrienol;
   c. wherein the particles contain a non-tocotrienol lipid;
   d. wherein the particles entrap the tocotrienol in a stable form;
   e. wherein the group of particles have a polydispersity index below 0.3; and
   d. wherein the melting point of the non-tocotrienol lipid is greater than or about 50° C.

2. A pharmacological composition comprising a group of particles
   a. wherein the particles contain a statin and a tocotrienol;
   b. wherein the statin and the tocotrienol are present in a quantity sufficient to deliver a beneficial therapeutic effect;
   c. wherein the particles of the group of particles have a particle size average of less than 1000 nm;
   d. wherein the particles contain a non-tocotrienol lipid;
   e. wherein the melting point of the non-tocotrienol lipid is greater than or about 37° C.;
   f. wherein the particles contain a surfactant; and
   g. wherein the statin is a statin selected from the group consisting of atorvastatin, cerivastatin, fluvastatin, lovastatin, mevastatin, pitavastatin, pravastatin, rosuvastatin, and simvastatin.

3. The pharmacological composition of claim 2 wherein the surfactant is poloxamer.

4. A method of treating a form of cancer comprising administering to a mammalian patient in need of said treatment either a first therapeutic amount of a composition or a second therapeutic amount of a pharmaceutically acceptable salt of said composition, wherein said composition comprises a group of particles
   a. wherein the particles contain a statin and a tocotrienol;
   b. wherein the statin and the tocotrienol are present in a quantity sufficient to deliver a beneficial therapeutic effect;
   c. wherein the particles of the group of particles have a particle size average of less than 1000 nm;
   d. wherein the particles contain a non-tocotrienol lipid;
   e. wherein the melting point of the non-tocotrienol lipid is greater than or about 37° C.;
   f. wherein the particles contain a surfactant; and
   g. wherein the statin is a statin selected from the group consisting of atorvastatin, cerivastatin, fluvastatin, lovastatin, mevastatin, pitavastatin, pravastatin, rosuvastatin, and simvastatin.

5. A pharmacological composition comprising:
   a. a group of particles
   b. wherein the particles of the group of particles have a mean diameter of less than or about 250 nm;
   c. wherein the group of particles contains a therapeutic amount of tocotrienol;
   d. wherein the group of particles contains a non-tocotrienol lipid;
   e. wherein the group of particles contains a surface active agent;
   f. wherein the weight ratio of all surface active agents within the group of particles to all lipids within the group of particles is between about 0.25 to 1.0 and about 3.0 to 1.0;
   g. wherein the group of particles has a polydispersity index below 0.3;
   h. wherein the melting point of the non-tocotrienol lipid is greater than or about 50° C.;
   i. wherein the melting point of the surface active agent is greater than or about 50° C.; and
   j. wherein the surface active agent has surface active agent properties associated with surface active agents that rate 10 or greater on the hydrophilic-lipophilic balance scale.

6. The composition of claim 5 wherein particles from the group of particles are capable of absorption by cancerous cells at a tocotrienol delivery rate that is greater than the rate of tocotrienol delivery from a comparable quantity of tocotrienol delivered without the non-tocotrienol lipid.

7. The pharmacological composition of claim 5
   a. wherein the weight ratio of all surface active agents within the group of particles to all lipids within the group of particles is about 0.5 to 1.0;
   b. wherein the non-tocotrienol lipid is a lipid capable of forming nanostructured lipid carriers containing tocotrienol with a mean particle diameter of less than 100 nanometers;
   c. wherein the non-tocotrienol lipid is a lipid that is capable of enhancing the anti-proliferative effect of the tocotrienol as compared to a comparable quantity of tocotrienol delivered without the non-tocotrienol lipid; and
   d. wherein the groups of particles are capable of absorption by cancerous cells at a tocotrienol delivery rate that is greater than the rate of tocotrienol delivery from a comparable quantity of tocotrienol delivered without the non-tocotrienol lipid.

* * * * *